United States Patent [19]

Lo et al.

[11] Patent Number: 5,025,031

[45] Date of Patent: Jun. 18, 1991

[54] ARYL AND ARYLOXYALKYL SULFAMATE ESTERS USEFUL AS ANTICONVULSANTS

[75] Inventors: Young S. Lo; David A. Walsh, both of Richmond; Ibrahim M. Uwaydah, Chesterfield, all of Va.

[73] Assignee: A. H. Robins Co., Inc., Richmond, Va.

[21] Appl. No.: 443,146

[22] Filed: Nov. 30, 1989

[51] Int. Cl.$^5$ .................. A61K 31/415; A61K 31/255
[52] U.S. Cl. ..................... 514/399; 514/517; 514/397; 514/383; 548/336; 558/47; 558/48
[58] Field of Search ............. 548/265.8, 346, 336; 514/383, 397, 399, 517; 558/47, 48

[56] References Cited

U.S. PATENT DOCUMENTS

| | | | |
|---|---|---|---|
| 2,839,562 | 6/1958 | Wegler et al. | 558/48 |
| 3,082,238 | 3/1963 | Dunbar | 558/48 |
| 4,222,767 | 3/1979 | Gates et al. | 558/47 |

FOREIGN PATENT DOCUMENTS 1554976 12/1968 France ................... 558/47

Primary Examiner—Mary C. Lee
Assistant Examiner—Lenora Miltenberger

[57] ABSTRACT

Herein disclosed is a method of treating convulsions with a pharmaceutical composition containing a compound of the formula:

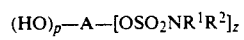

$(HO)_p-A-[OSO_2NR^1R^2]_z$ where A is an aryl, arylalkyl, or aryloxyalkyl group and is substituted on 1 or more carbon atoms with a sulfamate group ($-OSO_2NR^1R^2$) wherein $R^1$ and $R^2$, same or different, are hydrogen or loweralkyl wherein p is 0 or 1 and is the number of untreated hydroxyl groups and z is 1 or 2 and is the number of $-OS(O_2)NR^1R^2$ groups. Aryl is selected from phenyl, substituted phenyl, pyridinyl, naphthyl, quinolinyl, and the like. Phenyl substituents are selected from hydrogen, halo, hydroxy, phenyl, phenoxy, benzoyl, loweralkyl, loweralkoxy, carboxy, amino, loweralkylamino, diloweralkylamino, acetamido, cyano, nitro, loweralkoxycarboyl, aminosulfonyl, imidazolyl, triazolyl, and the like. Novel compounds not previously disclosed are also described.

14 Claims, No Drawings

5,025,031

ARYL AND ARYLOXYALKYL SULFAMATE ESTERS USEFUL AS ANTICONVULSANTS

BACKGROUND OF THE INVENTION

1. Field of Invention

The present invention is concerned with the use of aryl and aryloxyalkyl compounds which carry one or more sulfamate radicals as anticonvulsants useful in the treatment of convulsions in mammals.

2. Information Disclosure Statement

Esterification of glycols having the formula $HOCH_2(CRR')_nCH_2OH$ wherein $R,R'=H$, alkyl, or aryl; $n=0-8$; with $R^2R^3NSO_2Cl$ wherein $R^2$, $R^3=H$, alkyl, aryl or $R^2R^3N=$pyrrolidinyl, or piperidinyl; to give $(R^2R^3NSO_2OCH_2)_2(CRR')_n$ which compounds are useful as contraceptives and have been disclosed in Ger. Offen. 2,559,210 (C.A. 85, 142662w). While the compounds do fall within the scope of those useful in the methods of this invention, the utility is different. Formula I compounds of the present invention do not fall within the scope of this earlier disclosure.

U.S. Pat. No. 4,513,006 discloses anticonvulsant and carbonic anhydrase inhibiting properties of sulfamate esters of the formula:

where $X=O$ or $CH_2$, $R^1$ is hydrogen or lower alkyl, and $R^2$, $R^3$, $R^4$ and $R^5$ are hydrogen, loweralkyl and when X is $CH_2$, $R^4$ and $R^5$ may form a benzene ring and when X is O, $R^2$ and $R^3$ and/or $R^4$ and $R^5$ together may form a methylenedioxy group of the formula:

where $R^6$ and $R^7$ are hydrogen, loweralky, or $R^6$ and $R^7$ together form a cyclopentyl or cyclohexyl ring.

Sulfamates of 2,3,4,5-bis-O-(1-methylethylidene)-β-D-fructopyranose and related compounds such as 2,2-dimethyl-1,3-dioxolan-4-yl)methyl sulfamate and compounds of the formula $Ph-CHRCH_2OSO_2NH_2$ are disclosed in U.S. Pat. No. 4,591,601 and J. Med. Chem. (1987) 30, pp. 880–887 as having anticonvulsant activity. Certain of the compounds of the present invention having the formula $ArO(CR'R^2)_mOSO_2NH_2$ appear to be somewhat similar but are novel.

Compounds having the formula wherein $R^3$ and $R^4$ are hydrogen or loweralkyl and $R^2$ is methyl, ethyl, alkyl, etc. are disclosed in Ger. Offen. 2,417,764 (C.A. 84, 30709q) as herbicides.

Erucyl sulfamate and oleyl sulfamate are disclosed in U.S. Pat. No. 3,661,830 as slip additives for polyethylene. In contrast, in a preferred novel method of this invention, alcohols are treated with sulfamic acid phenyl ester in boiling p-dioxane with a non-nucleophilic organic base to prepare compounds of Formula I.

2-Hydroxyaryl sulfamate esters having the formula $2-OH-C_6H_4-OSO_2NHCH_2Ph$ are disclosed in J. Org. Chem. (1980) 45(26), 5373–5 (C.A. 94, 15312t) as intermediates in the preparation of sulfamides.

Some of the compounds of this invention are included in a co-pending U.S. application, Ser. No. 365,212 filed June 12, 1989, which discloses the novelty and utility of these compounds in treating chronic arthritis and osteoporosis and a process for preparing the compounds. Additional novel compounds are disclosed in the present invention.

SUMMARY OF THE INVENTION

Compounds of Formula I are useful in the pharmaceutical methods of this invention $$(HO)_p-A-[-OSO_2NR^1R^2]_z \qquad \text{Formula I}$$

wherein A is substituted on one or more carbon atoms by an aminosulfonyloxy radical, i.e., a radical having the formula $-OSO_2NR^1R^2$, said A being selected from the group consisting of aryl, arylalkyl, or aryloxyalkyl with a proviso that when A is arylalkyl, z is always two if the aryl moiety is phenyl.

Aryl or aryl moieties are selected from:

X is selected from hydrogen, halo, phenyl, phenoxy, benzoyl, loweralkyl, loweralkoxy, carboxy, amino, loweralkylamino, diloweralkylamino, acetamido, cyano, nitro, loweralkoxycarbonyl, 1H-imidazo-1-yl, aminosulfonyl, 4-phenyl-1H-imidazol-1-yl, 4-methyl-1H-imidazo-1-yl, 1-triazolyl, 2-methyl-1H-imidazol-1-yl, phenylloweralkoxy, or hydroxy;

$z=1$ or 2, and the number of $-OS(O)_2NR^1R^2$ groups;

$P=0$ or 1 and the number of unreacted hydroxyl groups;

$R^1$ and $R^2$, same or different, are hydrogen or loweralkyl;

The optical isomers thereof, when they can be formed; and the pharmaceutically acceptable salts thereof, when they can be formed.

Terms used in the present invention are as defined herein below.

The term "halo" or "halogen" includes chlorine, fluorine, bromine, or iodine unless otherwise specified.

The term "alkyl" as used herein unless otherwise specified includes straight and branched chain radicals of up to 12 carbons inclusive and is exemplified by such groups as methyl, ethyl, propyl, isopropyl, butyl, sec-butyl, tert-butyl, amyl, isoamyl, hexyl, heptyl, octyl, nonyl, decyl, lauryl and the like and is intended to include methylene chains and branched methylene chains when appropriate under the definitions in the formulas. Loweralkyl radicals have 1-8 carbon atoms.

The term "loweralkoxy" means radicals composed of a loweralkyl group attached to an oxygen atom.

Elaborating further on the use of the term "wherein A is substituted on one or two carbon atoms by an aminosulfonyloxy radical," the aminosulfonyloxy radical represented by $-OS(O)_2NR^1R^2$ may be located singly or doubly on aryl, heteroaryl, or alkyl moieties at any site on one or two carbon atoms capable of being hydroxylated. Where there are two aminosulfonyloxy radicals, they may be attached to adjacent carbons or may be separated by intervening carbons or carbons and one or more oxygen atoms where said carbons can be either alkyl or aryl carbons.

By the term "optical isomers" is meant isomers of compounds of Formula I which may exist when chiral centers are present in the A moiety of the Formula I compound. It should be noted that when chiral centers exist in the compounds of Formula I there is potential for the separation of optical isomers otherwise known as enantiomers.

Exemplary of the methods utilized for the separation of optical isomers of compounds of Formula I is the use of column chromatography wherein the column has an appropriate chiral stationary phase. An additional method which may be employed is the use of optically active acids or bases to resolve the enantiomers in successive recrystallizations of the diastereomeric salts. It is also noted that compounds of Formula I which have chiral centers may be prepared by chiral synthesis methods, if so desired, when the same are applicable to the preparation of a particular optical isomer of a Formula I compound.

Pharmaceutically acceptable salts of compounds of the present invention generally form when a heterocyclic nitrogen or a basic nitrogen component is present in A and includes salts of either strong or weak acids. Representative of strong acids are hydrochloric, sulfuric, and phosphoric acids. Representative of weak acids are maleic, fumaric, succinic, oxalic, citric, tartaric, hexamic and the like.

The procedure used for testing the compounds of this invention for anticonvulsant activity is based on evaluation of protective activity against seizures induced by electrical stimulus using a modification of the method of Goodman et al., J. Pharmacology and Experimental Therapeutics 108, 168–176 (1953).

Compounds of Formula I are prepared by Methods I, II and III following:

METHOD I

The process of Method I is represented by the following general equation:

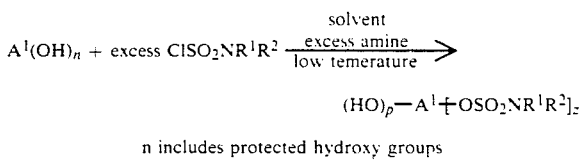

n includes protected hydroxy groups wherein values for $A^1$ include those in the definition for A of Formula I with the proviso that $A^1$ may additionally carry protected carboxy, protected amino or protected hydroxy groups and a further proviso alternative is that aryl may be a group outside the definition of A carrying non-interfering radicals. Compounds prepared under the latter proviso wherein $A^1$ is aryl are useful as reagents in Method II.

$R^1$ = hydrogen, loweralkyl or $-C(O)OR^3$,
$R^2$ = hydrogen or loweralkyl,
$R^3$ = loweralkyl, or phenylloweralkyl,
n = p + z
p = number of unreacted hydroxyl groups including zero,
z = number of sulfamate esterified hydroxy groups.

Protected carboxy groups are represented by benzyloxycarbonyl and trichlorethyloxycarbonyl.

Protected amino groups are represented by benzyloxycarbonylamino and trichlorethyloxy carbonyl amino.

Protected hydroxy groups are represented by benzyloxycarbonyloxy or trichloroethyloxycarbonyloxy.

Protected carboxy groups, protected amino groups or protected hydroxy groups are deprotected by hydrogenolysis in the instance of benzyloxy carbonyl radicals and deprotected by treating with zinc/acetic acid in the instance of trichloroethyloxycarbonyl radicals.

Generally in Method I, the reaction is carried out in a non-reactive aprotic organic solvent suitably methylene chloride or acetonitrile at temperatures over a range of 0°–100° C. In some instances non-interfering tertiary organic bases such as triethylamine, pyridine or diisopropylethylamine are beneficially added to absorb the hydrochloric acid which is liberated. Products are isolated by various conventional means as illustrated in the examples.

Method I in conjunction with known protection group chemistry can be used to prepare certain types of Formula I compounds as illustrated in Chart I and Example 5.

CHART I

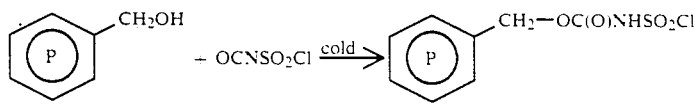

CHART I
-continued

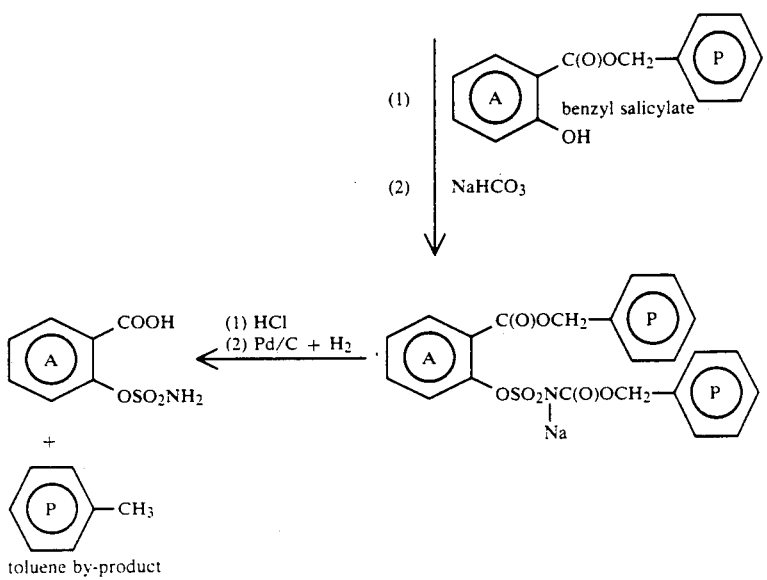

Footnotes Chart I:
P designates radicals involved with protection.
A represents product or core product intermediate.

Carboxy groups in other positions are contemplated. Other groups substitutable for

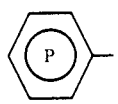

such as pyridinyl, naphthenyl, and biphenyl are also contemplated.

METHOD II—GENERAL

Method II is represented by the following equation:

$A^1(OH)_n$ +

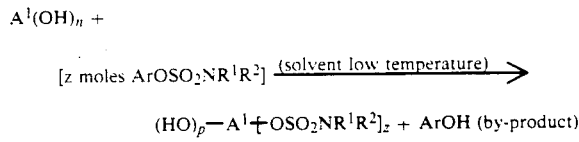

$(HO)_p-A^1+OSO_2NR^1R^2]_z$ + ArOH (by-product)

wherein Ar is an aryl group carrying non-interfering radicals and may be an aryl group outside the definition of A or $A^1$;

wherein values for $A^1$ include those in the definition for A of Formula I with the proviso that when $A^1$ is aryl protected carboxy, protected amino or protected hydroxy groups are substituted for carboxy, amino or hydroxy, said protected hydroxy being excluded from $(OH)_n$, i.e., when $p=0$, $n=z$.

$R^1$ = hydrogen, loweralkyl or $-C(O)OR^3$,
$R^2$ = hydrogen or loweralkyl,
$R^3$ = loweralkyl, or phenylloweralkyl,
$n = p + z$
$p$ = number of unreacted hydroxyl groups including zero,
$z$ = number of sulfamate esterified hydroxy groups.

Protected carboxy groups are represented by benzyloxycarbonyl and trichlorethyloxycarbonyl.

Protected amino groups are represented by benzyloxycarbonylamino and trichlorethyloxy carbonyl amino.

Protected hydroxy groups are represented by benzyloxycarbonyloxy or trichlorethyloxycarbonyloxy.

Protected carboxy groups, protected amino groups or protected hydroxy groups are deprotected by hydrogenolysis in the instance of benzyloxycarbonyl radicals and deprotected by treating with zinc/acetic acid in the instance of trichloroethyloxycarbonyl radicals.

Method II, hereinabove outlined, represents a novel process for synthesizing Formula I compounds disclosed in our copending application Ser. No. 365,212 filed on June 12, 1989, and is described more fully as follows: In an organic solvent system consisting of a non-reactive aprotic solvent containing from about 1 to about 20% of a tertiary organic base, and preferably at least 5% of said tertiary organic base, there are reacted at a temperature of from about 50° to 200° C. and preferably at about 90° to 140° C., a reagent sulfamic acid aryl ester and a hydroxy substituted $A^1$ radical wherein $A^1$ is defined as A under Formula I above, except that $A^1$ may not be aryl substituted by unprotected carboxy or unprotected amino, and $A^1$ may additionally be substituted by a protected hydroxy, but wherein said protected hydroxy is excluded from $(OH)_n$ in the equations above. If $A^1$ is substituted by protected amino, protected carboxy or protected hydroxy, then the protected groups are deprotected subsequent to the transfer of the aminosulfonyloxy radical from the sulfamic acid aryl ester reactant, thus giving the desired formula I compound. In addition to forming the desired Formula I compound in the reaction there is also formed a hydroxy substituted aryl by-product in the reaction. After the desired Formula I compound is formed in the reaction it is extracted from the reaction mixture by partitioning between an organic and aqueous layer and recrystallization by methods commonly known in the art to give a Formula I compound as a free base. A pharmaceutically acceptable salt of the free base may be obtained by reacting with a pharmaceutically acceptable acid in conventional manner.

This method for preparing Formula I compounds, labeled as Method II reaction above, may also be referred to as the transfer reaction herein, in as much as the sulfamic acid ester group originally present on the sulfamic acid aryl ester reactant may be considered to be transferred to the hydroxy substituted $A^1$ radical, and the hydroxy substituent on the $A^1$ radical may be considered to be transferred to the aryl radical of the previous sulfamic acid ester group. The aryl group contained on the initial sulfamic acid aryl ester may be selected from aryl as defined under Formula I or from aryl other than that as defined under Formula I, to the extent that the selected aryl substituent is not to be substituted by a radical which would interfere with the transfer of the aminosulfonyloxy radical from the sulfamic acid aryl ester group to the hydroxy substituted $A^1$ reactant. It should be noted that if the aryl substituent of the sulfamic acid aryl ester is the same as the $A^1$ substituent of the hydroxy substituted $A^1$ reactant, then the net effect of the reaction would be zero since the products of the reaction would be equivalent to the reactants, therefore the aryl radical of the sulfamic acid aryl ester should never be identical to the $A^1$ radical of the hydroxy substituted $A^1$ reactant in this method. It should also be understood that this method may be employed to prepare a Formula I compound from another Formula I compound if the Formula I compound utilized in the preparation of the second Formula I compound has an aryl A substituent with no interfering radicals substituted thereon, such as hydroxy, amino, carboxy and the like.

METHOD III—GENERAL

Certain compounds of Formula I and reagents for use in Method II may also be prepared by reaction represented by the following equation:

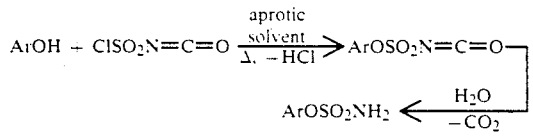

Generally in Method III, the reaction is carried out in a non-reactive aprotic solvent, suitably toluene, chlorobenzene or acetonitrile at temperatures over a range of 80°-150° C.

The preparation of chemical intermediates is illustrated in the following preparations. The examples following the preparations illustrate the synthesis methods for preparing compounds of Formula I. The scope of the present invention is not limited by the descriptive methods and procedures of the preparations and examples, however.

PREPARATION 1

2-Phenoxy-1,3-propanediol.

To a stirred solution of 11.9 g (0.517 mole) of sodium in 500 ml of absolute ethanol was added in portions 48.4 g (0.514 mole) of phenol. After stirring a few minutes to form the sodium phenoxide, 100 g (0.514 mole) of diethyl 2-chloromalonate was added dropwise. The reaction mixture was then heated at reflux temperature for 5 hr. The mixture was concentrated in vacuo and the residue treated with 500 ml of water. This mixture was extracted with three 300 ml portions of ether. The combined extract was washed with 300 ml of water, dried (magnesium sulfate) and concentrated to obtain 107 g (82% yield) of diethyl 2-phenoxymalonate.

A solution of 84.7 g of the ester in 250 ml anhydrous ether was added dropwise to a stirred suspension of 14.1 g (0.372 mole) of lithium aluminum hydride in 350 ml of anhydrous ether at such a rate so as to maintain a gentle reflux. When the addition was completed the mixture was stirred at ambient temperature for 2 hr and then treated cautiously with successive dropwise additions of 14 g of water, 42 g of 15% sodium hydroxide solution, and 42 g of water while the mixture was stirred vigorously. The mixture was then treated with 300 ml of ethyl acetate and stirred for a few minutes. The mixture was then filtered, the filter cake washed with an additional 300 ml of ethyl acetate, and the combined filtrate layers washed twice with 400 ml portions of water. The organic solution was dried (magnesium sulfate) and concentrated in vacuo to give 39 g (69% yield) of the title compound as a viscous oil.

PREPARATION 2

[1-[(2-Methoxyphenoxy)methyl]-1,2-ethanediylbis(oxysulfonyl)] biscarbamic acid bis 1-methylethyl ester To a solution of chlorosulfonyl isocyanate (154 g, 1.09 mole) in 300 ml methylene chloride stirred in an ice bath was added a solution of 2-propanol (83.2 ml, 1.09 mole) in 100 ml methylene chloride over 26 min. The ice bath was removed after addition and the reaction was stirred for 2.5 hours. The reaction was then filtered through a Celite ® cake to remove a small amount of solid and the filtrate was concentrated to a solid. The solid was triturated in petroleum ether and then collected under nitrogen by filtration. The solid was rinsed with petroleum ether and dried under vacuum in a desiccator to give 212.68 g (96.5% yield) of the isopropyl ester of N-chlorosulfonyl carbamic acid. A slight suspension of glyceryl guaicolate (8 g, 0.04 mole) in pyridine (8.1 ml, 0.1 mole) and methylene chloride (50 ml) was poured into a solution of the isopropyl ester of chlorosulfonyl carbamic acid in 30 ml methylene chloride stirred in an ice bath. The exothermic reaction caused a gentle boiling. The ice bath was removed after the addition and the reaction stirred for 20 min. The organic layer was separated and washed twice with water. The product was then extracted into three portions of sodium bicarbonate solution. The combined bicarbonate solution was stirred with methylene chloride in an ice bath and sulfuric acid was added to acidify the mixture. The layers were separated and the aqueous layer was extracted once more with methylene chloride. The combined organic layers were backwashed with water. The methylene chloride solutions were dried oversodium sulfate, filtered, and concentrated to an oil weighing 23 g. Proton NMR showed desired product with a small amount of methylene chloride. About 10 g of the above oil was freeze-dried from benzene giving a clear oil. Proton NMR showed 0.25 mole of benzene was present.

Analysis: Calculated for $C_{18}H_{28}N_2O_{12}S_2.0.25C_6H_6$: C, 42.73; H, 5.43; N, 5.11. Found: C, 42.40; H, 5.47; N, 5.00.

PREPARATION 3

3-Phenoxy-1-propanol

To a stirred suspension of 5.7 g (0.15 mole) of lithium aluminum hydride in 350 ml of dry ethyl ether was added dropwise (30 min) a solution of 25.0 g (0.149 mole) of 3-phenoxypropionic acid (99%, Aldrich Chem. Co.) in 250 ml of dry ethyl ether. The reaction mixture was stirred at ambient temperature for 2 hr and treated successively with 6 ml of water, 18 ml of a 15% sodium hydroxide solution, and 10 ml of water. The reaction mixture was filtered through Celite ® and the filtrate was concentrated to a viscous residue. The residue was partitioned between water and ethyl ether (300 ml each). The ethereal layer was washed with two 300 ml portions of water, dried over magnesium sulfate and the solvent was evaporated under reduced pressure to give 16.6 g (73%) of the title compound as a colorless oil.

Analysis: Calculated for $C_9H_{12}O_2$: C, 71.03; H, 7.95. Found: C, 71.09; H, 8.10.

PREPARATION 4

3-(4-Chlorophenoxy)-1,2-propanediol

A mixture of 25.7 g (3.2 mole) of 4-chlorophenol, 18.5 g (0.25 mole) of glycidol and 1 ml of pyridine was stirred and heated at 85°–90° C. overnight. The pot residue was partitioned between ethyl ether and water. The organic layer was washed with water and brine, dried over sodium sulfate, and concentrated to give a gum which crystallized when triturated with petroleum ether (boiling point range, 30°–60° C.). The solid was collected by filtration and recrystallized from isopropyl ether to yield 27.2 g (67%) of off-white solid, mp 73°–75° C. (lit[1] mp 77° C.).

[1] W. Bradley and J. Forrest, Brit 628,497 (1949); Chem Abstr. 44, 3023 eg (1950).

Analysis: Calculated for $C_9H_{11}ClO_3$: C, 53.35; H, 5.47. Found: C, 53.02; H, 5.56.

PREPARATION 5

2-(3-Methoxyphenoxy)ethanol

This compound was prepared by the procedure of Preparation 3. Thus, 36.5 g (0.2 mole) of 3-methoxyphenoxyacetic acid (Lancaster Synthesis, Inc., Windham, NH 03087) and 7.7 g (0.2 mole) of lithium aluminum hydride (Aldrich) in 600 ml of ethyl ether gave 25.7 g (76%) of light-yellow oil.

Analysis: Calculated for $C_9H_{12}O_3$: C, 64.27; H, 7.19. Found: C, 63.93; N, 7.10.

PREPARATION 6

2-Phenoxy-2,2-dimethyl acetic acid

To a solution of 20.0 g (0.93 mole) of 2-(4-chlorophenoxy)-2-methylpropionic acid (97%, clofibric acid, Aldrich) in 130 ml of methanol and 50 ml of dioxane was added a solution of 13.9 g (0.244 mole) of potassium hydroxide in 75 ml of water. To this solution were added 5 teaspoonfuls of Raney ® nickel (Aldrich) and the mixture was hydrogenated at ambient temperature for 3.25 hr ($H_2$-uptake ceased). The reaction mixture was filtered through Celite ® and the filtrate was concentrated under reduced pressure to a volume of 150 ml. This solution was extracted with 200 ml of ethyl ether and the ether was discarded. The aqueous layer was adjusted to pH 2 with concentrated hydrochloric acid solution and the resulting white solid was collected by filtration and dried to give 16 g (99%) of white solid. An analytical sample was prepared by recrystallizing from cyclohexane-petroleum ether (b.p. range 30°–60° C.) to give white crystals, mp 98°–100° C.

Analysis: Calculated for $C_{10}H_{12}O_3$: C, 66.65; H, 6.71. Found: C, 66.53; H, 6.72.

PREPARATION 7

3-(1H-Imidazol-1-yl)phenol

This compound was prepared by modifying a procedure of L. M. Sitkina and A. M. Simonov abstracted in CA 65:1386e.

Imidazole (34 g, 0.5 mole), m-bromoanisole (51 ml, 0.4 mole), potassium carbonate (52 g), and cuprous chloride (2.4 g) in 300 ml N-methyl-2-pyrrolidone was heated at reflux for 4 hours. The cooled mixture was diluted with water and 100 ml concentrated ammonium hydroxide. The product was extracted into toluene-ethyl acetate (several times until TLC of aqueous layer showed only a trace amount of product). All the organic extracts were combined, filtered, extracted once with water and then three times with a total of 300 ml 48% hydrobromic acid. The hydrobromic acid extracts were combined and heated at reflux for 6 hours and then concentrated. The residue was redissolved in water and basified first with sodium hydroxide and at the end with sodium bicarbonate to get a final pH of 8. Some isopropyl ether was added to cause the product to crystallize. The solid was collected by filtration, washed with water, and dried at 80° C. in a vacuum oven to obtain 50.9 g (79.5% yield). A small portion of this solid was dissolved in absolute ethanol, filtered, concentrated, and recrystallized. The recrystallized material melted at 169°–170° C.

Analysis: Calculated for $C_9H_8N_2O$: C, 67.49; H, 5.03; N, 17.49. Found: C, 67.28; H, 5.12; N, 17.16.

PREPARATION 8

1,1-Dimethyl-2-phenoxyethanol

To a stirred solution of 24.2 g (0.16 mole) of phenoxy-2-propanone (Eastman) in 150 mL of dry ethyl ether was added 56 ml (0.17 mole) of methylmagnesium bromide (3.0M solution in ethyl ether, Aldrich) and the reaction mixture was stirred at ambient temperature under a nitrogen atmosphere for 4 hr. The reaction mixture was treated with 100 ml of saturated ammonium chloride solution and vigorously stirred for 1 hr. The layers were separated and the organic layer was washed twice with 200 ml portions of water, dried (magnesium sulfate) and the solvent evaporated under reduced pressure to yield 24.3 g (91%) of a vicous oil. A 2.3 g sample of the oil was purified by high pressure liquid chromatography (Waters Associates Prep LC/System 500 A; PrepPAK ® 500 silica; ethyl acetate-hexanes, 1:20; flow rate 150 ml/min). The desired fractions were combined and the solvents evaporated under reduced pressure to yield 2.1 g (91% recovery) of the title compound as a colorless liquid.

Analysis: Calculated for $C_{10}H_{14}O_2$: C, 72.26; H, 8.49. Found: C, 72.08; H, 8.46.

PREPARATION 9

3-(4-Methyl-1H-imidazol-1-yl)phenol

A mixture of 3-bromoanisole (25.5 ml, 0.2 mole), 4-methyl-imidazole (21 g, 0.25 mole), potassium carbonate (26 g), and cuprous chloride (1.2 g) in 150 ml of N-methyl-2-pyrrolidone was reacted and worked up as described in Preparation 27.

The phenolic product isolated as precipitate from water had a slightly wet weight of 31 g and $^{13}C$ NMR showed a 4:1 isomer ratio. This solid was dissolved in hot isopropyl alcohol, treated with charcoal, filtered, concentrated, and crystallized to give 11.69 g of off-white solid. $^{13}$C NMR showed only one isomer, mp 203°–205° C.

Analysis: Calculated for $C_{10}H_{10}N_2O$: C, 68.95; H, 5.79; N, 16.08. Found: C, 69.32; H, 5.68; N, 16.08.

PREPARATION 10

R-(−)2,2-Dimethyl-4-(2-methoxyphenoxy)-1,3-dioxolane

This compound was prepared from 5.72 g (0.02 mole) of S(+)-3-tosyloxy-1,2-propanediol acetonide and 0.03 mole of sodium guaiacolate in 76% yield according to the procedure of W. L. Nelson et al., *J. Org. Chem.* 42, 1066, 1977. The mp=43°–44° C., $[\alpha]_D^{22} -8.0°$ (c=2 in dimethylformamide).

Analysis: Calculated for $C_{13}H_{18}O_4$: C, 65.53; H, 7.61. Found: C, 65.38; H, 7.45.

PREPARATION 11

S-(+)2,2-Dimethyl-4-(2-methoxyphenoxy)-1,3-dioxolane

This compound was prepared from 49.4 g (0.173 mole) of R(−)-3-tosyloxy-1,2-propanediol acetonide and 0.26 mole of sodium guaiacolate in 68% yield according to the procedure of W. L. Nelson et al., *J. Org. Chem.* 42, 1066, 1977. The mp=44.5°–45.5° C., $[\alpha]_D^{22} +8.5°$ (c=2 in dimethylformamide).

Analysis: Calculated for $C_{13}H_{18}O_4$: C, 65.53; H, 7.61. Found C, 65.53; H, 7.69.

PREPARATION 12

S-(+)-Glyceryl guaiacolate

Hydrolysis of 20 g (0.084 mole) of R-(−)-2,2-dimethyl-4-(2-methoxyphenoxy)-1,3-dioxolane according to the procedure of W. L. Nelson et al, *J. Org. Chem.* 42, 1066 (1977) gave 14.2 g (85%) of the title compound, mp 93°–94.5° C., $[\alpha]_D^{22} +8.80°$ (c=2 in methanol).

Analysis: Calculated for $C_{10}H_{14}O_4$: C, 60.60; H, 7.12. Found: C, 60.53; H, 6.98.

PREPARATION 13

R-(−)Glyceryl guaiacolate

Hydrolysis of 27.0 g (0.113 mole) of S-(+)-2,2-dimethyl-4-(2-methoxyphenoxy)-1,3-dioxolane according to the procedure of W. L. Nelson et al, *J. Org. Chem.* 43, 1066 (1977) gave 21.5 g (96%) of the title compound, mp 93.5°–95° C., $[\alpha]_D^{22} -9.05°$ (c=2 in methanol).

Analysis: Calculated for $C_{10}H_{14}O_4$: C, 60.60; H, 7.12. Found: C, 60.56; H, 7.05.

PREPARATION 14

3-(4-Phenyl-1H-imidazol-1yl)phenol

Following the procedure for preparation of 3-(1H-imidazol-1-yl)phenol (preparation 7), 4-phenylimidazole (20 g, 0.138 mole) and 3-bromoanisole (32 ml, 0.25 mole) were reacted to give the title compound in 57% yield, mp 195°–197° C.

Analysis: Calculated for $C_{15}H_{12}O$: C, 76.25; H, 11.86. Found: C, 75.98; H, 11.67.

PREPARATION 15

2-[3-(1H-Imidazol-1-yl)phenoxy]ethanol

A slurry of 16.0 g (0.10 mole) of 3-(imidazol-1-yl)phenol and 42 g (0.3 mole) of potassium carbonate in 100 ml of methyl ethyl ketone was heated to reflux with stirring. The mixture was treated with 25.5 g (0.3 mole) of chloroethanol by dropwise addition over a 2 hr period. The mixture was heated at reflux for an additional 18 hr then treated with an additional 16.1 g (0.2 mole) of chloroethanol and 27.6 (0.2 mol) of potassium carbonate. After an additional 22 hr heating at reflux all starting material was consumed. The reaction mixture was filtered and the filtrate was concentrated. The residue was partitioned between methylene chloride and 0.1N sodium hydroxide solution. The organic layer was concentrated and the residue was crystallized from ethyl acetate to give 10.2 g (50%) of the title compound as tan crystals, mp 81.0°–83.0° C.

Analysis: Calculated for $C_{11}H_{12}N_2O_2$: C, 64.69; H, 5.92; N, 13.72. Found: C, 64.50; H, 5.87; N, 13.56.

PREPARATION 16

3-(2-Methyl-1H-imidazol-1-yl)phenol

A stirred mixture of 3-bromoanisole (100 g, 0.53 mole), 2-methylimidazole (41 g, 0.50 mole), potassium carbonate (96 g, 0.60 mole), cuprous chloride (2.5 g) and N-methyl-2-pyrrolidinone (300 ml) was heated at reflux temperature for 15 hr and then concentrated to remove the solvent and excess 3-bromoanisole. The residue was partitioned between ethyl acetate and water. The ethyl acetate layer was concentrated to a black syrup that was then dissolved in toluene and extracted twice with water and then extracted with 48% hydrobromic acid solution. The hydrobromic acid extract was heated at reflux temperature for 7 hr and then distillation of water and methylbromide was begun with addition of additional 48% hydrobromic acid solution as necessary to maintain a reasonable volume. Distillation was continued until the distillation head temperature reached 124° C. The mixture was concentrated under vacuum. The concentrate was diluted with 500 ml of water and basified to pH 8 with addition of potassium carbonate in small portions. The precipitate was collected, washed with water, and dried to give 39.7 g. Recrystallization from 50% aqueous ethanol gave 31.4 g (36%) mp 178°–181° C.

Analysis: Calculated for $C_{10}H_{10}N_2O$: C, 68.95; H, 5.79; N, 16.08. Found: C, 68.71; H, 5.75; N, 15.94.

PREPARATION 17

2-[4-(1H-1,2,4-Triazol-1-yl)phenoxy]ethanol

A stirred mixture of 4-(1H-1,2,4-triazol-1-yl)phenol (16.1 g, 0.10 mole), 2-chloroethanol (25.5 g, 0.30 mole), potassium carbonate (42 g, 0.30 mole) and methyl ethyl ketone (100 ml) was heated at reflux temperature for 10 hr. An additional 16.1 g (0.20 mole) of 2-chloroethanol was added to the reaction mixture and heating at reflux temperature continued for another 24 hr. The hot mixture was filtered and the filtrate chilled. The crystalline precipitate was collected by filtration and the filter cake rinsed with water to remove most of the dark color. The solid was triturated with hot ethyl acetate, the mixture cooled, and the light-tan crystals collected to yield 14.0 g (68%), mp 151°–152° C.

Analysis: Calculated for $C_{10}H_{11}N_3O_2$: C, 58.53; H, 5.40; N, 20.48. Found: C, 58.35; H, 5.36; N, 20.27.

PREPARATION 18

3-(2-Ethoxyphenoxy)-1,2-propanediol

A solution of 41.5 g (0.3 mole) of 2-ethoxyphenol, 29.6 g (0.4 mole) of glycidol, 2 ml of pyridine and 150 ml of absolute ethanol was heated at reflux temperature for 18 hr. The mixture was concentrated to a thick oil that crystallized slowly over several days. The crude product was chromatographed on a silica gel column (1.2 kg) using increasing portions of acetone in methylene chloride to elute the product. The desired fractions were combined and concentrated to give a yellow oil that crystallized on standing. The solid was triturated with petroleum ether and the mixture filtered to obtain 41.8 g of solid. Recrystallization from carbon tetrachloride yielded 37.2 g (58%) of white solid, mp 64°–65° C.

Analysis: Calculated for $C_{11}H_6O_4$: C, 62.25; H, 7.60. Found: C, 62.34; H, 7.72.

PREPARATION 19

3-[4-(1H-Imidazol-1-yl)phenoxy]-1-propanol.

A stirred mixture of 4-(1H-imidazol-1-yl)phenol (16.0 g, 0.10 mole), 3-chloropropanol (19.0 g, 0.20 mole), potassium carbonate (28 g, 0.20 mole) and methyl ethyl ketone (100 ml) was heated at reflux temperature for 24 hr. The reaction mixture was cooled, filtered, and the filtrate concentrated. The residue was partitioned between ethyl acetate and 0.01N sodium hydroxide solution. The ethyl acetate layer was dried (magnesium sulfate), diluted with ether, and the solid precipitate collected. The solid was recrystallized from methyl isobutyl ketone to obtain 10.0 g (46%), mp 76°–78° C.

Analysis: Calculated for $C_{12}H_{19}N_2O_4$: C, 66.04; H, 6.47; N, 12.84. Found: C, 65.87; H, 6.48; N, 12.71.

PREPARATION 20

3-[2-(Phenylmethoxy)phenoxy]-1,2-propanediol

A solution of 49.6 g (0.248 mole) of 2-benzyloxyphenol, 22.2 g (0.3 mole) of glycidol, 2 ml of pyridine and 150 ml of absolute ethanol was heated at reflux overnight. The dark solution was concentrated to give an oil which gradually crystallized. The solid was purified by column chromatography on 1.2 kg of silica gel eluted with 0-25% acetone in benzene. Appropriate fractions were combined and concentrated to yield 49.5 g (73%) of the title compound as a white solid, mp 84°–85° C. (carbon tetrachloride) (lit.[1] mp 81°–82.5° C.).
[1] J. Swidinsky, J. Kervenski & B. B. Brown, J. Pharm. Sci. 52:955-8 (1963).

Analysis: Calculated for $C_{16}H_{18}O_4$: C, 70.06; H 6.61. Found: C, 69.96; H, 6.60.

PREPARATION 21

2-[3-(4-Methyl-1H-imidazol-1-yl)phenoxy]ethanol monohydrochloride 3-(4-Methyl-1H-imidazol-1-yl)phenol (13.1 g, 0.075 mole), chloroethanol (20.2 ml, 0.3 mole), and potassium carbonate (42 g, 0.3 mole) were heated at reflux in 200 ml methyl ethyl ketone for 7 hours. TLC of a sample showed some starting phenol remaining. Chloroethanol (10 ml) was added to the reaction and it was kept at reflux temperature overnight. The solid was filtered and rinsed with acetone. The filtrate and rinsings were concentrated to an oil and dissolved in 1:1 acetonitrile-toluene. The filtered solid was dissolved in water and the solution was used to extract the organic solution. The aqueous layer was separated and extracted once more with 1:1 acetonitrile-toluene. The organic layers were washed with potassium carbonate solution, dried, filtered, and concentrated to give 16.7 g of dark brown oil. The oil was dissolved in 2-propanol and acidified with a solution of hydrogen chloride in 2-propanol and the salt crystallized from 2-propanol/isopropyl ether. The brown solid was collected and recrystallized from 2-propanol to give 9.07 g of light brown solid which was dried in a vacuum oven overnight at 60° C., mp 164°–165° C.

Analysis: Calculated for $C_{12}H_{14}N_2O_2.HCl$: C, 56.59; H, 5.94; N, 11.00. Found: C, 56.44; H, 6.03; N, 10.90.

PREPARATION 22

2-(2-methoxyphenoxy)ethanol

A solution of 43.2 g (0.35 mole) of 2-methoxyphenol (guaiacol, Aldrich) in 200 ml of ethanol was stirred and treated with 29 ml (0.36 mole) of 50% sodium hydroxide solution. To this solution was added a solution of 28.2 g (0.35 mole) of 2-chloroethanol (Aldrich) in 50 ml of ethanol and the reaction mixture was heated at reflux for 2 hr. The solids were removed by filtration. The filtrate was evaporeated under reduced pressure and the viscous residue was partitioned between 300 ml of 15% sodium hydroxide solution and 500 ml of ethyl ether. The organic layer was washed with 200 ml of 15% sodium hydroxide solution, 300 ml of water, dried (magnesium sulfate) and the solvent evaporated under reduced pressure to give 24.5 g (42%) of the title compound as a lightly colored, viscous oil.

An analytical sample was prepared from this oil by high pressure liquid chromatography purification (Waters Associates Prep LC/System 500 A; PrepPak ® 500 silica; ethyl acetate-hexanes, 1:2; flow rate 200 ml/min). Fractions containing the title compound were combined and the solvents evaporated under reduced pressure to yield the title compound as a colorless liquid.

Analysis: Calculated for $C_9H_{12}O_3$: C, 64.27; H, 7.19. Found: C, 63.93; H, 7.32.

PREPARATION 23

2-[3-(Phenylmethoxy)phenoxy]ethanol

A slurry of 38.6 g (0.25 mole) of o-(2-hydroxyethyl)-resorcinol (Lancaster), 44.3 g (0.35 mole) of benzyl chloride, and 55.2 g (0.40 mole) of potassium carbonate in 200 ml of acetone was stirred and heated at reflux for 72 hr. The reaction mixture was filtered and the filtrate was concentrated under vacuum. The crystalline residue was recrystallized from toluene/petroleum ether to give 56.3 g (92%) of the title compound as white flakes, mp 40.5°–43.5° C.

Analysis: Calculated for $C_{15}H_{16}O_3$: C, 73.75; H, 6.60. Found: C, 73.68; H, 6.53.

PREPARATION 24

3-[2-(1H-imidazol-1-yl)ethoxy]phenol

A solution of 12.2 g (0.05 mole) 2-[3-(phenylmethoxy)phenoxy]ethanol and 5.6 g (0.555 mole) of triethylamine in 100 ml of THF was cooled to 0° C. with stirring and treated dropwise with 6.4 g (0.055 mole) of mesyl chloride over a 20-min period. The mixture was stirred at 10° C. or less for 1 hr, then filtered. The filtrate was combined with a slurry of 0.10 mole of imidazole sodium salt in 50 ml of THF and the mixture was heated at reflux for 8 hr. The 50 ml of THF and the mixture was heated at reflux for 8 hr. The cooled reaction mixture was filtered and the filtrate was partitioned between ethyl acetate/ether and water. The organic layer was concentrated to give 14.7 g (100%) of crude intermediate. This syrup (13.0 g) was dissolved in 100 ml of methanol and hydrogenated at 40° C. and 45 psi $H_2$ using 1 g of 10% Pd/C catalyst. This mixture was filtered, and the filtrate was concentrated to give 9.0 g (100%) of crude, crystalline product. A portion was recrystallized from toluene/methyl isobutyl ketone to give the title compound as white crystals, mp 125.0° C.-127.0° C.

Analysis: Calculated for $C_{11}H_{12}N_2O_2$: C, 64.69; H, 5.92; N, 13.72. Found: C, 64.72; H, 5.97; N, 13.74.

PREPARATION 25

3-(4-Iodophenoxy)-1,2-propanediol

A solution of 28.1 g (0.127 mole) of 4-iodophenol, 11.6 g (0.16 mole) of glycidol, 2 ml of pyridine, and 125 ml of absolute ethanol was heated at reflux overnight. The dark solution was concentrated to give a brown, solid residue. The residue was triturated several times with boiling carbon tetrachloride and the liquid decanted. The combined carbon tetrachloride washings were heated, filtered and cooled, and a solid crystallized. The solid was collected by filtration and dried to yield 9.4 g (25%) of a pale yellow solid. An analytical sample, mp 101.5°-103.5° C. (lit.[1] mp 106°-107° C.) was prepared from $CCl_4$.

[1] O. Radek and O. Nemecek. Cesk. Farm. 13, 456-9(1964); Chem. Abstr. 62, 3966f(1965).

Analysis: Calculated for $C_9H_{11}IO_3$: C, 36.76; H, 3.77. Found: C, 36.82; H, 3.81.

PREPARATION 26

2-(3-Nitrophenoxy)ethanol

A mixture of m-nitrophenol (28 g, 0.2 mole), 2-chloroethanol (53.6 ml, 0.8 mole), and potassium carbonate (110.4 g, 0.8 mole) in 300 ml methyl ethyl ketone was kept at reflux temperature with stirring overnight. The solid was filtered and dissolved in water. The filtrate was concentrated and some solid was crystallized from 2-propanol/isopropyl ether. This light-brown solid was collected and weighed 22.78 g(62%). The mother liquor was concentrated and redissolved in toluene/ethyl acetate and extracted with the above aqueous solution. The aqueous layer was further extracted with fresh toluene/ethyl acetate. The combined organic layers were washed with water, dried over sodium sulfate, filtered, and concentrated to give a second crop of 6.46 g (17.6%). The second crop was dissolved in methanol, stirred with charcoal, filtered, evaporated, and crystallized from 2-propanol/isopropyl ether to give a pure sample. The sample was dried under vacuum at room temperature overnight, mp 85°-86° C.

Analysis: Calculated for $C_8H_9NO_4$: C, 52.46; H, 4.95; N, 7.65. Found: C, 52.41; H, 4.96; N, 7.65.

PREPARATION 27

4-(2-Methyl-1H-imidazol-1-yl)phenol

To a 3-neck, 1-liter, round-bottom flask was added 2-methylimidazole (41.0 g, 0.50 mole), 4-bromoanisole (100 g, 0.53 mole) and potassium carbonate (96.0 g, 0.70 mole) in N-methyl-2-pyrrolidinone (300 ml). A small amount of cuprous chloride (2.5 g) was added. The stirred reaction mixture was heated at reflux temperature for 24 hr and then the N-methyl-2-pyrrolidinone and excess bromoanisole gently distilled. The black pot residue was partitioned between toluene and water and a black solid removed by filtration. The toluene layer was extracted with 48% hydrobromic acid (2×200 ml) and the hydrobromic acid solution was heated at reflux temperature 3 hr then stirred at room temperature overnight. The solution was then concentrated, diluted with water (500 ml) and made basic with sodium hydroxide and sodium bicarbonate solutions. The white solid which precipitated was collected and dried and a small amount recrystallized from methanol/isopropyl alcohol. The total yield was 24.88 g (28.6% yield), mp 205°-208° C.

Analysis: Calculated for $C_{10}H_{10}N_2O$: C, 68.95; H, 5.79; N, 16.08. Found: C, 68.58; H, 5.67; N, 15.84.

PREPARATION 28

4-(1-Methyl-1H-imidazol-2-yl)phenol

Hydrogen chloride gas was bubbled through a chilled solution of p-cyanophenol (30 g, 0.25 mole) in methanol (120 mo) for 70 min. The heavy suspension was stoppered and stirred overnight. After cooling in an ice bath, the solid was collected by filtration and rinsed twice with cold methanol. The solid was dried under nitrogen to give 46.56 g. The solid iminoether was resuspended in methanol (150 ml) and treated with methylamino acetaldehyde dimethyl acetal (42 ml, 0.325 m) and then heated at reflux temperature for 3 hr. The reaction was then concentrated to an oil which was redissolved in 2N hydrochloric acid solution (200 ml). The solution was then concentrated to remove the methanol and the resulting aqueous solution was extracted twice with methylene chloride and then made basic first with 50% sodium hydroxide solution and finishing up with 10% sodium bicarbonate solution. The solid was collected and rinsed with water, 2-propanol and isopropyl ether. The solid was dissolved in methanol, treated with charcoal and filtered. The filtrate was partially concentrated by boiling and replacing the methanol with 2-propanol, from which a white, crystalline solid precipitated out of solution. The solid was filtered and dried (14.4 g, 0.083 mole, 66.7% yield, mp 239°-242° C.).

Analysis: Calculated for $C_{10}H_{10}N_2O$: C, 68.95, H, 5.79; N, 16.08 Found: C, 69.17; H, 5.74; N, 16.16

PREPARATION 29

2-[4-(2-Methyl-1H-imidazol-1-yl)phenoxy]ethanol 4-(2-Methyl-1H-imidazol-1-yl)phenol (10.0 g, 0.057 mole), 2-chloroethanol (13.88 g, 0.172 mole) and potassium carbonate (23.74 g, 0.172 mole) were combined in methyl ethyl ketone (200 ml) and heated at reflux temperature for four days. The solution was cooled and the solid filtered and rinsed with acetone. The filtrate was concentrated to a residue and the residue triturated with hot acetone (2×50 ml). The remaining solid (1.5 g) was dissolved in methylene chloride. Insoluble materials were removed by filtration, and the filtrate concentrated to obtain 0.50 g (4%), mp 125°-127° C. Proton NMR indicates that methylene chloride is present in the sample.

Analysis: Calculated for $C_{12}H_{14}N_2O_2 \cdot 0.1\ CH_2Cl_2$: C, 64.10; H, 6.31; N, 12.35. Found: C, 64.24; H, 6.36; N, 12.30.

PREPARATION 30

1-(4-Methoxyphenyl)-1H-imidazole

A mixture of 37.4 g (0.20 mole) of 4-bromoanisole, 170 g (0.25 mole) of imidazole, 26 g (0.2 mole) of potassium carbonate, and 1.2 g of cuprous bromide in 150 ml of N-methylprryolidinone was heated at reflux under a blanket of nitrogen for 4 hr. The mixture filtered and concentrated to remove the solvent. The residue was partioned between dilute sodium hydroxide solution and methylene chloride. After filtration, the organic fraction was chromatographed. The desired fractions were concentrated and the crystalline residue was recrystallized from toluene/cyclohexane to give 17.4 g (50%) of the title compound as white plates, mp 63.0–64.0° C.

Analysis: Calculated for $C_{10}H_{10}N_2O$: C, 68.95; H, 5.79; N, 16.08. Found: C, 68.91; H, 4.73; N, 16.05.

PREPARATION 31

2-(2-Methoxyphenoxy)propanedioic acid diethyl ester

To a solution of 6.9 g (0.3 mole) of sodium pellets dissolved in 400 ml of absolute ethanol was successively added a solution of 37.9 g (0.305 mole) of guaiacol in 50 ml of ethanol followed by a solution of 68.1 g(0.35 mole) of diethylchloromalonate in 50 ml of ethanol. The mixture was heated at reflux for 28 hr and then stirred at ambient temperature for 3 days. The mixture was filtered and the filtrate was concentrated. The residue was partitioned between salt water and ethyl ether. The layers were separated and the aqueous layer was extracted twice with 150 ml portions of ethyl ether. The combined organic layers were washed with brine, dried (sodium sulfate) and concentrated to give a yellow oil. The oil was subjected to vacuum distillation and 66.6 g (79%) of the title compound was collected as a clear oil, bp 136°–153° C. at 0.3 mm.

Analysis: Calculated for $C_{14}H_{13}O_6$: C, 59.57; H, 6.43. Found: C, 59.46; H, 6.67.

PREPARATION 32

2-(2-Phenoxyethyl)propane-1,3-diol

A solution of 30.0 g (0.11 mole) of 2-(phenoxyethyl)-diethyl malonate (Alfred Bader/Aldrich) in 100 ml of dry tetrahydrofuran (THF) was added dropwise to a stirred suspension of 6.1 g (0.16 mole) of lithium aluminum hydride (Aldrich) in 100 ml of dry THF. The reaction mixture was stirred at ambient temperature for 2 hr, treated successively with 15 ml of water, 20 ml of 15% sodium hydroxide solution and 25 ml of water. The solids were removed by filtration and the filter cake was washed with 100 ml of water and 300 ml of ethyl ether. The filtrate layers were separated and the organic layer was washed with two 300 ml fractions of water, dried (magnesium sulfate) and the solvents were evaporated under reduced pressure to give a colorless, viscous oil that solidified upon standing. The solid was recrystallized from methylene chloride to yield 12.4 g (59%) of a white solid, mp 71°–73° C.

Analysis: Calculated for $C_{11}H_{16}O_3$: C, 67.32; H, 8.22. Found: C, 67.33; H, 8.40.

PREPARATION 33

2-(4-Chlorophenoxy)propanedioic acid diethyl ester

A mixture of 38.6 g (0.3 mole) of 4-chlorophenol, 70 g (0.36 mole) of diethylchloromalonate and 69.1 g (0.5 mole) of anhydrous potassium carbonate in 750 ml of acetone was heated at reflux for 48 hr, cooled, filtered and the filtrate concentrated. The residue was diluted with 250 ml of ethyl ether and was washed successively with two 100 ml portions of a 1% NaOH solution, once with $H_2O$ and once with brine, dried (sodium sulfate) and concentrated to give an oil which gradually crystallized. The solid was triturated with petroleum ether (30°–60° C.), collected by filtration and dried to yield 72.6 g (84%) of white solid. An analytical sample, mp 43.5°–45° C. (lit.[1] mp 58°–60° C.), was recrystallized from petroleum ether (60°–110° C.).

[1] V. P. Manaev and M. A. Mikhaleva, *Szv. Sibirsh. Otd. Akad. Nauk SSSR*, 145–8 (1962); Chem. Abstr. 59,5051f (1963).

Analysis: Calculated for $C_{13}H_{15}ClO_5$: C, 54.46; H, 5.27. Found: C, 54.49; H, 5.35.

PREPARATION 34

2-(2-Naphthyloxy)propanedioic acid diethyl ester

This compound was prepared following Procedure 33. Thus, a mixture of 43.2 g (0.3 mole) of 2-naphthol, 70 g (0.36 mole) of diethylchloromalonate and 69.1 g (0.5 mole) of anhydous potassium carbonate in 750 ml of acetone gave 84.0 g (93%) of a tan solid. An analytical sample, mp 57°–58.5° C. (lit.[1] mp 57°–58° C.), was recrystallized from isopropyl ether.

[1] B. Kirkiacharion and C. Mentzer, Fr. 1,465,584 (Jan. 13, 1967); Chem. Abstr. 67,82102e, (1967).

Analysis: Calculated for $C_{17}H_{15}O_5$: C, 67.54; H, 6.00. Found: C, 67.58; H, 6.05.

PREPARATION 35

2-(4-Phenylmethoxy)phenoxy ethanol

A mixture of 130.4 g (0.65 mole) of 4-benzyloxyphenol (Eastman), 93.0 g (1.16 mole) of 2-chlorethanol (Aldrich) and 26.0 g (0.65 mole) of sodium hydroxide pellets in 750 ml of ethanol was stirred and heated at reflux for 20 hr. The reaction mixture was filtered and the filtrate was concentrated under reduced pressure to a solid residue. The solid was partitioned between 300 ml of 15% sodium hydroxide solution and 600 ml of methylene chloride. The organic layer was further washed with 200 ml of 15% sodium hydroxide solution, two 300 ml fractions of water, dried (magnesium sulfate) and the solvent was evaporated under reduced pressure to give 81.0 g of a solid. The solid was recrystallized (charcoal treated) from methylene chloride-petroleum ether (30°–60° C.) to give 78.5 g (92%, based on amount of 4-benzyloxyphenol consumed) of crystals, mp 102.5°–104.5° C.

Analysis: Calculated for $C_{15}H_{16}O_3$: C, 73.75; H, 6.60. Found: C, 73.73; H, 6.72.

PREPARATION 36

4-(4,5-Dihydro-1-methyl-1H-imidazol-2-yl)phenol hemihydrate

Anhydrous hydrogen chloride gas was bubbled into a cold (0° C.) stirred solution of p-cyanophenol (30 g, 0.25 mole) in 120 ml methanol for 70 min. The resultant heavy suspension was stopped and stirred overnight. After cooling in an ice bath, the solid was collected by filtration and rinsed twice with cold methanol. The solid was then dried under nitrogen to a weight of 46.56 g. The solid was resuspended in 150 ml methanol, chilled in an ice bath, and N-methylethylenediamine (22 g, 0.25 mole) was added. The reaction became a clear solution and it was heated at reflux temperature for one hour. The solvent was then evaporated and the residual oil was dissolved in water. It was basified first using 50% sodium hydroxide solution and then using sodium bicarbonate solution. The solid was collected by filtration and rinsed with water, 2-propanol, and isopropyl ether. The slightly wet solid weighed 20.71 g. The mother liquor and rinsings were combined and concentrated to yield a second crop which weighed 22.55 g. A portion of the first crop was recrystallized from acetonitrile/methanol, filtered and dried, mp 122°–125° C.

Analysis: Calculated for $C_{10}H_{12}N_2O \cdot 0.5H_2O$: C, 64.85; H, 7.07; N, 15.12. Found: C, 65.19; H, 7.08; N, 15.17.

PREPARATION 37

1-(2-Chloro-5-methoxyphenyl)-1H-imidazole

A mixture of 6-chloro-m-anisidine hydrochloride (21.48 g, 0.11 mole), triethylamine (15.2 ml, 0.11 mole) and 150 ml trimethyl orthoformate was heated at reflux for 3.5 hours. To the mixture was added 150 ml of toluene and some charcoal. After stirring, the mixture was filtered and the filtrate was evaporated to an oil. The oil was redissolved in 150 ml of methanol and reacted with aminoacetaldehyde dimethyl acetal (12 ml, 0.11 mole) at reflux for four hours. The reaction was concentrated and the residue was dissolved in toluene. The toluene solution was extracted twice (total volume 100 ml) with 2N hydrochloric acid solution. The extracts were combined, heated at reflux temperature for five hours, and then concentrated. The residue was dissolved in water and neutralized first with 50% sodium hydroxide and finished up with sodium bicarbonate solution. Some oily material deposited and crystallized upon addition of toluene. The mixture was filtered, the layers of the filtrate were separated, and the aqueous layer extracted three times with toluene-acetonitrile. The organic layers were combined, dried over sodium sulfate, and concentrated to a dark brown oil (15 g). TLC (silica gel eluted with 10% methanol in methylene chloride) of this oil showed mainly two spots at Rf 0.8 and 0.2. The oil was chromatographed on 150 g of silica gel and eluted with 10% methanol in methylene chloride.

About 10 g material of $R_f$ 0.8 was collected. A portion of this was recrystallized from toluene, collected and rinsed with toluene-isopropyl ether, and dried in vacuo at room temperature overnight to give an analytical sample, mp 79°–81° C.

Analysis: Calculated for $C_{10}H_9ClN_2O$: C, 57.57; H, 4.35; N, 13.43. Found: C, 57.48; H, 4.23; N, 13.36.

PREPARATION 38

2-(4-Chlorophenoxy)-1,3-propanediol.

To a stirred slurry of 11.4 g (0.3 mole) of lithium aluminum hydride (LAH) in 200 ml of freshly distilled (from LAH) tetrahydrofuran (THF) was added dropwise a solution of 57.3 g (0.2 mole) of 2-(4-chlorophenoxy)-1,3-propanedioic acid diethyl ester (C. A.59:5051f(1963); Mamaev and Mikhaleva. *Isv.Sibirsk.Otd. Akad.Nauk. SSSR*, 145–8 (1962)) in 150 ml of THF at such a rate that a gentle reflux was maintained. The mixture was stirred at ambient temperature for 5 hr and then the excess LAH was decomposed with successive, cautious, dropwise additions of 11.4 ml of water, 11.4 ml of a 15% sodium hydroxide solution, and 34 ml of water. A gelationous precipitate developed which was filtered through Celite with great difficulty. The filtrate was concentrated and the residue was purified by column chromatography on 500 g of silica gel eluted with 0–35% acetone in benzene. The appropriate fractions were combined and concentrated to give an oil which gradually crystallized. The solid was triturated with petroleum ether (30°–60° C.), collected by filtration, and dried to yield 18.2 g (45%) of white solid, mp 62°–64° C. (isopropyl ether).

Analysis: Calculated for $C_9H_{11}ClO_3$: C, 53.35; H, 5.47. Found: C, 53.51; H, 5.52.

PREPARATION 39

4-Chloro-3-(1H-imidazol-1-yl)phenol 1-chloro-2-(1H-imidazol-1-yl)-4-methoxybenzene (7.5 g, 0.036 m) was mixed with 40 ml 48% hydrobromic acid. The solution was distilled until the head temperature reached 120° C. and the reaction was then heated at reflux for two hours. The reaction was concentrated under reduced pressure. The residue was triturated in isopropyl alcohol-isopropyl ether and the solid was collected. The solid was dissolved in water and poured into a saturated solution of sodium bicarbonate. The solid was collected and rinsed with water, isopropyl alcohol-isopropyl ether, and isopropyl ether to give 6.65 g of solid. A small portion of this solid was recrystallized by dissolving in methanol-isopropyl alcohol, treated with charcoal, filtered, and evaporated to remove most of the methanol. A white solid was obtained which was dried at 70° C. under vacuum overnight, mp 204°–205° C.

Analysis: Calculated for $C_9H_7ClN_2O$: C, 55.54; H, 3.63; N, 14.39. Found: C, 55.37; H, 3.50 N, 14.36.

EXAMPLE 1

Sulfamic acid 3-(2-methoxyphenoxy)-1,2-propanediyl ester

A. Preparation of Sulfamoyl Chloride Solution in Execess Acetonitrile

To a solution of 13.1 ml (0.15 mole) of chlorosulfonyl isocyanate in 20 ml of acetonitrile with agitation and cooling in an acetone-ice bath was added slowly dropwise a solution of 2.7 ml (0.15 mole) of water in 10 ml (excess) acetonitrile at −5° C. to +5° C. over a 15 min period. Upon addition of each drop, vigorous evolution of carbon dioxide was noted. The solution was stirred in the cold bath for 15 minutes after addition was complete.

B. Preparation of the Title Compound.

To the above prepared sulfamoyl chloride solution was added 8 g (0.04 mole) of 3-(2-methoxyphenoxy)-1,2-methoxyphenoxy)-1,2-propanediol (glyceryl guaiacolate) in a solution of 15.2 ml (0.176 mole) of pyridine in 20 ml of acetonitrile at −3° C. to +15° C. over a 13 min period. The cold bath was removed and the reaction mixture was stirred for 2 hr. Ethyl acetate (30 ml) was added and the mixture was extracted thrice with saturated sodium chloride solution. The combined aqueous layers were extracted twice with a 1:1 mixture of ethyl acetate:acetonitrile. The organic layers were combined and dried over sodium sulfate and evaporated to give a glassy residue. Crystallization using isopropyl alcohol and isopropyl ether produced 10.3 g (74.5%) of slightly impure title product in 2 crops. The crystals were triturated with water and a small amount of isopropyl alcohol, filtered, dried and dissolved in warm acetonitrile. A small amount of solid was removed by filtration. The filtrate was mixed with water and subjected to slow evaporation. The resulting suspension was filtered and the solid was rinsed with water, isopropyl alcohol and isopropyl ether. The white solid was dried in a vacuum oven at 40° C. overnight, mp 151°–153° C.

Analysis: Calculated for $C_{10}H_{16}N_2O_8S_2$: C, 33.70; H, 4.53; N, 7.86. Found: C, 34.16; H, 4.65; N, 8.20.

EXAMPLE 2

Methylsulfamic acid 3-(2-methoxyphenoxy)-1,2-propanediyl ester.

a. Preparation of N-Methylsulfamoyl Chloride

A mixture of 16.2 g (0.235 mole) of 98% purity methylamine hydrochloride, 19.4 ml (0.235 mole) of 97% purity sulfuryl chloride and 0.2 ml of antimony (V) chloride in 70 ml of acetonitrile was heated at reflux for 4 hr. To the reaction mixture was added another 19.4 ml (0.235 mole) of sulfuryl chloride and reflux was continued overnight. The reaction mixture changed from a suspension to a brown solution. The solution was concentrated under reduced pressure and then pumped under vacuum to give 30 g of brown oil. $^1$H NMR analysis showed the oil to be mainly N-methylsulfamoyl chloride.

b. Preparation of Title Compound

A solution of 8 g (0.04 mole) of 3-(2-methoxyphenoxy)-1,2-propanediol (glyceryl guaiacolate) in 13 ml (0.16 mole) of pyridine and 40 ml of methylene chloride was added in a thin stream to a solution of 20.72 g (ca. 0.16 mole) of the crude N-methylsulfamoyl chloride prepared above in 60 ml of methylene chloride while stirring in a room temperature water bath. After 2 hr stirring, the reaction mixture was extracted twice with water. The organic layer was dried over sodium sulfate, filtered and concentrated to 20.42 g of brown oil. This oil was purified by column chromatography on silica gel column, eluting with 10% ethyl acetate in methylene chloride to give the title compound as a viscous oil.

Analysis: Calculated for $C_{12}H_{20}N_2O_8S_2$: C, 37.49; H, 5.24; N, 7.29. Found: C, 37.07; H, 5.29; N, 7.14.

EXAMPLE 3

Sulfamic acid 3-phenoxy-1,2-propanediyl ester a. Preparation of Sulfamoyl Chloride in Excess Acetonitrile To a solution of 24.8 g (0.175 mole, 15.2 ml) of chlorosulfonyl isocyanate in 100 ml of acetonitrile cooled in an ice-acetone bath was added dropwise a solution of 32 g (0.175 mole) of water in 10 ml of acetonitrile at such a rate that the temperature did not exceed 7° C. (45 min). The mixture was stirred at −3° C. for 15 min after addition was complete.

b. Preparation of Title Compound

To the above sulfamoyl chloride solution in acetonitrile was added dropwise with stirring a solution of 8.4 g (0.05 mole) of 3-phenoxy-1,2-propanediol (95% purity obtained from Aldrich Chem. Co., Inc.) and 20.2 g (0.2 mole) of triethylamine in 50 ml of acetonitrile at such a rate that the temperature did not exceed 12° C. over a 45 min period. The cooling bath was removed and the mixture was stirred for 2 hr and treated with 100 ml of ethyl acetate and 50 ml of water. The mixture was vigorously stirred for 5 min and the layers were separated. The organic layer was washed with 50 ml of water and 100 ml of brine, dried over sodium sulfate and concentrated to give a gum as residue. The gum was purified by column chromatography on 350 g of silica gel. Fractions eluted with 15% acetone in methylene chloride were combined and concentrated to give a clear gum as residue. The gum was triturated with petroleum ether (bp 30°-60° C.) to give crystalline solid. The solid was collected by filtration and recrystallized from benzene-acetonitrile to yield 4.2 g (26% yield) of title compound as a white solid, mp 116°-118° C.

Analysis: Calculated for $C_9H_{14}N_2O_7S_2$: C, 33.12; H, 4.32; N, 8.58. Found: C, 33.16; H, 4.36; N, 8.54.

EXAMPLE 4

Sulfamic acid 2-phenoxyethyl ester a. Preparation of Sulfamoyl Chloride Solution in Excess Acetonitrile.

To a stirred, cooled (ice-acetone bath) solution of 48.8 g (30.4 ml, 0.342 mole) of chlorosulfonyl isocyanate of 98% purity (Aldrich Chemical Co.) in 150 ml of acetonitrile was added dropwise a solution of 6.4 g (0.356 mole) of water in 20 ml of acetonitrile at such a rate that the temperature did not exceed 7° C. Addition time was 40 min. After the addition was completed, the mixture was stirred at −3° C. for 15 min.

b. Preparation of Title Compound

To the solution prepared in (a) was added dropwise a solution of 13.8 g (0.1 mole) of 2-phenoxyethanol and 40.4 g (0.4 mole) of triethylamine in 100 ml of additional acetonitrile at such a rate that the temperature did not exceed 12° C. Addition time was 45 min. The cold bath was removed and the mixture was stirred for 2 hr and then treated with 200 ml of ethyl acetate and 100 ml of water. The mixture was vigorously stirred for 5 min and the layers were separated. The organic layer was washed twice with 100 ml of water, twice with 100 ml portions of saturated sodium chloride solution, dried over sodium sulfate and concentrated at reduced pressure to remove volatiles to give a viscous, oily residue which solidified on standing. The solid was dissolved in 300 ml of methylene chloride and the solution filtered through Celite ®. The filtrate was concentrated to 200 ml volume and again filtered through Celite ®. The filtrate was concentrated further under reduced pressure to give a solid residue. The residue was recrystallized successively from methylene chloride and ethyl acetate-water mixture to give 10.5 g (48% yield) of title compound as white solid, mp 89°-91° C.

Analysis: Calculated for $C_8H_{11}NO_4S$: C, 44.23; H, 5.10; N, 6.45. Found: C, 43.19; H, 5.08; N, 6.84.

EXAMPLE 5

2-[(Aminosulfonyl)oxy]benzoic acid

A. 2-[[(Phenylmethyl)aminosulfonyl]oxy]benzoic acid (phenylmethyl)ester sodium salt A chilled (0° C.) solution of chlorosulfonyl isocyanate (28.31 g, 0.20 mole) in methylene chloride (150 ml) was treated dropwise with a solution of benzyl alcohol (21.63 g, 0.20 mole) in methylene chloride (300 ml) over a period of 12-15 min at 3° C.-15° C. The mixture was stirred without cooling for 2 hr and then chilled with an ice bath again. A solution of benzyl salicylate (22.8 g, 0.1 mole), pyridine (16 ml, 0.2 mole), and 4-dimethylaminopyridine (0.5 g) in 70 ml methylene chloride was added at about 10° C. over 10 minutes. The reaction was stirred overnight at room temperature and then extracted once with dilute hydrochloric acid and once with water. The combined aqueous layers were extracted with methylene chloride. The combined organic layers were dried and evaporated to an oil. The oil was dissolved in a small amount of tetrahydrofuran and filtered to remove some insoluble solid. The THF filtrate was added to about 300 ml saturated sodium bicarbonate solution and the resulting suspension was stirred overnight. The solid was collected by filtration, rinsed twice with water and twice with isopropanol-isopropyl ether and dried to yield 25.88 g (56%) of the sodium salt. A second crop of 5.60 g (12%) was collected.

B. Title Compound

To a suspension of 2-[[(phenylmethyl)aminosulfonyl]oxy]benzoic acid (phenylmethyl)ester sodium salt (35.3 g, 0.076 mole) in methanol (500 ml) was added 6.2 ml of concentrated hydrochloric acid and 2 g of 5% palladium on carbon catalyst wetted with methanol (50 ml). The mixture was hydrogenated for 4 hr and filtered. The filtrate was concentrated to an oil and resuspended in THF. The solids were removed by filtration and the filtrate concentrated. The residue was triturated with 1,1,1-trichloroethane, giving 8.82 g of light purple solid. The solid was dissolved in THF, treated with activated charcoal, filtered, and concentrated again. The residue was recrystallized from 1,1,1-trichloroethane to give 6.5 g of white solid, mp 139°–140° C.

Analysis: Calculated for $C_7H_7NO_5S$: C, 38.71; H, 3.25; N, 6.45. Found: C, 38.16; H, 3.24; N, 6.55.

EXAMPLE 6

Sulfamic acid 3-phenoxypropyl ester a. Sulfamoyl chloride solution was prepared as in Example 4 using: 31.5 ml (0.356 mole) of chlorosulfonyl isocyanate (98%), 6.3 ml (0.35 mole) of water and 150 ml of acetonitrile.

b. The title compound was obtained using the following procedure: The sulfamoyl chloride in acetonitrile solution prepared in (a) was reacted as in Example 4 with 15.6 g (0.102 mole) of 3-phenoxy-1-propanol using 40.2 g (0.398 mole) of triethylamine in 100 ml additional acetonitrile followed by extraction, washing and concentration procedures of Example 4 through the first evaporation. The residue was then purified by chromatography (4 × 90 cm glass column; 500 g silica gel; methylene chloride followed by 10:1 methylene chloride-acetone). Fractions containing the title compound were combined and the solvents were evaporated under reduced pressure to give 15.8 g of viscous oil which solidified on standing. The solid was recrystallized from ethyl acetate to give 14.7 g (62% yield) of title compound as white solid, mp 83°–85° C.

Analysis: Calculated for $C_9H_{13}NO_4S$: C, 46.74; H, 5.67; N, 6.06. Found: C, 46.80; H, 5.73; N, 6.05.

EXAMPLE 7

Sulfamic acid 2-phenoxy-1,3-propanediyl ester a. Sulfamoyl chloride solution was prepared as in Example 4 using: 32 ml (0.368 mole) of chlorosulfonyl isocyanate (98%), 6.4 ml (0.356 mole) of water and 150 ml of acetonitrile.

b. The title compound was obtained using the following procedure: The sulfamoyl chloride prepared in (a) was reacted as in Example 4 with 17.3 g (0.103 mole) of 2-phenoxy-1,3-propanediol and 41.4 g (0.41 mole) of triethylamine in 100 ml of acetonitrile followed by extraction, washing and concentration procedures of Example 4 through the first evaporation. The oily residue was purified by column chromatography on silica gel using methylene chloride and 10:1 methylene chloride/acetone for elution and fractions containing the title compound were combined and concentrated to give a solid residue. The residue was recrystallized using ethyl ether and petroleum ether (bp 30°–60° C.) to give 7.5 g (22%) of white solid, mp 104°–106° C.

Analysis: Calculated for $C_9H_{14}N_2O_7S_2$: C, 33.12; H, 4.32; N, 8.58. Found: C, 33.27; H, 4.36; N, 8.48.

EXAMPLE 8

Dimethylsulfamic acid 2-hydroxy-3-(2-methoxyphenoxy)propyl ester a. Preparation of Dimethylsulfamoyl Chloride A mixture of 28.8 g (0.353 mole) of dimethylamine hydrochloride (98%, Aldrich Chemical Co.), 29.1 ml (0.362 mole) of sulfuryl chloride (97%, Aldrich) and 0.3 ml of antimony (V) pentachloride (Baker Chemical Co.) in 100 ml of acetonitrile was stirred and heated at reflux for 4 hr. An additional 29.1 ml (0.362 mole) of sulfuryl chloride was added and the mixture was heated at reflux overnight. The mixture was concentrated under reduced pressure to give 44.2 g (87%) of dimethylsulfamoyl chloride as a brown liquid.

b. Preparation of Title Compound

To a stirred solution of 21.9 g (152.5 mole) of the dimethylsulfamoyl chloride prepared in (a) above in 60 ml of methylene chloride was added a solution of 7.6 g (0.038 mole) of 3-(2-methoxyphenoxy)-1,2-propanediol (glyceryl guaiacolate) and 12.1 g (0.152 mole) of pyridine in 40 ml of methylene chloride at such a rate that the reaction temperature was maintained at $\leq 12°$ C. The reaction mixture was stirred at ambient temperature for 4 days. Water, 200 ml, was added to the mixture and the layers were separated. The organic layer was washed successively with two 200 ml portions of 2N hydrochloric acid and 200 ml of water, dried over magnesium sulfate and the solvent was evaporated under reduced pressure to give 11.6 g of yellow liquid. The liquid was purified by high pressure chromatography using a Waters Associates Prep LC/System 500 A with PrepPak ® silica. Eluting solvent used was 10:1 mixture of methylene chloride to ethyl acetate at a flow rate of 200 ml/min. Fractions containing the title compound were combined and the solvents were evaporated under reduced pressure to give 3.9 g (33%) of title compound as a yellow, viscous oil.

Analysis: Calculated for $C_{12}H_{19}NO_6S$: C, 47.20; H, 6.27; N, 4.59. Found: C, 47.73; H, 6.14; N, 4.30.

Analysis: Calculated for $C_{12}H_{19}NO_6S \cdot 0.05CH_3CO_2CH_2CH_3$: C, 47.31; H, 6.31; N, 4.56.

EXAMPLE 9

Carbamic acid 2-[(aminosulfonyl)oxy]-3-(2-methoxyphenoxy)propyl ester a. Sulfamoyl chloride solution was prepared as in Example 4 using: 30.4 ml (0.342 mole) of chlorosulfonyl isocyanate (98%), 6.4 g (0.356 mole) of water and 150 ml of acetonitrile.

b. The title compound was obtained using the following procedure: The sulfamoyl chloride in acetonitrile solution prepared in (a) was reacted as in Example 4 with 24.1 g (0.1 mole) of 3-(2-methoxyphenoxy)-1,2-propanediol-1-carbamate and 40.4 g (0.4 mole) of triethylamine in 100 ml acetonitrile followed by extraction, washing and concentration procedures of Example 4 through the first evaporation. The viscous, oily residue (29.1 g) was purified by column chromatography using a 4.5 cm × 100 cm glass column filled with 550 g of silica gel and 10:1 ratio of methylene chloride/acetone as eluting agent. Fractions containing the title compound were combined and the solvents were evaporated under reduced pressure to give 12.6 g of a white solid. The solid was recrystallized from acetone-benzene to give 10.0 g (31%) of title compound as a white solid, mp 119°–122° C.

Analysis: Calculated for $C_{11}H_{16}N_2O_7S$: C, 41.25; H, 5.04; N, 8.75. Found: C, 41.13; H, 5.07; N, 8.71.

EXAMPLE 10

Sulfamic acid 3-phenoxy-1-(phenoxymethyl)ethyl ester a. Sulfamoyl chloride solution was prepared as in Example 4 using: 18.8 ml (0.212 mole) of chlorosulfonyl isocyanate (98%), 3.9 g (0.217 mole) of water and 150 ml of acetonitrile.

b. The title compound was obtained using the following procedure: The sulfamoyl chloride prepared in (a) was reacted as in Example 4 with 15.0 g (0.061 mole) of 1,3-diphenoxy-2propanol (Aldrich Chem. Co.) and 24.8 g (0.246 mole) of triethylamine in 100 ml of acetonitrile followed by extraction, washing and concentration procedures through the first evaporation. The semisolid residue obtained was dissolved in 100 ml of methylene chloride and the solution was filtered through 50 g of silica gel. The silica gel was washed with 600 ml of methylene chloride. The combined methylene chloride solutions were evaporated under reduced pressure and the viscous residue was purified by high pressure liquid chromatography (Waters Associates Prep LC/System 500A; PrepPak® 500 silica using methylene chloride eluting agent at a flow rate of 200 ml/min). Fractions containing the title compound were combined and solvents were evaporated under reduced pressure to give 12.9 g (65%) of title compound as a white solid, mp 81°–84° C.

Analysis: Calculated for $C_{15}H_{17}NO_5S$: C, 55.72; H, 5.30; N, 4.33. Found: C, 55.58; H, 5.27; N, 4.28.

EXAMPLE 11

Sulfamic acid 3-(4-chlorophenoxy)-1,2-propanediyl ester a. Sulfamoyl chloride solution was prepared as in Example 4 using 50.5 ml (0.592 mole) of chlorosulfonyl isocyanate (98%), 10.9 g (0.606 mole) of water and 150 ml of acetonitrile.

b. The title compound was obtained using the following procedure: The sulfamoyl chloride solution prepared in (a) was reacted as in Example 4 using 15.0 g (0.074 mole) of 3-(4-chlorophenoxy)-1,2-propanediol and 69.9 g (0.692 mole) of triethylamine in 100 ml of acetonitrile followed by extraction, washing and concentration procedures of Example 4 through the first evaporation. The viscous, oily residue obtained was purified by high pressure liquid chromatography (Waters Associates Prep LC/System 500A; PrepPak 500® silica; 9:1 methylene chloride-acetone at a flow rate of 200 ml/min). Fractions containing the title compound were combined and the solvents were evaporated under reduced pressure to give 10.2 g of viscous oil. The oil was partitioned between water and ethyl ether (300 ml each). The ether layer was separated and washed with three 200 ml portions of water, dried over sodium sulfate and solvent evaporated under reduced pressure to give 8.9 g (33%) of viscous oil which solidified on standing, mp 101°–104° C.

Analysis: Calculated for $C_9H_{13}ClN_2O_7S_2$: C, 29.96; H, 3.63; N, 7.76. Found: C, 30.36, H, 3.71; N. 7.75.

EXAMPLE 12

Sulfamic acid 2-(2-chlorophenoxy)ethyl ester a. Sulfamoyl chloride solution was prepared as in Example 4 using 30.4 ml (0.342 mole) of chlorosulfonyl isocyanate (98%), 6.4 g (0.356 mole) of water and 150 ml of acetonitrile.

b. The title compound was obtained using the following procedure: The sulfamoyl chloride solution prepared in (a) was reacted as in Example 4 with 17.3 g (0.100 mole) of 2-(2-chlorophenoxy)ethanol and 40.4 g (0.400 mole) of triethylamine in 100 ml of acetonitrile followed by extraction, washing and concentration procedures of Example 4 through the first evaporation. The viscous, oily residue was partitioned between 500 ml of water and 500 ml of ethyl ether. The organic layer was washed with four 300 ml portions of water (pH of wash finally neutral to pH paper), dried over magnesium sulfate and the solvent evaporated under reduced pressure to give a white solid. The solid was recrystallized from ethyl ether-petroleum ether (bp 30°–60° C.) to give 14.5 g (58%) of title compound as white solid, mp 84.5°–86° C.

Analysis: Calculated for $C_8H_{10}ClNO_4S$: C, 38.18; H, 4.01; N, 4.57. Found: C, 38.24; H, 4.03; N, 4.59.

EXAMPLE 13

Sulfamic acid 2-(4-chlorophenoxy)ethyl ester

The title compound was prepared by procedures of Example 4 from sulfamoyl chloride and 2-(4-chlorophenoxy)ethanol in 48% yield. A white solid, mp 117°–119° C., was obtained.

Analysis: Calculated for $C_8H_{10}ClNO_4S$: C, 38.18; H, 4.01; N, 5.57. Found: C, 38.38; H, 4.06; N, 5.66.

EXAMPLE 14

Sulfamic 2-(3-methylphenoxy)ethyl ester

The title compound was prepared by procedures of Example 4 from sulfamoyl chloride and 2-(3-methylphenoxy)ethanol in 47% yield [recrystallizing ethyl ether-petroleum ether (30°–60° C.)]. A white solid, mp 76°–78° C., was obtained.

Analysis: Calculated for $C_9H_{13}NO_4S$: C, 46.74; H, 5.67; N, 6.06. Found: C, 46.79; H, 5.74; N, 6.13.

EXAMPLE 15

Sulfamic 2-(3-methoxyphenoxy)ethyl ester

The title compound was prepared by procedures of Example 4 from sulfamoyl chloride and 2-(3-methoxyphenoxy)ethanol through the first evaporation step to give a brown, viscous, oily residue. The oil was dissolved in 300 ml of ethyl ether. The organic solution was washed with two 300 ml portions of water, dried over magnesium sulfate and the solvent evaporated under reduced pressure to give a viscous, oily residue for the second time. The oil was purified by chromatography using silica gel and methylene chloride-acetone in 90:1 ratio as eluting agent. Fractions containing the title compound were combined and solvents evaporated under reduced pressure to give a viscous oil which solidified on standing. The solid was recrystallized from ethyl-petroleum ether (30°–60° C.) to give the title compound as white solid, mp 78°–82° C., in 46% yield.

Analysis: Calculated for $C_9H_{13}NO_5$: C, 43.72; H, 5.30; N, 5.66. Found: C, 43.77; H, 5.33; N, 5.67.

EXAMPLE 16

Sulfamic 2-(4-methylphenoxy)ethyl ester a. Sulfamoyl chloride solution was prepared as in Example 4 using 40 ml (0.450 mole) of chlorosulfonyl isocyanate, 8.0 g (0.444 mole) of water and 150 ml of acetonitrile.

b. The title compound was obtained using the following procedure: The sulfamoyl chloride in acetonitrile solution prepared in (a), 17.0 g (0.112 mole) of 4-methylphenoxyethanol, 51.0 g (0.505 mole) of triethylamine in 100 ml of acetonitrile were reacted as in Example 4 followed by extraction, washing and concentration procedures of that example through the first evaporation step. The viscous oil obtained was partitioned between water and ethyl ether (400 ml each). The layers were separated and the organic layer was washed with four 300 ml portions of water (pH neutral to pH paper), dried over magnesium sulfate and the solvent was evaporated under reduced pressure to give a solid residue. The solid was recrystallized from ethyl ether-petroleum ether (bp range 30°–60° C.) to give 15.6 g (60%) of title compound as an off-white solid, mp 108.5°–110° C.

Analysis: Calculated for $C_9H_{13}NO_4S$: C, 46.74; H, 5.67; N, 6.06. Found: C, 47.06; H, 5.76; N, 6.12.

EXAMPLE 17

Sulfamic 2-(2-methoxyphenoxy)ethyl ester

The title compound was prepared by procedures of Example 16 from sulfamoyl chloride and 2-(2-methylphenoxy)ethanol in 53% yield as an off-white solid, mp 81.5°–83° C.

Analysis: Calculated for $C_9H_{13}NO_4S$: C, 46.74; H, 5.67; N, 6.06. Found: C, 46.91; H, 5.75; N, 6.32.

EXAMPLE 18

Sulfamic acid 4-phenoxybutyl ester

The title compound was prepared by procedures of Example 16 from sulfamoyl chloride and 4-phenoxy-1-butanol in 54% yield as an off-white solid, mp 76°–77° C.

Analysis: Calculated for $C_{10}H_{15}NO_4S$: C, 48.97; H, 6.16; N, 5.71. Found: C, 49.08; H, 6.26; N, 5.79.

EXAMPLE 19

Sulfamic acid 2-(4-methoxyphenoxy)ethyl ester

The title compound was prepared by procedures of Example 16 from sulfamoyl chloride and 2-(4-methoxyphenoxy)ethanol in 54% yield as an off-white solid, mp 84°–87° C.

Analysis: Calculated for $C_9H_{13}NO_5S$: C, 43.72; H, 5.30; N, 5.66 Found: C, 44.20; H, 5.38; N, 5.70

EXAMPLE 20

Sulfamic acid 2-(phenylmethoxy)ethyl ester

The title compound was prepared by procedures of Example 16 from sulfamoyl chloride and 2-(benzyloxy)ethanol except the oil obtained was then further purified by high pressure chromatography as described in earlier examples using methylene chloride as the eluting agent. Fractions containing the title compound were combined and the solvent was evaporated under reduced pressure to give title compound in 54% yield as light-yellow, viscous oil.

Analysis: Calculated for $C_9H_{13}NO_4S$: C, 46.74; H, 5.67; N, 6.06. Found: C, 46.48; H, 5.74; N, 6.03.

EXAMPLE 21

Sulfamic Acid Phenyl Ester

The compound was prepared by procedures of Example 16 from sulfamoyl chloride and phenol in 30% yield as white solid, mp 81°–85° C.

Analysis: Calculated for $C_6H_7NO_3S$: C, 41.61; H, 4.07; N, 8.09. Found: C, 41.63; H, 4.09; N, 8.07.

EXAMPLE 22

Sulfamic acid 2-(2-methoxyphenoxy)ethyl ester

The title compound was prepared by the procedure of Example 16 from sulfamoyl chloride and 2-(2-methoxyphenoxy)ethanol. The solid obtained was dissolved in 150 ml of methylene chloride, and the solution was treated with charcoal and filtered through Celite ®. The filtrate was evaporated under reduced pressure and the solid residue was recrystallized from methylene chloride-petroleum ether (30°–60° C.) to give the title compound in 25% yield as a white solid, mp 102°–104° C.

Analysis: Calculated for $C_9H_{13}NO_5S$: C, 43.72; H, 5.30; N, 5.66. Found: C, 43.72; H, 5.34; N, 5.63.

EXAMPLE 23

Sulfamic acid 2-phenoxypropyl ester

The title compound was prepared by procedures of Example 16 from sulfamoyl chloride and 2-phenoxypropanol. The oil obtained was further purified by chromatography (silica gel, eluted with methylene chloride) and recrystallization to give the title compound as a colorless, viscous oil in 35% yield.

Analysis: Calculated for $C_9H_{13}NO_4S$: C, 46.74; H, 5.67; N, 6.06. Found: C, 46.70; H, 5.73; N, 6.02.

EXAMPLE 24

Sulfamic acid 2-(4-chlorophenoxy)-2-methylpropyl ester

The title compound was prepared by procedures of Example 16 from sulfamoyl chloride and 2-(4-chlorophenoxy)-2-methylpropanol to give a white solid, mp 76°–79° C., in 58% yield.

Analysis: Calculated for $C_{10}H_{14}ClNO_4S$: C, 42.94; H, 5.04; N, 5.01. Found: C, 42.99; H, 5.13; N, 5.12.

EXAMPLE 25

Sulfamic acid 2-(3-chlorophenoxy)ethyl ester

The title compound was prepared by procedures of Example 16 from sulfamoyl chloride and 2-(3-chlorophenoxy)ethanol. The oil obtained was further purified by column chromatography and recrystallization from ethyl ether-petroleum ether (30°–60° C.) to give a white solid, mp 66°–69° C., in 44% yield.

Analysis: Calculated for $C_8H_{10}ClNO_4S$: C, 38.18; H, 4.01; N, 5.57. Found: C, 38.25; H, 4.03; N, 5.61.

EXAMPLE 26

Sulfamic acid 2-(4-bromophenoxy)ethyl ester

The title compound was prepared by the procedures of Example 16 from sulfamoyl chloride and 2-(4-bromophenoxy)ethanol as a white solid, mp 134°–137° C., in 69% yield.

Analysis: Calculated for $C_8H_{10}BrNO_4S$: C, 32.45; H, 3.40; N, 4.73. Found: C, 32.71; H, 3.47; N, 4.71.

EXAMPLE 27

Sulfamic acid 2-(2,4-dichlorophenoxy)ethyl ester

The title compound was prepared by the procedures of Example 16 from sulfamoyl chloride and 2-(2,4-dichlorophenoxy)ethanol. The viscous oil obtained solidified and was recrystallized from isopropyl ether to give the solid title compound, mp 75°–77° C., in 35% yield.

An additional 6.9 g of title compound was recovered from the mother liquor to bring the total yield to 60%.

Analysis: Calculated for $C_8H_9Cl_2NO_4S$: C, 33.58; H, 3.17; N, 4.90. Found: C, 33.65; H, 3.16; N, 5.00.

EXAMPLE 28

Sulfamic acid 2-(3,4-dichlorophenoxy)ethyl ester

The title compound was prepared by the procedures of Example 16 from sulfamoyl chloride and to 2-(3,4-dichlorophenoxy)ethanol. The tan colored solid obtained was dissolved in isopropyl ether and the solution treated with charcoal and filtered through Celite ®. The filtrate was evaporated under reduced pressure and the solid residue was recrystallized from isopropyl ether to give the title compound, mp 84°–85° C., in 19% yield.

Analysis: Calculated for $C_8H_9Cl_2NO_4S$: C, 33.58; H, 3.17; N, 4.90. Found: C, 33.76; H, 3.19; N, 4.92.

EXAMPLE 29

Methylsulfamic acid 2-(4-chlorophenoxy)ethyl ester

To a stirred solution of 45.0 g (0.347 mole) of methylsulfamoyl chloride (Example 2, pt. a) in 100 ml of methylene chloride was added in a thin stream a solution of 25.0 g (0.145 mole) of 2-(4-chlorophenoxy)ethanol (Lancaster Synthesis, Inc., Windham, N. H. 03087) in 30 ml (0.369 mole) of pyridine and 100 ml of methylene chloride and the reaction mixture was stirred at ambient temperature for 3 days. The solids were removed by filtration and the filtrate was evaporated under reduced pressure to yield a brown, viscous residue. The residue was partitioned between water and ethyl ether (400 ml each). The organic layer was washed twice with 300 ml portions of water, dried over magnesium sulfate and the solvent evaporated under reduced pressure to yield a solid residue. The solid was triturated with 100 ml of isopropyl ether and the solid was recollected by filtration. The solid was recrystallized from isopropyl ether to give 12.9 g (34%) of title compound as a white solid, mp 101°–104° C.

Analysis: Calculated for $C_9H_{12}ClNO_4S$: C, 40.68; H, 4.55; N, 5.27. Found: C, 40.78; H, 4.62; N, 5.25.

EXAMPLE 30

Sulfamic acid 3-phenoxybutyl ester

The title compound was prepared by procedures of Example 16 from sulfamoyl chloride and 3-phenoxy-1-butanol. The viscous oil obtained was purified by high pressure chromatography using a Waters Associates Prep LC/System 500A; PrepPAK 500 ® silica and methylene chloride as eluting agent at a flow rate of 200 ml/min. Fractions containing the title compound were combined and the solvent was evaporated under reduced pressure to give 12.7 g (67%) of title compound as a yellow, viscous oil.

Analysis: Calculated for $C_{10}H_{15}NO_4S$: C, 48.97; H, 6.16; N, 5.71. Found: C, 47.70; H, 6.22; N, 5.52.

Analysis: Calculated for $C_{10}H_{15}NO_4S.0.1CH_2Cl_2$: C, 47.80; H, 6.04; N, 5.52.

EXAMPLE 31

Dimethylsulfamic acid 2-(4-chlorophenoxy)ethyl ester

A solution of 25.0 g (0.145 mole) of 2-(4-chlorophenoxy)ethanol (Lancaster Synthesis Inc., Windham, N. H. 03087) in 64.6 g (0.640 mole) of triethylamine and 40 ml of methylene chloride was added in a thin stream to a solution of 83.3 g (0.580 mole) of dimethylsulfamoyl chloride (Aldrich) in 60 ml of methylene chloride stirred at ambient temperature in a water bath. The reaction mixture was stirred for 8 days at ambient temperature. The solids were removed by filtration and the filtrate was evaporated under reduced pressure to yield a viscous residue. The residue was partitioned between water and ethyl ether (300 ml each). The organic layer was washed with two 200 ml portions of 2N hydrochloric acid, once with 200 ml of water, dried over magnesium sulfate and the solvent evaporated under reduced pressure to yield a viscous residue. The residue was treated with 65.0 g (0.63 mole) of triethylamine and the reaction mixture was stirred for 5 days at ambient temperature. The solids were removed by filtration, the filtrate was evaporated under reduced pressure, and the viscous residue was partitioned between water and ethyl ether (450 ml each). The organic layer was washed with four 300 ml portions of water (pH neutral to pH paper), dried over magnesium sulfate and the solvent evaporated under reduced pressure to yield a brown, viscous, oily residue. The oil was purified by chromatography (4.5×90 cm glass column; 500 g of silica gel; methylene chloride). Fractions containing the title compound were combined and the solvent evaporated under reduced pressure to yield a viscous oil. The oil was dissolved in 150 ml of isopropyl ether and filtered to remove some insolubles. The filtrate was concentrated to a viscous oil. The oil was triturated with isopropyl ether-petroleum ether (bp range 30°–60° C.), cooled (refrigerator) and the resulting solid was collected by filtration. The solid was recrystallized from isopropyl ether to give 18.5 g (45%) of white solid, mp 54°–57° C.

Analysis: Calculated for $C_{10}H_{14}ClNO_4S$: C, 42.94; H, 5.04; N, 5.01. Found: C, 43.20; H, 5.11; N, 4.94.

EXAMPLE 32

Sulfamic acid 2-methyl-2-phenoxypropyl ester

This compound was prepared by the procedure used to synthesize 2-(4-methylphenoxy)ethanol sulfamate in Example 16. Thus, 13.2 g (0.0794 mole) of 2-methyl-2-phenoxypropanol was reacted with sulfamoyl chloride prepared from 26.5 ml (0.298 mole) of chlorosulfonyl isocyanate (98%, Aldrich), 33.9 g (0.336 mole) of triethylamine, and 5.3 g (0.294 mole) of water in 250 ml of acetonitrile. The 12.4 g of a viscous, oily residue obtained was purified by high pressure liquid chromatography (Waters Associates Prep LC/System 500A; Prep-PAK 500 ® silica; methylene chloride), then by chromatography (4.5×90 cm glass column; 500 g of silica gel; methylene chloride). Fractions containing title compound were combined and the solvent was evaporated under reduced pressure to give 5.4 (28%) of a viscous oil.

Analysis: Calculated for C$_{10}$H$_{15}$NO$_4$S: C, 48.97; H, 6.16; N, 5.71. Found: C, 48.11; H, 6.18; N, 5.58.

EXAMPLE 33

Dimethylsulfamic acid 3-(2-methoxyphenoxy)-1,2-propanediyl ester

A mixture of 19.8 g (0.1 mole) of glyceryl guaiacolate, 114.9 g (0.8 mole) of dimethylsulfamoyl chloride (Aldrich) and 89.2 g (0.88 mole) of triethylamine was stirred at ambient temperature for 5 days. To this mixture was added an additional 58 g (0.4 mole) of dimethylsulfamoyl chloride (Aldrich) and 45 g (0.45 mole) of triethylamine and the mixture was stirred at ambient temperature for 2 days, treated with water and ethyl acetate (400 ml each). The layers were separated and the organic layer was washed with six 300 ml portions of water, dried over magnesium sulfate and the solvent evaporated under reduced pressure to yield a viscous oil. The oil was purified by chromatography (4.5×90 cm glass column; 500 g of silica gel; methylene chloride). Fractions containing title compound were combined and the solvent was evaporated under reduced pressure to give 10.3 g (25%) of an oil that solidified upon standing. The solid was recrystallized from methylene chloride-ethyl ether to give 9.6 g (23%) of white solid, mp 78°–81° C.

Analysis: Calculated for C$_{14}$H$_{24}$N$_2$O$_8$S$_2$: C, 40.77; H, 5.87; N, 6.79. Found: C, 40.75; H, 5.98; N, 6.58.

EXAMPLE 34

Sulfamic acid 4-chlorophenyl ester

In one portion, 96 g (0.75 mole) of 4-chlorophenol was added to a stirred solution of 67.5 ml (0.75 mole) of chlorosulfonylisocyanate in 400 ml of toluene. The solution was heated at 100° C. for 16 hr and the solution chilled with an ice-acetone bath and water added dropwise until evolution of gases ceased. The tan solid which precipitated from solution was collected and dried for 16 hr to yield 133.4 g. A 25 g portion was recrystallized from 100 ml of toluene to give 15.8 g of white solid, mp 103°–104° C.

Analysis: Calculated for C$_6$H$_6$ClNO$_3$S: C, 34.71; H, 2.91; N, 6.75. Found: C, 34.73; H, 2.92; N, 6.74.

EXAMPLE 35

Sulfamic acid 3-chlorophenyl ester

By the procedure of Example 34, 96 g (0.75 mole) of 3-chlorophenol and 67.5 ml (0.75 mole) of chlorosulfonyl isocyanate gave 122.9 g of solid product. A 25 g portion was recrystallized from 100 ml of toluene to give 11.8 g of white solid, mp 82°–83° C.

Analysis: Calculated for C$_6$H$_6$ClNO$_3$S: C, 34.71; H, 2.91; N, 6.75. Found: C, 34.69; H, 2.90; N, 6.74.

EXAMPLE 36

Methylsulfamic acid 2[[(aminosulfonyl)oxy]methyl]-2-(3-methoxyphenoxy)ethyl ester A mixture of 8.0 g (0.0288 mole) of 3-(2-methoxyphenoxy)-2-hydroxypropanol sulfamate ester, 9.3 g (0.0721 mole) of methylsulfamoyl chloride and 7.3 g (0.0723 mole) of triethylamine was stirred at ambient temperature for 72 hr, treated with methylene chloride and water (150 ml each), and stirred vigorously for 10 min. The layers were separated and the organic layer was washed with four 150 ml portions of water, dried (over magnesium sulfate) and the solvent was evaporated under reduced pressure to yield a brown, viscous oil. The oil was purified by high pressure liquid chromatography (Waters Associates Prep LC 500A System: PrepPak 500 ® silica; methylene chloride-acetone; 9:1; flow rate: 100 ml/min). Fractions containing the title compound were combined and the solvents were evaporated under reduced pressure to give 2.2 g of a dark, viscous oil. The oil was dissolved in 100 ml of methylene chloride, treated with charcoal and filtered. The filtrate was evaporated under reduced pressure to give 2.1 g (20%) of title compound as a yellow gum.

Analysis: Calculated for C$_{11}$H$_{18}$N$_2$O$_8$S$_2$: C, 35.67; H, 4.90; N, 7.56. Found: C, 35.04; H, 4.95; N, 7.32.

EXAMPLE 37

Methylsulfamic acid phenyl ester

The reaction flask was charged with 34.1 g (0.20 mole) of methylaminosulfonyl chloride, 18.8 g (0.20 mole) of phenol and 150 ml of toluene. The dark, red solution was heated at 110° C. for 16 hours. The solution was cooled and washed with a solution of 16 g of sodium bicarbonate in 80 ml water. The toluene solution was washed with water then stirred with Type 3A molecular sieve powder and Norite "A" activated charcoal. After filtration, the filtrate was concentrated to 32.7 g of oil (87% crude yield). The oil was dissolved in 100 ml methylene chloride and chromatographed on silica gel. The main fraction was concentrated to an oil which solidified after chilling for 3 days. The solid was triturated with petroleum ether to give 16.1 g of solid, mp 43°–45° C. A recrystallization from a mixture of isopropyl acetate (2 ml/g) and petroleum ether (4 ml/g) gave 12.3 g of solid, mp 44°–46° C.

Analysis: Calculated for C$_7$H$_9$NO$_3$S: C, 44.91; H, 4.85; N, 7.48. Found: C, 44.84; H, 4.87; N, 7.47.

EXAMPLE 38

Sulfamic acid 4-(acetylamino)phenyl ester

A reaction flask was charged with 43.8 g (0.252 mole) of sulfamic acid phenyl ester; 12.6 g (0.084 mole) of 4-acetamidophenol, 9 ml of pyridine and 150 ml p-dioxane. The solution was heated at 75° C. for 18 hours. The solution was concentrated to a brown oil. The oil was partitioned between 100 ml of methylene chloride and 100 ml of 1.0N sodium bicarbonate. The mixture was refrigerated overnight then filtered to collect 15.8 g of white solid. $^1$H NMR spectrum indicated pure organic product but contaminated with sodium bicarbonate. The solid was added to 100 ml H$_2$O and the mixture stirred for one hour. The solid was collected and dried to give 8.4 g of solid, mp 180°–181° C.

Analysis: Calculated for C$_8$H$_{10}$N$_2$O$_4$S: C, 41.73; H, 4.38; N, 12.17. Found: C, 41.72; H, 4.42; N, 11.99.

EXAMPLE 39

Methylsulfamic acid 2-hydroxy-3-(2-methoxyphenoxy)propyl ester

A solution of 26.5 g (0.13 mole) of glycerol guaiacolate in 100 ml of methylene chloride and 10.8 ml (0.13 mole) of pyridine was added in a thin stream to a stirred solution of 17.1 g (0.13 mole) of N-methylsulfamoyl chloride in 70 ml of methylene chloride, and the reaction mixture was stirred at ambient temperature for 2 hr. The reaction mixture was treated with 150 ml of water, the layers were separated, and the organic layer was washed successively with a 200 ml portion of 2N hydrochloric acid solution, four 200 ml portions of water, dried (magnesium sulfate), and the solvent was evaporated under reduced pressure to yield a viscous oil. The oil was purified by preparative high pressure liquid chromatography. Fractions containing the desired product were combined and the solvents evaporated under reduced pressure to give 13.9 g (37%) of the title compound as a yellow gum.

Analysis: Calculated for $C_{11}H_{17}NO_6S$: C, 45.35; H, 5.88; N, 4.81. Found: C, 44.99; H, 5.95; N, 4.78.

EXAMPLE 40

Sulfamic acid 2-hydroxy-3-(2-methoxyphenoxy)propyl ester

To a cold solution (5° C.) of 19.2 ml (0.22 mole) of chlorosulfonyl isocyanate in 180 ml of acetonitrile was added 23.8 g (0.22 mole) of benzyl alcohol (reaction mixture temperature, 5°-8° C.). To this reaction mixture was added a solution of 39.6 g (0.2 mole) of glyceryl guaiacolate and 23.2 g (0.23 mole) of triethylamine in 180 ml of acetonitrile (reaction temperature, 5°-12° C.). The reaction mixture was stirred for 3 hr, and the solids were removed by filtration. The filtrate was stirred with 1.5 g of 5% Pd-C for 1 hr, filtered, and the filtrate was divided into two equal fractions. Each fraction was stirred with 1.5 g of 5% Pd-C and hydrogenated. The catalyst was removed by filtration, and the filtrates were concentrated under under reduced pressure to give 45 g and 42.3 g respectively. $^{13}C$ NMR showed the fractions to be identical. The two fractions were combined and were purified by chromatography (4.5×90 cm glass column; 550 g of silica gel; methylene chloride-acetone, 5:1). Fractions containing the desired component were combined and the solvents evaporated under reduced pressure to give 13.8 g of a viscous oil. The oil was triturated with methylene chloride and insolubles were removed by filtration. The filtrate was evaporated under reduced pressure to give 12.9 g of a viscous oil. A 4.0 g sample of this oil was purified by high pressure liquid chromatography (Waters Associates Prep LC/System 500A; PrepPAK 500 ® silica; methylene chloride-acetone, 10:1; flow rate 200 ml/min). Fractions containing the desired component were combined, and the solvents evaporated under reduced pressure to give 2.3 g (58% recovery) of the title compound as a brown gum containing a trace of methylene chloride.

Analysis: Calculated for $C_{10}H_{15}NO_6S$: C, 43.32; H, 5.45; N, 5.05. Found: C, 42.60; H, 5.48; N, 4.96.

Analysis: Calculated for $C_{10}H_{15}NO_6S \cdot 0.04CH_2Cl_2$: C, 42.96; H, 5.42; N, 4.99.

EXAMPLE 41

Methylsulfamic acid 2-[(aminosulfonyl)oxy]-3-(2-methoxyphenoxy) propyl ester

To a cold solution (ice-acetone bath) of 14.7 ml (0.166 mole) of chlorosulfonyl isocyanate (98%; Aldrich) in 100 ml of acetonitrile was added dropwise a solution of 2.7 g (0.15 mole) of water in 5 ml of acetonitrile such that the reaction mixture temperature was maintained at ≦7° C. The mixture was stirred vigorously for 10 min, and to it was added a solution of 12.3 g (0.042 mole) of 3-(2-methoxyphenoxy)-1,2-propanediol methyl sulfamate ester (Example 40) and 17.0 g (0.168 mol) of triethylamine in 100 ml of acetonitrile at such a rate that the temperature of the reaction mixture was maintained at ≦12° C. The reaction mixture was stirred vigorously for 3 hr at ambient temperature and treated with 100 ml of water and 200 ml of ethyl acetate. The layers were separated, and the organic layer was washed with 200 ml of water and evaporated under reduced pressure to yield a viscous residue. The residue was partitioned between 200 ml of water and 300 ml of ethyl ether. The organic layer was washed with three 200 ml portions of water (pH neutral to pH paper), dried over magnesium sulfate and the solvent evaporated under reduced pressure to give 8.5 g (55%) of a viscous, oily residue which solidified upon standing. The solid was triturated with 75 ml of methylene chloride and the precipitate was collected by filtration to yield 4.2 g (27%) of the title compound as a white solid, mp 110°-113° C.

Analysis: Calculated for $C_{11}H_{18}N_2O_8S_2$: C, 35.67; H, 4.90; N, 7.56. Found: C, 35.54; H, 4.96; N, 7.54.

EXAMPLE 42

Sulfamic acid 2-(8-quinolinyloxy)ethyl ester monohydrochloride

Using the procedure of Example 4, 5.4 g (0.029 mole) of 2-(8-quinolinyloxy)ethanol was reacted with sulfamoyl chloride. During work-up of the reaction, a light-yellow material deposited out from the organic-aqueous system. $^1H$ NMR of this material suggested that it might be a quaternary salt. The oily product obtained at the end of the work-up procedure weighed 2.7 g. This oil was dissolved in acetonitrile-isopropyl alcohol and acidified with 37% hydrochloric acid. The mixture was evaporated to almost dryness and then redissolved in methanol. To the solution was added ethyl acetate and most of the methanol was evaporated carefully. The light-yellow solid was collected and dried at 40° C. in vacuum overnight to give 2.4 g solid, mp 138°-140° C.

Analysis: Calculated for $C_{11}H_{12}N_2O_4S \cdot HCl$: C, 43.35; H, 4.30; N, 9.19. Found: C, 43.26; H, 4.38; N, 9.04.

EXAMPLE 43

Methylsulfamic acid 4-chlorophenyl ester

A solution of 18.1 g (0.14 mole) of N-methylsulfamoyl chloride (Example 2, pt. a) in 20 ml methylene chloride was added at 10°-20° C. to a solution of 12.8 g (0.10 mole) of 4-chlorophenol and 15 g (0.15 mole) of triethylamine in 50 ml of methylene chloride. The cooling was removed and the mixture stirred at ambient temperature for four hours. The mixture was filtered to remove the triethylamine hydrochloride. The filtrate was extracted with dilute HCl (6 ml of 37% hydrochloric acid in 60 ml water) followed by a water wash. The organic layer was then extracted with dilute potassium carbonate (8.0 g in 80 ml water) followed by a water wash. The methylene chloride layer was concentrated to 21.7 g of yellow oil which crystallized on cooling. The solid was stirred in a mixture of 10 ml toluene and 63 ml petroleum ether to obtain 20.3 g of yellow solid. The 20.3 g was recrystallized from 1:2 toluene: petroleum ether to give 8.73 g of white solid, mp 61°-62° C.

Analysis: Calculated for $C_7H_8ClNO_3S$: C, 37.93; H, 3.64; N, 6.32. Found: C, 37.59; H, 3.69; N, 6.42.

EXAMPLE 44

Ethylsulfamic acid 3-(2-methoxyphenoxy)propyl ester

A solution of 19.8 g (0.1 mole) of glyceryl guaiacolate in 100 ml of methylene chloride and 21.6 ml (0.26 mole) of pyridine was added in a thin stream to a stirred solution of 37.3 g (0.26 mole) of ethylsulfamoyl chloride (prepared using procedure of Example 2, pt. a) in 150 ml of methylene chloride, and the reaction mixture was stirred at ambient temperature overnight. The reaction mixture was treated with 150 ml of 2N hydrochloric acid solution, and the layers were separated. The organic layer was washed with 150 ml of 2N hydrochloric acid solution, twice with 150 ml portions of water, dried (magnesium sulfate), and the solvent was evaporated under reduced pressure. The residue was purified by chromatography (4.5×90 cm glass column; 500 g of silica gel; methylene chloride-acetone, 25:1). Fractions containing the product were combined, and the solvents wre evaporated under reduced pressure to give 20.2 g (49%) of the title compound as a light-yellow, viscous oil containing a trace of methylene chloride.

Analysis: Calculated for $C_{14}H_{24}N_2O_8S_2$: C, 40.77; H, 5.86; N, 6.79. Found: C, 40.21; H, 5.94; N, 6.77.

Analysis: Calc. for $C_{14}H_{24}N_2O_8S_2 \cdot 0.03CH_2Cl_2$: C, 40.60; H, 5.84; N, 6.75.

EXAMPLE 45

Ethylsulfamic acid 3-phenoxy-1,2-propanediyl ester

This compound was prepared by the procedure used in Example 44. Thus, 17.7 g (0.1 mole) of 3-phenoxy-1,2-propanediol (95%, Aldrich), 37.3 g (0.26 mole) of ethylsulfamoyl chloride, and 21.6 ml (0.26 mole) of pyridine in 250 ml of methylene chloride gave 37.5 g of a yellow, viscous residue which solidified upon standing. The solid was recrystallized from ethyl ether-petroleum ether (30°–60° C.) to give 23.3 g (61%) of the title compound as a white solid, mp 60°–63° C.

Analysis: Calculated for $C_{13}H_{22}N_2O_7S_2$: C, 40.83; H, 5.80; N, 7.33. Found: C, 40.59; H, 5.93; N, 7.30.

EXAMPLE 46

Sulfamic acid 2-(3-pyridinyloxy)ethyl ester hydrochloride

A mixture of 4.9 g (0.035 mole) of 2-(3-pyridinyloxy)ethanol[prepared as an oil by procedure of Preparation 21 from 14 g (0.15 mole) of 3-hydroxypyridine, 27 ml (0.40 mole) of 2-chloroethanol and 85 g of potassium carbonate] and 8 g (0.046 mole) of sulfamic acid phenyl ester in 100 ml of dioxane was heated at reflux temperatue for 20 min and the solvent then evaporated. The residue was triturated with 250 ml of acetone, filtered, and the filtrate acidified with a solution of anhydrous hydrogen chloride in isopropyl alcohol and the sticky, brown precipitate collected. The brown solid was redissolved in 125 ml of methanol and diluted with 125 ml of ethanol. The solution was stirred with charcoal, filtered, and the filtrate partially evaporated to give a suspension. The suspension was diluted with isopropyl alcohol-isopropyl ether and filtered. The solid was dried at 50° C. for 18 hr and then at 70° C. for 18 hr in a vacuum oven. The yield was 4.5 g of solid, mp 156°–157° C.

Analysis: Calculated for $C_7H_{10}N_2O_4S \cdot HCl$: C, 33.01; H, 4.35; N, 11.00. Found: C, 33.51; H, 4.55; N, 10.43.

EXAMPLE 47

Sulfamic acid 2-[4-(1H-imidazol-1-yl)phenoxy]ethyl ester hydrochloride

A stirred mixture of 8.0 g (0.050 mole) of 4-(1H-imidazol-1-yl)phenol, 13.5 ml (0.20 mole) of 2-chloroethanol and 28 g (0.2 mole) of potassium carbonate in 200 ml of methyl ethyl ketone was heated at reflux, filtered, and concentrated to obtain 5.1 g of 2-[4-(1H-imidazol-1-yl)phenoxy]ethanol (50%). This alcohol (0.25 mole) and 5.2 g (0.030 mole) of sulfamic acid phenyl ester in 100 ml of dioxane was heated at reflux for 20 minutes, concentrated and the residual solid triturated in acetone. The triturant was acidified with an anhydrous solution of hydrogen chloride in isopropyl alcohol and the solid hydrochloride collected by filtration. The product was recrystallized from isopropyl alcohol-isopropyl ether to yield 4.26 g of solid, mp 156°–157° C.

Analysis: Calculated for $C_{11}H_{13}N_3O_4S \cdot HCl$: C, 41.32; H, 4.41; N, 13.14. Found: C, 41.60; H, 4.62; N, 12.87.

EXAMPLE 48

(1-Methylethyl)sulfamic acid 3-phenoxy-1,2-propanediyl ester

This compound was prepared according to the procedure of Example 44. Thus 19.5 g (0.11 mole) of 3-phenoxy-1,2-propanediol, 63.0 g (0.26 mole) of 2-propylsulfamoyl chloride and 21.6 ml (0.26 mole) of pyridine in 250 ml of methylene chloride gave 63.9 g of a brown, viscous oil. The oil was purified by column chromatography on silica gel using methylene chloride-acetone (60:1) to elute the material. Desired fractions were combined and concentrated to yield a white solid. The solid was recrystallized from ethyl ether-petroleum ether (30°–60° C.) to yield 28.1 g (62%) of white solid, mp 77°–80° C.

Analysis: Calculated for $C_{15}H_{26}N_2O_7S_2$: C, 43.89; H, 6.38; N, 6.82. Found: C, 43.82; H, 6.52; N, 6.84.

EXAMPLE 49

(1,1-Dimethylethyl)sulfamic acid 3-phenoxy-1,2-propanediyl ester

This compound was prepared by the procedure used in Example 44. Thus, 13.7 g (0.077 mole) of 3-phenoxy-1,2-propanediol (95%, Aldrich), 31.3 g (0.18 mole) of N-(t-butylsulfamoyl) chloride (prepared by procedure of Example 2, part a from t-butylamine, sulfuryl chloride and antimony pentachloride) and 15.2 ml (0.18 mol) of pyridine in 250 ml of methylene chloride gave 30.8 g of a dark, viscous oil. The oil was purified by chromatography (4.5×90 cm glass column, 500 g of silica gel, methylene chloride-acetone, 80:1). Fractions containing the desired compound were combined and the solvents evaporated under reduced pressure to yield a viscous oil that solidified upon standing. The solid was recrystallized from ethyl ether-petroleum ether (30°–60° C.) to give 12.9 g (38%) of the title compound as a white solid, mp 101.5°–103° C.

Analysis: Calculated for $C_{17}H_{30}N_2O_7S_2$: C, 46.56; H, 6.90; N, 6.35. Found: C, 46.66; H, 7.05; N, 6.38.

EXAMPLE 50

Sulfamic acid 4-(methoxycarbonyl)phenyl ester

Chlorosulfonylisocyanate (8.8 ml, 0.1 mole) was added to 200 ml toluene. Solid methyl 4-hydroxybenzoate (15.2 g, 0.1 mole) was added to the stirred solution. The mixture was heated at reflux for 1.5 hr then cooled and treated with about 8 ml water and some tetrahydrofuran. Solvents were then removed by evaporation. The residue was triturated with ethyl acetate-isopropyl ether. The insoluble solid was removed by filtration. The filtrate was concentrated and then triturated in isopropyl ether. The solid was collected and weighed 8.6 g. Recrystallization from acetone-isopropyl ether gave a white solid which was dried under vacuum overnight at room temperature to 3.9 g, mp 116°–118° C.

Analysis: Calculated for $C_8H_9NO_5S$: C, 41.56; H, 3.92; N, 6.06. Found: C, 41.53; H, 3.97; N, 6.05.

EXAMPLE 51

Sulfamic acid 3-(methoxycarbonyl)phenyl ester

Following the procedure of Example 50, a reaction of 8.8 ml (0.10 mole) chlorosulfonyl isocyanate and 15.2 g (0.10 mole) of methyl 3-hydroxybenzoate in 200 ml of toluene was heated at reflux for 7.5 hr and worked up to obtain 10.53 g of solid, mp 145°-146° C.

Analysis: Calculated for $C_8H_9NO_5S$: C, 41.56; H, 3.92; N, 6.06. Found: C, 41.30; H, 3.94; N, 6.06.

EXAMPLE 52

Sulfamic acid 3-(2-amino-2-oxoethyl)phenyl ester

The title compound was prepared from m-acetamidophenol (12.10 g, 0.08 mole), reacting with the sulfamoyl chloride generated from water and chlorosulfonyl isocyanate. The crude product contained desired product and starting material. The product was isolated by chromatography on 100 g of silica gel, eluted first with 7:3 methylene chloride/acetonitrile and then increasing the proportion of acetonitrile in the eluting solvent. The main fraction was evaporated and triturated with isopropyl alcohol/isopropyl ether to give 4 g of white solid, recrystallized from acetonitrile/isopropyl ether, and dried in vacuum at 60° C. overnight to give 3.73 g of solid, mp 148°-149° C.

Analysis: Calculated for $C_8H_{10}N_2O_4S$: C, 41.73; H, 4.38; N, 12.17. Found: C, 42.06; H, 4.46; N, 12.35.

EXAMPLE 53

Sulfamic acid 4-carboxyphenyl ester

Benzyl 4-hydroxybenzoate (22.8 g, 0.1 mole) was converted to its benzyloxycarbonylsulfamoyl derivative by the same procedure as described in Example 50. This intermediate was isolated as an oil and was hydrogenated over 5% Pd-C by the same manner to give 4.5 g solid. Recrystallization from methanol-acetonitrile yielded 3 g of pure product, mp 184°-186° C.

Analysis: Calculated for $C_7H_7NO_5S$: C, 38.71; H, 3.25; N, 6.45. Found: C, 38.71; H, 3.32; N, 6.62.

EXAMPLE 54

Sulfamic acid 4-(1H-imidazol-1-yl)phenyl ester

To a chilled solution of chlorosulfonyl isocyanate (8.7 ml, 0.10 mole) in 50 ml of methylene chloride was added a solution of 10.8 g (0.10 mole) of benzyl alcohol in 200 ml of methylene chloride over a period of 6 minutes at 3°-15° C. The reaction was then stirred at ambient temperature for 2 hours and then chilled in an ice-water bath. To this solution was added 4-(imidazol-1-yl)phenol (12 g, 0.075 mole) as a solid, and the mixture was stirred at room temperature for 45 minutes. Triethylamine (14 ml, 0.1 mole) was then added to the suspension, and the reaction became a dark brown solution. The mixture was stirred for two days, and the solid was collected by filtration, stirred in water for half an hour, and filtered again, rinsed with isopropyl alcohol and isopropyl ether. This solid intermediate weighed 18.24 g (65%) and $^1$H NMR showed it exists as the zwitterion. The zwitterion (18 g) was added to a solution of isopropyl alcohol containing 0.05 mole hydrogen chloride and diluted with 100 ml methanol. The resultant solution was mixed with 1.8 g Pd-C (5%) and hydrogenated until there was no further absorption of hydrogen. The catalyst was removed, and the solution was concentrated to give 10 g solid. Part of the solid was recrystallized by dissolving in excess amount of methanol, filtering, and concentrating to crystallize about 5 g solid. The solid was dried in vacuum oven at 80° C. overnight, mp 198°-200° C.

Analysis: Calculated for $C_9H_9N_3O_3S \cdot HCl$: C, 39.21; H, 3.66; N, 15.24. Found: C, 39.07; H, 3.65; N, 15.15.

EXAMPLE 55

(1-Methylethyl)sulfamic acid phenyl ester

This compound was prepared according to the procedure of Example 37. Thus a solution of 16.2 g (0.17 mole) of phenol and 33.0 g (0.21 mole) of N-isopropylsulfamoyl chloride (prepared from isopropylamine, sulfuryl chloride and antimony pentachloride by the procedure of Example 2, part a) in 150 ml of toluene gave a dark oil which was purified by column chromatography on silica gel using ethyl acetate-hexanes (1:16) to elute the product. Desired fractions were combined and concentrated to yield 11.7 g (32%) of the title compound as a light-yellow oil.

Analysis: Calculated for $C_9H_{13}NO_3S$: C, 50.22; H, 6.09; N, 6.51. Found: C, 50.20; H, 6.23; N, 6.31.

EXAMPLE 56

Sulfamic acid (3,4-dichlorophenyl) ester

A solution of 16.3 g (0.1 mole) of 3,4-dichlorophenol in 100 ml of toluene was heated at reflux utilizing a Dean-Stark trap to remove any water that may have been present. The solution was cooled in an ice bath, treated with 9.1 ml (14.8 g, 0.105 mole) of chlorosulfonyl isocyanate, and heated at reflux overnight. The solution was cooled in an ice bath, vigorously stirred, and treated dropwise with water until gas evolution ceased. The solid which precipitated was collected by filtration, washed with water and benzene, dried, and recrystallized from benzene to yield 19.9 g (82%) of a white solid, mp 121°-123° C.

Analysis: Calculated for $C_6H_5Cl_2NO_3S$: C, 29.77; H, 2.08; N, 5.79. Found: C, 29.94; H, 2.10; N, 5.93.

EXAMPLE 57

Sulfamic acid (4-nitrophenyl ester)

This compound was prepared according to the procedure of Example 56. A mixture of 13.9 g (0.1 mole) of 4-nitrophenol and 14.8 g (0.105 mole) of chlorosulfonyl isocyanate in 100 ml of toluene gave 17.8 g (82%) of tan solid, mp 103°-111° C. (benzene-acetonitrile).

Analysis: Calculated for $C_6H_6N_2O_5S$: C, 33.03; H, 2.77; N, 12.84. Found: C, 33.29; H, 2.80; N, 12.85.

EXAMPLE 58

Ethylsulfamic Acid Phenyl Ester

A solution of 18.8 g (0.2 mole) of phenol and 38.4 g (0.27 mole) of ethylaminosulfonyl chloride (prepared using procedure of Example 2, pt. a) in 150 ml of toluene was stirred and heated at reflux for 16 hr. The solution was cooled and then treated with 250 ml of a 20% sodium bicarbonate solution. The layers were separated and the organic layer was washed successively with 250 ml of a 20% sodium bicarbonate solution, two 300-ml portions of water and dried (magnesium sulfate). The solvent was evaporated under reduced pressure and the oily residue was purified by chromatography (4.5 × 105 cm glass column; 550 g of silica gel; ethyl acetate-hexanes, 1:16). Fractions containing the product were combined and the solvents evaporated under reduced pressure to give 28.5 g (71%) of the title compound as a colorless liquid. Elemental analysis suggested that the product contained water.

Analysis: Calculated for $C_8H_{11}NO_3S.0.1H_2O$: C, 47.32; H, 5.56; N, 6.90. Found: C, 47.06; H, 5.69; N, 7.13.

EXAMPLE 59

Sulfamic acid 4-phenyl-1,2,5-thiadiazol-3-yl ester.

A slurry of 3-hydroxy-4-phenyl-1,2,5-thiadiazole (15.0 g, 0.084 mole) in acetonitrile (100 ml) was treated by the simultaneous dropwise addition of a sulfamoyl chloride solution in acetonitrile (0.20 mole, 66 ml of 3M) and a diisopropylethylamine solution (0.22 mole in enough 1:1 acetonitrile/methylene chloride to make 66 ml). High Pressure Liquid Chromatography analysis indicated a maximum of 85% conversion of starting material to product. The reaction was worked up by concentration of the reaction mixture and partitioning the residue between ethyl ether and water. Concentration of the ether fraction gave a white paste from which desired product was separated by dissolving in a small amount of acetonitrile. The product was crystallized from the acetonitrile to give 2.8 g (13%) of the title compound as a white powder, mp 128°-130° C.

Analysis: Calculated for $C_8H_7N_3O_3S_2$: C, 37.35; H, 2.74; N, 16.33. Found: C, 37.30; H, 2.75; N, 16.41.

EXAMPLE 60

Sulfamic acid 3-nitrophenyl ester

This compound was prepared according to the procedure used in Example 56. A mixture of 13.9 g (0.1 mole) of 3-nitrophenol and 14.8 g (0.105 mole) of chlorosulfonyl isocyanate in 100 ml of toluene gave 16.9 g (78%) of tan flakes, mp 118°-120° C.

Analysis: Calculated for $C_6H_6N_2O_5S$: C, 33.03; H, 2.77; N, 12.84. Found: C, 33.18; H, 2.81; N, 12.95.

EXAMPLE 61

Sulfamic acid 3-(trifluoromethyl)phenyl ester

This compound was prepared according to the procedure used in Example 56. A mixture of 18.4 g (0.114 mole) of $\alpha,\alpha,\alpha$-trifluoro-m-cresol, 14.8 g (0.105 mole) of chlorosulfonyl isocyanate and 100 ml of toluene gave 22.5 g (82%) of a white solid, mp 100°-102° C.

Analysis: Calculated for $C_7H_6F_3NO_3S$: C, 34.86; H, 2.51; N, 5.81. Found: C, 35.04; H, 2.48; N, 5.86.

EXAMPLE 62

Sulfamic acid (1,1'-biphenyl)-4-yl ester

This compound was prepared according to the procedure used in Example 56. A mixture of 17.0 g (0.1 mole) of 4-phenylphenol, 14.8 g (0.105 mole) of chlorosulfonyl isocyanate and 100 ml of toluene gave 17.2 g (69%) of white crystals, mp 166°-168° C. (benzene-acetonitrile).

Analysis: Calculated for $C_{12}H_{11}NO_3S$: C, 57.82; H, 4.45; N, 5.62. Found: C, 58.06; H, 4.47; N, 5.66.

EXAMPLE 63

Sulfamic acid 4-nitro-3-(trifluoromethyl)phenyl ester

This compound was prepared according to the procedure used in Example 56. A mixture of 10.4 g (0.05 mole) of 5-hydroxy-2-nitrobenzotrifluoride, 7.8 g (0.055 mole) of chlorosulfonyl isocyanate and 75 ml of toluene gave 11.1 g (78%) of tan solid, mp 95°-97° C. (benzene).

Analysis: Calculated for $C_7H_5F_3N_2O_5S$: C,29.38; H,1.76; N,9.79. Found: C,29.30; H,1.69; N,9.81.

EXAMPLE 64

Sulfamic acid 4-methyl-2-oxo-2H-1-benzopyran-7-yl ester

A slurry of 7-hydroxy-4-methylcoumarin (17.6 g, 0.10 mole) in acetonitrile (100 ml) was treated with a total of 84 ml of 3 M sulfamoyl chloride (0.255 mole) in acetonitrile. The mixture was then treated dropwise with triethylamine (25.8 g, 0.255 mole). The reaction temperature was allowed to rise to 45° C. without any cooling. The mixture was stirred overnight at ambient temperature. The precipitate was collected, triturated with water, and dried in a vacuum oven at 70° C. for 15 hr to give 10.5 g (41%) of white powder, mp 161°-164° C.

Analysis: Calculated for $C_{10}H_9NO_5S$: C, 47.06; H, 3.55; N, 5.49. Found: C, 47.08; H, 3.58; N, 5.56.

EXAMPLE 65

Sulfamic acid 2-chlorophenyl ester

This compound was prepared by the procedure used in Example 56. A mixture of 12.8 g (0.1 mole) of 2-chlorophenol, 14.8 g (0.105 mole) of chlorosulfonyl isocyanate and 75 ml of toluene gave 12.2 g (59%) of the title compound as a white solid, mp 62.5°-63.5° C. (cyclohexane-benzene).

Analysis: Calculated for $C_6H_6ClNO_3S$: C, 34.71; H, 2.91; N, 6.75. Found: C, 34.50; H, 2.92; N, 6.76.

EXAMPLE 66

Methylsulfamic acid 4-(1H-imidazol-1-yl)phenyl ester monohydrochloride

Triethylamine (11.2 ml, 0.08 mole) and 4-(imidazo-1-yl)phenol (9.6 g, 0.06 mole) were stirred in 100 ml methylene chloride as a suspension in an ice bath. To this suspension was added a solution of methylsulfamoyl chloride (10.8 g, 0.08 mole) in 10 ml methylene chloride over 4 minutes. The ice bath was then removed and the reaction was stirred at room temperature overnight. The grayish suspension slowly changed to a tan suspension. The solid was filtered and rinsed with methylene chloride and then dissolved in 300 ml methanol. The solution was acidified with HCl/isopropyl alcohol and stirred with charcoal. The almost colorless filtrate was mixed with some isopropyl alcohol and then concentrated. The residual solid was triturated in isopropyl alcohol/isopropyl ether, collected by filtration, and dried overnight at 80° C. in a vacuum oven to yield 11.34 g of solid, mp 221°-223° C.

Analysis: Calculated for $C_{10}H_{11}N_3O_3S.HCl$: C, 41.46; H, 4.18; N, 14.50. Found: C, 41.40; H, 4.21; N, 14.38.

EXAMPLE 67

Sulfamic acid (2-naphthalenyl) ester

To a cold (ice-acetone bath) solution of 11.3 ml (0.13 mole, 18.4 g) of chlorosulfonyl isocyanate in 50 ml of acetonitrile was added dropwise a solution of 2.3 g (0.13 mole) of water in 10 ml of acetonitrile at such a rate that the temperature was maintained between $-2°$ to 7° C. (ca. 45 min). After the addition was complete, the solution was stirred for 5 min and then treated dropwise with a solution of 14.4 g (0.1 mole) of $\beta$-naphthol, 20.9 ml (0.15 mole, 15.2 g) of triethylamine and 100 ml of acetonitrile at such a rate that the temperature did not exceed 10° C. (ca. 30 min). The mixture was stirred at ambient temperature for 3.5 h and then diluted with 100 ml of ethyl acetate and 50 ml of water. The layers were separated and the organic layer was washed once with 50 ml of water and once with 100 ml of brine, dried (sodium sulfate), and concentrated to give 24 g of dark gum. The gum was purified by column chromatography on 400 g of silica gel eluted with methylene chloride. Fractions containing the desired product were combined and concentrated to yield 5.7 g (26%) of the title compound as a white solid, mp 114°–115° C. (benzene).

Analysis: Calculated for $C_{10}H_9NO_3S$: C, 53.80; H, 4.06; N, 6.27. Found: C, 53.83; H, 4.02; N, 6.25.

EXAMPLE 68

Methylsulfamic acid 3-phenoxy-1,2-propanediyl ester

To a vigorously stirred solution of 17.7 g (0.1 mole) of 3-phenoxy-1,2-propanediol in 250 ml of methylene chloride was added simultaneously, over a 30 min period, 35.8 g (0.28 mole) of methylaminosulfonyl chloride and 36.0 g (0.28 mole) of diisopropylethylamine. The dark reaction mixture was stirred for 3 hr and the solvent was evaporated under reduced pressure to yield a brown, viscous oil. The oil was partitioned between ethyl acetate and a 2N hydrochloric acid solution (250 ml each). The organic layer was further washed with two 250-ml portions of 2N hydrochloric acid solution, 250 ml of water, and dried (magnesium sulfate). The solvent was evaporated under reduced pressure and the viscous, oily residue was purified by chromatography (4.5×105 cm glass column; 520 g of silica gel; methylene chloride-acetone, 100:3). Fractions containing the product were combined and the solvents evaporated under reduced pressure to give 25.7 g (73%) of the title compound as a pale-yellow gum.

Analysis: Calculated for $C_{11}H_{18}N_2O_7S_2$: C, 37.28; H, 5.12; N, 7.90. Found: C, 36.75; H, 5.17; N, 7.83.

EXAMPLE 69

Sulfamic acid 4-(2H-1,2,4-triazol-2-yl)phenyl ester hydrochloride (2:1)

4-(1H-1,2,4-triazol-1-yl)phenol (5.0 g, 0.031 mole) was suspended in methylene chloride (30 ml) and sulfamoyl chloride (7.13 g, 0.062 mole) added to the stirring mixture. Triethylamine (6.27 g, 0.062 mole) was added dropwise while maintaining the temperature between 25°–30° C. After the addition was complete the reaction was stirred for several hours at room temperature. HPLC analysis indicated the reaction had not gone to completion. The reaction was treated with an additional 0.031 mole of sulfamoyl chloride and triethylamine. The reaction stirred overnight at room temperature and was worked up after $^1$H NMR indicated reaction had gone to completion. The solvent was evaporated and the residue partitioned between ethyl acetate/acetonitrile (1:1)/aqueous sodium hydroxide, sodium bicarbonate (1:1). The organic layer was evaporated and the base isolated as an off-white powder (4.78 g, 64%). The crystals were dissolved in hot isopropyl alcohol, the solution cooled and the mixture filtered. The filtrate containing the base was evaporated to a residue, dissolved in methanol and a solution of anhydrous HCl/isopropyl alcohol added. White crystals precipitated out of solution as more isopropyl alcohol was added and methanol removed. The crystals were filtered, dried and analyzed (0.80 g, 0.0029 mole, 9%, mp 169°–173° C.).

Analysis: Calculated for $C_8H_8N_4O.0.5HCl$: C, 37.18; H, 3.32; N, 21.68. Found: C, 36.93; H, 3.30; N, 21.44.

EXAMPLE 70

Sulfamic acid 4-benzoylphenyl ester

This compound was prepared according to the procedure used in Example 56. A mixture of 9.9 g (0.05 mole) of 4-hydroxybenzophenone, 7.1 g (0.0505 mole) of chlorosulfonyl isocyanate and 75 ml of toluene gave 8.1 g (58%) of the title compound as off-white flakes, mp 131°–133° C.

Analysis: Calculated for $C_{13}H_{11}NO_4S$: C, 56.31; H, 4.00; N, 5.05. Found: C, 56.03; H, 3.92; N, 5.07.

EXAMPLE 71

Sulfamic acid 3-bromophenyl ester

This compound was prepared according to the procedure used in Example 56. A mixture of 17.3 g (0.1 mole) of 3-bromophenol, 9.1 ml (14.8 g, 0.105 mole) of chlorosulfonyl isocyanate and 100 ml of toluene gave 19.8 g (70%) of white solid, mp 90°–91.5° C. (benzene)

Analysis: Calculated for $C_6H_6BrNO_3S$: C, 28.59; H, 2.40; N, 5.56. Found: C, 28.35; H, 2.46; N, 5.52.

EXAMPLE 72

Sulfamic acid 4-(trifluoromethyl)phenyl ester

This compound was prepared according to the procedure used in Example 56. A mixture of 9.6 g (0.059 mole) of α,α,α-trifluoro-p-cresol, 5.7 ml (9.2 g, 0.065 mole) of chlorosulfonyl isocyanate and 75 ml of toluene gave 11.2 g (70%) of white solid, mp 111°–112° C. (benzene).

Analysis: Calculated for $C_7H_6F_3NO_3S$: C, 34.86; H, 2.51; N, 5.81. Found: C, 34.75; H, 2.47; N, 5.80.

EXAMPLE 73

Sulfamic acid 3-benzoylphenyl ester

This compound was prepared according to the procedure used in Example 56. A mixture of 9.9 g (0.05 mole) of 3-hydroxybenzophenone and 4.4 ml (7.1 g, 0.0505 mole) of chlorosulfonyl isocyanate in 75 ml of toluene gave a solid as residue. This residue was recrystallized sucessively from benzene and then methylene chloride to yield 4.2 g (30%) of the title compound as a white solid, mp 72°–74° C.

Analysis: Calculated for $C_{13}H_{11}NO_4S$: C, 56.31; H, 4.00; N, 5.05. Found: C,55.89; H,3.95; N,5.03.

EXAMPLE 74

Sulfamic acid 3-(dimethylamino)phenyl ester monohydrochloride

A solution of 3-dimethylaminophenol (6.90 g, 0.05 mole) in 30 ml of acetonitrile was added in 13 minutes to a chilled (15° C.) stirred solution of 0.10 mole sulfamoyl chloride in 30 ml of acetonitrile. This was followed by the addition of 14 ml (0.10 mole) of triethylamine. The resultant mixture was stirred at room temperature overnight. The reaction was diluted with ethyl acetate (~60 ml) and then extracted twice with sodium bicarbonate solution. The combined aqueous layers were back extracted with 1:1 ethyl acetate/acetonitrile once. The organic layers were combined, dried over sodium sulfate, treated with charcoal, filtered, and evaporated to a black oil weighing 7.57 g.

The above reaction was repeated doubling the scale and all the black oil combined and chromatographed on 360 g of silica gel eluting with 10% acetonitrile/methylene chloride. The fractions containing the desired product also contained some starting material. These fractions were combined, concentrated, and redissolved in isopropyl alcohol. The solution was acidified with a solution of anhydrous HCl in isopropyl alcohol and crystallized to give 9.39 g of a light-greenish-brown solid. This solid was redissolved in methanol (charcoal) to give a light-blue filtrate. Evaporation and crystallization of the residue from isopropyl alcohol gave 8.5 g of off-white solid, mp 168°–70° C.

Analysis: Calculated for $C_8H_{12}N_2O_3S \cdot HCl$: C, 38.02; H, 5.19; N, 11.09. Found: C, 38.05; H, 5.34; N, 11.11.

EXAMPLE 75

Methylsulfamic acid 2-[4-(1H-imidazol-1-yl)phenoxy]ethyl ester hydrochloride hydrate (2:2:1)

A solution of 4-imidazol-1-yl-phenol (20.0 g, 0.125 mole), 2-chloroethanol (40.25 g, 0.50 mole) and potassium carbonate (69.0 g, 0.50 mole) in 500 ml of methyl ethyl ketone was heated at reflux for 48 hr as its progress was being monitored by TLC (methanol:methylene chloride 10:90). The reaction was then filtered, and the filtrate evaporated to a solid which was redissolved in hot isopropanal. The crystals which formed upon cooling were filtered, rinsed with isopropyl ether, and dried (7.36 g, 28.9% yield, $^1$H NMR: 95% pure). This intermediate alcohol (6.0 g, 0.029 mole), suspended in methylene chloride (60 ml) and triethylamine (3.51 g, 0.0348 mole) was added to the stirring suspension. The reaction was chilled at 10° C. and methylsulfamoyl chloride (4.51 g, 0.0348 mole) was added dropwise allowing reaction to slowly warm to room temperature. After 1 hr of stirring, TLC indicated reaction was not complete so it was treated with additional 0.03 mole of base and methylsulfamoyl chloride and stirred overnight. After the reaction had gone to completion, it was evaporated to a residue. The residue was dissolved in ethyl acetate/acetonitrile (1:1) (200 ml) and washed with sodium bicarbonate/sodium chloride (1:1) (2×200 ml). The organic layer was evaporated and redissolved in hot ethanol. Upon cooling, crystals precipitated and were filtered and dried. They were then dissolved in methanol and anhydrous HCl in isopropyl alcohol was added. A carbon filtration was done and the methanol evaporated as more isopropanol was added. Off-white crystals precipitated and were filtered, dried, and analyzed (4.14 g, 42%, mp 85°–88° C.).

Analysis: Calc. for $C_{12}H_{15}N_3O_4 \cdot HCl \cdot 0.5H_2O$: C, 42.05; H, 5.00; N, 12.26. Found: C, 42.30; H, 4.99; N, 11.91.

EXAMPLE 76

Sulfamic acid 4-(aminosulfonyl)phenyl ester

This compound was prepared by the procedure used in Example 32. Thus, 20.2 g (0.12 mole) of p-hydroxybenzenesulfonamide, 43 ml (0.48 mole) of chlorosulfonyl isocyanate, 8.5 g (0.47 mole) of water and 53.3 g (0.53 mole) of triethylamine in 250 ml of acetonitrile gave 14.6 g of a viscous residue which solidified upon standing. The solid was purified by chromatography (4×150 cm glass column; 500 g of silica gel; acetone-methylene chloride, 1:5). Fractions containing the product were combined and the solvents evaporated under reduced pressure to give 9.0 g (30%) of a solid. The solid was recrystallized from methylene chloride-acetone to give 2.1 g (7%) of the title compound as fluffy, white needles, mp 139°–142° C.

Analysis: Calculated for $C_6H_8N_2O_5S_2$: C, 28.57; H, 3.20; N, 11.11. Found: C, 28.50; H, 3.25; N, 10.99.

EXAMPLE 77

Sulfamic acid 3-cyanophenyl ester

Using the procedure described in Example 56, the title compound was prepared in 85% yield from 10.3 g (0.086 mole) of 3-cyanophenol and 8.3 ml (0.086 mole) of chlorosulfonyl isocyanate in 75 ml of toluene as a white solid, mp 101°–104° C. (benzene-acetonitrile).

Analysis: Calculated for $C_7H_6N_2O_3S$: C, 42.42; H, 3.05; N, 14.13. Found: C, 42.52; H, 2.82; N, 14.13.

EXAMPLE 78

Sulfamic acid 3-phenylphenyl ester

Using the procedure described in Example 56, the title compound was prepared from 17.0 g (0.010 mole) of 3-phenylphenol and 9.1 ml (0.105 mole) of chlorosulfonyl isocyanate in 100 ml of toluene to obtain 19.0 g (77%) of white flakes, mp 197°–199° C. (benzene-acetonitrile).

Analysis: Calculated for $C_{12}H_{11}NO_3S$: C, 57.82; H, 4.45; N, 5.62. Found: C, 57.60; H, 4.51; N, 5.59.

EXAMPLE 79

Methylsulfamic acid 2-phenoxy-1,3-propanediyl ester

To a stirred solution of 16.8 g (0.1 mole) of 2-phenoxy-1,3-propanediol in 100 ml of methylene chloride was added, dropwise and simultaneously 35.8 g (0.276 mole) of methylsulfamoyl chloride and 36.0 g (0.278 mole) of diisopropylethylamine over a 30 min period. The reaction mixture was stirred for 3 hr, the solvent evaporated under reduced pressure, and the residue was partitioned between ethyl acetate and 2N hydrochloric acid solution (250 ml each). The layers were separated and the organic layer was washed successively with two 250 ml portions of 2N hydrochloric acid and then 250 ml of water, dried, and the solvent was evaporated under reduced pressure to give 45.3 g of a dark, viscous residue. The residue was triturated with ethyl acetate and filtered. The filtrate was evaporated under reduced pressure to give a brown, viscous oil which was purified by column chromatography (4.5×90 cm glass column; 450 g of silica, methylene chloride acetone 100:3). Fractions containing the product were evaporated under reduced pressure and the viscous residue was twice purified by high pressure liquid chromatography (Waters Associates Prep LC/System 500A, PrepPAK 500® silica; ethyl acetate-hexanes, 1:2 and then methylene chloride-acetone, 100:3; flow rate 150 ml/min). Fractions containing the product were combined and the solvents evaporated under reduced pressure to yield 3.5 g (10%) of the title compound as a colorless, viscous oil.

Analysis: Calculated for $C_{11}H_{18}N_2O_7S_2$: C, 37.28; H, 5.12; N, 7.90. Found: C, 37.66; H, 5.49; N, 8.03.

EXAMPLE 80

Sulfamic acid 3-(1H-imidazol-1-yl)phenyl ester monohydrochloride

A solution of 3-(1H-imidazol-1-yl)phenol (8 g, 0.05 mole) in acetonitrile was treated in an ice bath with sulfamoyl chloride generated from 0.075 mole of chlorosulfonyl isocyanate followed by 0.075 mole of triethylamine. After stirring overnight at room temperature, TLC, and $^1$H NMR of a sample showed starting material still present. The reaction was then treated with another 0.075 mole each of sulfamoyl chloride and triethylamine for another night.

The reaction mixture was then concentrated and neutralized with both solid sodium bicarbonate and its solution. The slightly basic mixture was concentrated again to remove of the last trace of acetonitrile. The resultant solid suspension was chilled and then filtered. The sticky solid was dissolved in acetonitrile, stirred with sodium sulfate, magnesium sulfate and charcoal. The mixture was filtered and the filtrate was concentrated to obtain 9.24 g of oil. This oil was dissolved in acetonitrile/isopropyl alcohol, filtered, and acidified with a solution of hydrogen chloride in isopropyl alcohol. Some isopropyl ether was added to precipitate more solid. The solid was collected, weighed (4.63 g) and recrystallized from methanol/isopropyl alcohol to give 4.3 g of solid, mp 164°–165° C.

Analysis: Calculated for $C_9H_9N_3O_3S \cdot HCl$: C, 39.21; H, 3.66; N, 15.24. Found: C, 38.92; H, 3.82; N, 14.80.

EXAMPLE 81

Sulfamic acid 3-iodophenyl ester

This compound was prepared using the procedure of Example 56 from 27.8 g (0.126 mole) of 3-iodophenol and 11.7 ml (0.135 mole) of chlorosulfonyl isocyanate in 100 ml of toluene to obtain 29.4 g (78%) of the title compound as white flakes, mp 106°–108° C. (benzene).

Analysis: Calculated for $C_6H_6INO_3S$: C, 24.10; H, 2.02; N, 4.68. Found: C, 23.94; H, 2.02; N, 4.75.

EXAMPLE 82

Dimethylsulfamic Acid Phenyl Ester

This compound was prepared by the procedure of Example 37. Thus, a solution of 18.8 g (0.2 mol) of phenol and 29.0 ml (0.27 mol) of dimethylsulfamoyl chloride (Aldrich) in 150 ml of toluene gave a viscous oil. The oil was purified by high pressure liquid chromatography (Waters Associates Prep LC/System 500A; PrepPAK 500® silica; ethyl acetate-hexanes, 1:25; flow rate 150 ml/min). Fractions containing the product were combined, the solvents evaporated under reduced pressure, and the viscous residue was dissolved in 500 ml of ethyl ether. The solution was washed successively with three 250 ml portions of a 20% sodium hydroxide solution, 300 ml of water and dried (magnesium sulfate). The solvent was evaporated under reduced pressure to give 10.8 g of a liquid. $^{13}$C NMR indicated that dimethylsulfamoyl chloride was present. Hence the liquid was again purified by high pressure liquid chromatography (Waters Associates Prep LC/System 500A: PrepPAK 500® silica; ethyl acetate-hexanes, 1:20; flow rate 100 ml/min). Fractions containing the product were combined and the solvents evaporated under reduced pressure to yield 6.5 g (16%) of the title compound as a colorless liquid.

Analysis: Calculated for $C_8H_{11}NO_3S$: C, 47.75; H, 5.51; N, 6.96. Found: C, 47.49; H, 5.47; N, 6.88.

EXAMPLE 83

Sulfamic acid 4-methylphenyl ester

This compound was prepared by the procedure used in Example 56. Thus, a solution of 10.8 g (0.1 mole) of 4-methylphenol and 14.8 g (0.105 mole) of chlorosulfonyl isocyanate (95%, Aldrich) in 100 ml of toluene gave 10.3 g (55%) of the title compound as a white solid, mp 80°–82° C. (benzene-petroleum ether, 30°–60° C.).

Analysis: Calculated for $C_7H_9NO_3S$: C, 44.91; H, 4.85; N, 7.48. Found: C, 44.91; H, 4.81; N, 7.40.

EXAMPLE 84

Sulfamic acid 3-(1,1-dimethylethyl)phenyl ester

This compound was prepared according to the procedure used in Example 56. Thus, 15.0 g (0.1 mole) of 3-t-butylphenol (99%, Aldrich) and 14.8 g (0.105 mole) of chlorosulfonyl isocyanate (95%, Aldrich) in 150 ml of xylene gave 13.3 g of a viscous oil that solidified upon standing. The solid was recrystallized from benzene-petroleum ether (30°–60° C.) to give 9.5 g (41%) of the title compound as a white solid, mp 78°–81° C.

Analysis: Calculated for $C_{10}H_{15}NO_3S$: C, 52.38; H, 6.59; N, 6.11. Found: C, 52.46; H, 6.61; N, 6.08.

EXAMPLE 85

Sulfamic acid 3,5-dichlorophenyl ester

The procedure used in Example 56 was used to prepare this compound from a mixture of 16.3 g (0.10 mole) of 3,5-dichlorophenol and 9.1 ml (0.105 mole) of chlorosulfonyl isocyanate in 75 ml of toluene. The compound was obtained in 83% yield as a white, fluffy solid, mp 146°–147° C. (benzene).

Analysis: Calculated for $C_6H_5Cl_2NO_3S$: C, 29.77; H, 2.08; N, 5.77. Found: C, 29.78; H, 2.05; N, 5.76.

EXAMPLE 86

Sulfamic acid 2,3-dichlorophenyl ester

This compound was prepared according to the procedure of Example 56. Thus, a mixture of 16.3 g (0.10 mole) of 2,3-dichlorophenol and 9.1 ml (0.105 mole) of chlorosulfonyl isocyanate in 75 ml of toluene gave 17.4 g (72%) of the title compound as an off-white solid, mp 116°–117° C. (benzene).

Analysis: Calculated for $C_6H_5Cl_2NO_3S$: C, 29.77; H, 2.08; N, 5.77. Found: C, 29.88; H, 2.03; N, 5.77.

EXAMPLE 87

Sulfamic acid 4-cyanophenyl ester

This compound was prepared by the procedure of Example 56 from a solution of 11.9 g (0.10 mole) of 4-cyanophenol (Aldrich Chemical Co.) and 9.1 ml (0.105 mole) of chlorosulfonyl isocyanate in 75 ml of toluene. The solid product was recrystallized from benzene-acetonitrile to give 10.1 g (51%) of white solid, mp 154°–156° C.

Analysis: Calculated for $C_7H_6N_2O_3S$: C, 42.42; H, 3.05; N, 14.13. Found: C, 42.36; H, 2.99; N, 14.10.

EXAMPLE 88

Sulfamic acid 4-methoxyphenyl ester

This compound was prepared according to the procedure used in Example 56. Thus, a solution of 12.4 g (0.1 mole) of 4-methoxyphenol (Aldrich) and 14.8 g (0.105 mole) of chlorosulfonyl isocyanate (95%, Aldrich) in 100 ml of toluene gave a viscous, oily residue. The oil was purified by high pressure liquid chromatography (Waters Associates Prep LC/System 500A, brep-PAK ® 500 silica, methylene chloride; flow rate 200 ml/min). Fractions containing the product were combined and the solvent evaporated under reduced pressure to yield 9.6 g of a viscous oil that solidified upon standing. The solid was recrystallized from benzene-petroleum ether (30°-60° C.) to give 7.9 g (39%) of the title compound as a white solid, mp 62°-64° C.

Analysis: Calculated for $C_7H_9NO_4S$: C, 41.37; H, 4.46; N, 6.89. Found: C, 41.49; H, 4.47; N, 7.05.

EXAMPLE 89

Sulfamic acid 3-(4-methyl-1H-imidazol-1-yl)phenyl ester monohydrochloride

Following the procedure of Example 54, the title compound was prepared from 8.7 g (0.05 mole) of 3-(4-methyl-1H-imidazol-1-yl)phenol in 66% yield, mp 202°-204° C. (methanol-isopropyl ether).

Analysis: Calculated for $C_{10}H_{11}N_3O_3S.HCl$: C, 41.46; H, 4.18; N, 14.50. Found: C, 41.35; H, 4.22; N, 14.35.

EXAMPLE 90

Sulfamic acid 2-methoxyphenyl ester

This compound was prepared according to the procedure of Example 41. Thus, a solution of 12.4 g (0.1 mole) of 2-methoxyphenol (Guaiacol; Aldrich), 40 ml (0.45 mole) of chlorosulfonyl isocyanate (98%; Aldrich), 7.4 g (0.41 mole) of water, and 59.0 g (0.46 mole) of diisopropylethylamine (99%, Aldrich) in 200 ml of acetonitrile and 100 ml of methylene chloride gave 9.0 g of a viscous oil. The oil was purified by high pressure liquid chromatography (Waters Associates Prep LC/System 500A; PrepPAK ® 500 silica; methylene chloride; flow rate 150 ml/min). Fractions containing the product were combined and the solvents evaporated under reduced pressure to give 4.3 g (21%) of a viscous oil that solidified upon standing. The solid was recrystallized from benzene-petroleum ether (30°-60° C.) to give the title compound as white needles, mp 83°-85° C.

Analysis: Calculated for $C_7H_9NO_4S$: C, 41.37; H, 4.46; N, 6.89. Found: C, 41.30; H, 4.47; N, 6.84.

EXAMPLE 91

(S)-(−)-Sulfamic acid 3-(2-methoxyphenoxy)-1,2-propanediyl ester

A slurry of 5.94 g (0.03 mole) of R-(−)-glycerol guaiacolate in 35 ml of methylene chloride was treated by simultaneous addition of a solution of sulfamoyl chloride (0.083 mole) in acetonitrile (15 ml) and diisopropylethylamine (10.75 g, 0.083 mole) in methylene chloride (10 ml) over a 45 min period. The reaction was complete in 1.5 hr. The reaction mixture was washed twice with 100 ml portions of water and the organic layer was chromatographed on silica gel, eluting with 10% methanol in methylene chloride. The desired fractions were combined and concentrated to give 5.6 g (51%) of the title compound as a white powder, mp 136.0°-138.0° C.,$[\alpha]_D^{22}$−4.75° (c=2 in MeOH).

Analysis: Calculated for $C_{10}H_{16}N_2O_8S_2$: C, 33.70; H, 4.53; N, 7.86. Found: C, 33.48; H, 4.62; N, 7.77

EXAMPLE 92

(R)-(+)-Sulfamic acid 3-(2-methoxyphenoxy)-1,2-propanediyl ester

This compound was prepared by the procedure used in Example 91. A combination of 5.94 g (0.03 mole) of S-(+)glycerol guaiacolate, 0.083 mole of sulfamoyl chloride, and 10.8 g (0.083 mole) of diisopropylethylamine gave 4.5 g (41%) of the title compound as a white powder, mp 137.5°-139.0° C.$[\alpha]_D^{22}$+4.80°(c=2 in MeOH).

Analysis: Calculated for $C_{10}H_{16}N_2O_8S_2$: C, 33.70;H, 4.53;N, 7.86. Found: C, 33.66;H, 4.69;N, 7.76.

EXAMPLE 93

Sulfamic acid 2,6-dichlorophenyl ester

This compound was prepared according to the procedure of Example 56 from a mixture of 16.3 g (0.10 mole) of 2,6-dichlorophenol and 9.1 ml (0.105 mole) of chlorosulfonyl isocyanate in 75 ml of toluene to obtain 17.3 g (71%) of the title compound after recrystallization from benzene, mp 114.5°-116° C.

Analysis: Calculated for $C_6H_5Cl_2NO_3S$: C, 29.77; H, 2.08; N, 5.77. Found: C, 29.62; H, 2.05; N, 5.81.

EXAMPLE 94

Sulfamic acid 3-methylphenyl ester

A solution of 0.25 mole of sulfamoyl chloride in 60 ml of acetonitrile was prepared according to the procedure of Example 1, pt. a. The solution was chilled (ice-water bath) and treated dropwise with a solution of 10.8 g (0.10 mole) of 3-methylphenol and 29.7 g (0.23 mole) of diisopropylethylamine in 100 ml of acetonitrile at such a rate that the temperature did not exceed 15° C. The solution was stirred at ambient temperature overnight and then diluted with 200 ml of ethyl acetate and 50 ml of water. The layers were separated and the organic layer washed successively with two 50 ml portions of water, 50 ml of 2N hydrochloric acid solution, 50 ml of water, brine, and dried (sodium sulfate) and concentrated to give a brown gum. The gum was purified by column chromatography (400 g silica gel eluted with methylene chloride). The appropriate fractions were combined and concentrated to give a solid residue which was recrystallized from benzene to yield 9.2 g (48%) of the title compound as white plates, mp 84-85° C. (reported mp 88° C., Chem. Ber. 105, 2791-2799(1972)).

Analysis: Calculated for $C_7H_9NO_3S$: C, 44.91; H, 4.84; N, 7.48. Found: C, 44.77; H, 4.88; N, 7.53.

EXAMPLE 95

Sulfamic acid 3-(4-phenyl-1H-imidazol-1-yl)phenyl ester hydrochloride

Using the same procedure of Example 54, 9.36 g (0.04 mole) of 3(4-phenyl-1H-imidazol-1-yl)phenol was converted to the title compound in 60% yield, mp 209°-211° C.

Analysis: Calculated for $C_{15}H_{13}N_3O_3S.HCl$: C, 51.21; H, 4.01; N, 11.94. Found: C, 51.17; H, 3.99; N, 11.82.

EXAMPLE 96

Sulfamic acid 3-fluorophenyl ester

To a cooled (ice bath) solution of 11.2 g (0.1 mole) of 3-fluorophenol (98%, Aldrich) in 75 ml of toluene was added 9.1 ml (14.8 g, 0.105 mol) of chlorosulfonyl isocyanate, and the solution heated at reflux overnight. The solution was cooled and cautiously treated dropwise with water until carbon dioxide evolution ceased. An oil separated and ethyl acetate was added to dissolve this oil. The layers were separated and the organic layer was washed with water, dried (sodium sulfate) and concentrated to give an oil which gradually crystallized. The solid was purified by column chromatography on 400 g of silica gel eluted with methylene chloride. The appropriate fractions were combined and concentrated to yield 9.2 g (48%) of the title compound which was recrystallized from benzene to give a white solid, mp 53°–55° C.

Analysis: Calculated for $C_6H_6FNO_3S$: C, 37.70; H, 3.16; N, 7.33. Found: C, 37.70; H, 3.08; N, 7.35.

EXAMPLE 97

Sulfamic acid 3,5-bis(trifluoromethyl)phenyl ester

This compound was prepared using the procedure of Example 56 from a mixture of 9.8 g (0.043 mole) of 3,5-bis(trifluoromethyl)phenol and 3.9 ml (0.095 mole) of chlorosulfonyl isocyanate in 50 ml of toluene. The solid product was recrystallized from benzene to yield 6.4 g (48%) of a pale yellow solid, mp 118°–120° C.

Analysis: Calculated for $C_8H_5F_6NO_3S$: C, 31.08; H, 1.63; N, 4.53. Found: C, 31.11; H, 1.52; N, 4.60.

EXAMPLE 98

Sulfamic acid 3,5-difluorophenyl ester

Using the procedure of Example 56, the title compound was prepared using a mixture of 9.9 g (0.076 mole) of 3,5-difluorophenol and 7.0 ml (0.08 mole) of chlorosulfonyl isocyanate in 50 ml of toluene. The solid product was recrystallized from benzene to yield 11.7 g (74%) of white solid, mp 85°–88° C.

Analysis: Calculated for $C_6H_5F_2NO_3S$: C, 34.45; H, 2.41; N, 6.70. Found: C, 34.53; H, 2.34; N, 6.79.

EXAMPLE 99

Sulfamic acid 4-fluorophenyl ester

Using the procedure of Example 56, a mixture of 11.2 g (0.1 mole) of 4-flurophenol and 9.1 ml (0.105 mole) of chlorosulfonyl isocyanate in 50 ml of toluene gave, after recrystallization from benzene, 15.0 g (79%) of the title compound as a white solid, mp 82.5°–85.5° C.

Analysis: Calculated for $C_6H_6FNO_3S$: C, 37.70; H, 3.16; N, 7.33. Found: C, 37.83; H, 3.11; N, 7.37.

EXAMPLE 100

Sulfamic acid 2-[3-(1H-imidazol-1-yl)phenoxy]ethyl ester monohydrochloride

A solution of sulfamoyl chloride (0.0275 mole) in 60 ml of acetonitrile was treated dropwise with a solution of 5.1 g (0.025 mole) of 2-[3-(1H-imidazol-1-yl)phenoxy]ethanol in 100 ml of acetonitrile. The mixture was stirred at ambient temperature under nitrogen for 20 hr. The mixture was concentrated under vacuum, and the residue was partitioned between ethyl acetate and dilute potassium carbonate solution. The organic fraction was again concentrated under vacuum to a crystalline residue. This residue was dissolved in warm 95% ethanol and treated with 1 equivalent of anhydrous hydrogen chloride. The solution was chilled and the precipitate was collected and dried to give 4.0 g (50%) of the title compound as a pink powder, mp 149.0°–150.0° C.

Analysis: Calculated for $C_{11}H_{13}N_3O_4S \cdot HCl$: C, 41.32; H, 4.41; N, 13.14. Found: C, 41.25; H, 4.50; N, 12.92.

EXAMPLE 101

Sulfamic acid 3-(2-methoxyphenoxy)propyl ester

A solution of 13.0 g (.071 mole) of 3-(2-methoxyphenoxy)-1-propanol [prepared in 68% yield from guaiacol (43.2 g, 0.35 mole), 3-bromo-1-propanol (89.3 g, 0.61 mole) and potassium carbonate (112.0 g, 0.81 mole) in 1 l of acetone] and 9.0 g (.089 mole) of triethylamine in 50 ml of methylene chloride was added dropwise (20 min.) to a stirred, cooled (ice-acetone bath) solution of 22 ml (.079 mole) of sulfamoyl chloride (3.57 M solution in acetonitrile), in 30 ml methylene chloride at such a rate the temperature was maintained at $\leq 12°$ C. The reaction mixture was stirred at ambient temperature for 3 hr. The solvents were evaporated under reduced pressure and the viscous residue was triturated with 300 ml of ethyl acetate and the solids removed by filtration. The filtrate was washed with three 300 ml portions of water, dried (magnesium sulfate) and the solvent evaporated under reduced pressure to yield 11.7 g (63%) of a colorless, viscous oil that solidified upon standing. The solid was recrystallized from methylene chloride-petroleum ether (30°–60° C.) to give 6.9 g (37%) of the title compound as a white solid, mp 80°–83° C.

Analysis: Calculated for $C_{10}H_{15}NO_5S$: C, 45.97; H, 5.79; N, 5.36. Found: C, 45.85; H, 5.85; N, 5.28.

EXAMPLE 102

Methylsulfamic acid 2-methoxyphenyl ester

A solution of 12.4 g (0.1 mole) of 2-methoxyphenol (guaiacol; Aldrich) and 13.1 g (0.1 mole) of methylsulfamoyl chloride in 150 ml of toluene was stirred and heated at reflux for 2 hr. The solvent was evaporated under reduced pressure and the oily residue was purified by high pressure liquid chromatography (Waters Associates Prep LC/System 500A, PrepPAK ® 500A silica, ethyl acetate-hexanes, 1:2; flow rate 150 ml/min). Fractions containing the product were combined and the solvents evaporated under reduced pressure to yield an oil that solidified upon standing. The solid was recrystallized from benzene-petroleum-ether (30°–60° C.) to give 14.3 g (66%) of the title compound as a white solid, mp 68°–71° C.

Analysis: Calculated for $C_8H_{11}NO_4S$: C, 44.23; H, 5.10; N, 6.45. Found: C, 44.09; H, 5.12; N, 6.41.

EXAMPLE 103

Sulfamic acid 4-iodophenyl ester

This compound was prepared according to the procedure of Example 56. A mixture of 22.0 g (0.1 mole) of 4-iodophenol (Aldrich) and 9.1 ml (14.8 g, 0.105 mole) of chlorosulfonyl isocyanate in 100 ml of toluene gave 23.8 g (80%) of the title compound as a white solid, mp 146°–147° C.

Analysis: Calculated for $C_6H_6INO_3S$: C, 24.10; H, 2.02; N, 4.68. Found: C, 24.07; H, 1.95; N, 4.67.

EXAMPLE 104

Sulfamic acid 3-[4-(1H-imidazol-1-yl)phenoxy]propyl ester

A solution of 9.0 g (0.041 mole) of 3-[4-(1H-imidazol-1-yl)phenoxy]-1-propanol in 150 ml of acetonitrile was treated with a solution of one equivalent of sulfamoyl chloride in 13 ml of acetonitrile. The mixture was stirred for 20 hr. The reaction mixture was concentrated under vacuum and the residue was dissolved in water. The aqueous solution was filtered and the filtrate was basified to pH 8 with potassium carbonate. The mixture was extracted with ethyl acetate. The organic fraction was concentrated under a stream of nitrogen and the precipitate was collected and dried to give 5.2 g (43%) of the title compound as a tan powder, mp 105°–106° C.

Analysis: Calculated for $C_{12}H_{15}N_3O_4S$: C, 48.48; H, 5.09; N, 14.13. Found: C, 48.73; H, 5.12; N, 13.95.

EXAMPLE 105

Sulfamic acid 3-[2-[(aminosulfonyl)oxy]ethoxy]phenyl ester

To a stirred solution of 0.59 mole of sulfamoyl chloride[1] in 100 ml of acetonitrile was added dropwise simultaneously 85.3 g (0.66 mole) of diisopropylethylamine (Hunig's base, Aldrich) and a solution of 15.7 g (0.1 mole) of O-(2-hydroxyethyl)resorcinol (98%; Lancaster Synthesis, Windham, NH 03087) in 100 ml of acetonitrile (temp.≦15° C.; 20 min). The reaction mixture was stirred at ambient temperature for 3 hr, the solvent evaporated under reduced pressure and the residue was partitioned between ethyl acetate and water (300 ml each). The organic layer was washed with four 300 ml portions of water (pH neutral to pH paper), dried (sodium sulfate), and the solvent evaporated under reduced pressure to give 17.6 g of a viscous residue. The residue was purified by high pressure liquid chromatography (Waters Associates Prep LC/System 500A; Prep-PAK ® 500 silica, methylene chloride-acetone, 10:1, flow rate 150 ml/min.[2] Desired fractions were combined and the solvents evaporated under reduced pressure to give 7.9 g (25%) of an oil that solidified upon standing. The solid was recrystallized from ethyl acetate-benzene to give 4.6 g (15%) of white solid, mp 142°–144° C.

[1]The sulfamoyl chloride was prepared from 52 ml (0.59 mole) of chlorosulfonyl isocyanate (98%, Aldrich) and 10.4 g (0.58 mole) of water in 100 ml of acetonitrile and was used as such.
[2]The residue yielded 3.0 g (12%) of 3-(2-chloroethoxy)phenyl sulfamate ester (Example 113).

Analysis: Calculated for $C_8H_{12}N_2O_7S_2$: C, 30.77; H, 3.87; N, 8.97. Found: C, 30.85; H, 3.95; N, 8.92.

EXAMPLE 106

Sulfamic acid 3-methoxyphenyl ester

This compound was prepared according to the procedure used in Example 42. Thus, a solution of 12.4 g (0.1 mole) of 3-methoxyphenol (Aldrich), 31 ml (0.35 mole) of chlorosufonylisocyanate (98%, Aldrich), 5.7 g (0.32 mole) of water, and 35.9 g (0.36 mole) of triethylamine in 200 ml of acetonitrile gave 8.3 g of a brown, viscous oil. The oil was purified by high pressure liquid chromatography (Waters Associates Prep LC/System 500A; PrepPAK ® 500 silica; methylene chloride; flow rate 150 ml/min). Fractions containing the desired compound were combined and the solvents evaporated under reduced pressure to yield a viscous oil that solidified upon standing. The solid was recrystallized from benzene-petroleum ether (30°–60° C.) to give 3.5 g (17%) of a white solid, mp 59°–61° C.

Analysis: Calculated for $C_7H_9NO_4S$: C, 41.37; H, 4.46; N, 6.89. Found: C, 41.40; H, 4.48; N, 6.85.

EXAMPLE 107

Sulfamic acid 2-[3-(2-methyl-1H-imidazol-1-yl)phenoxy]ethyl ester monohydrochloride A mixture of 17.4 g (0.10 mole) of 3-(2-methyl-1H-imidazol-1-yl)phenol, 40.2 g (0.50 mole) of chloroethanol and 70 g (0.5 mole) of potassium carbonate in 100 ml of methyl ethyl ketone was heated at reflux for 30 hr. The reaction mixture was filtered and the filtrate was concentrated. The residue was partitioned between ethyl acetate and dilute potassium carbonate solution. The organic layer was concentrated and chromatographed on silica gel to give 7 g of desired product of approximately 90% purity. This intermediate was sulfamoylated by treatment in 150 ml of acetonitrile with 1.3 equivalents of sulfamoyl chloride in 13 ml of acetonitrile and 1 g of diisopropylethyl amine. When HPLC indicated all starting material was consumed, the reaction mixture was quenched with water, then concentrated to a syrup. The syrup was partitioned between ethyl acetate and dilute potassium carbonate solution. The organic layer was concentrated and chromatographed on silica gel. The fractions containing desired product were combined and concentrated. The syrup (3.0 g) was dissolved in 40 ml of 2-propanol and treated with 1 equivalent of anhydrous hydrogen chloride. The precipitate was collected and dried to give 2.8 g (9.4%) of off-white powder. This material was recrystallized from 95% ethanol to give 1.9 g of tan-yellow crystals, mp 184°–186° C.

Analysis: Calculated for $C_{12}H_{15}N_3O_4S\cdot HCl$: C, 43.18; H, 4.83; N, 12.59. Found: C, 43.36; H, 4.90; N, 12.41.

EXAMPLE 108

Sulfamic acid 2-[4-(2H-1,2,4-triazol-2-yl)-phenoxy]ethyl ester

A solution of 8.2 g (0.04 mole) of 2-[4-(1H-1,2,4-triazol-1-yl)phenoxy]ethanol in 100 ml of acetonitrile was treated with a solution of 1.3 equivalents of sulfamoyl chloride in 19 ml of acetonitrile. One equivalent, 5.2 g (0.04 mole), of diisopropylethylamine was also added in one portion. The mixture was stirred for 2 hr. The precipitate was collected and partitioned between ethyl acetate and a dilute potassium carbonate solution. The organic layer was separated and concentrated to a white powder. The powder was triturated with ethyl ether, collected and dried to give 6.3 g (55%) of white powder, mp 134°–136° C.

Analysis: Calculated for $C_{10}H_{12}N_4O_4S$: C, 42.25; H, 4.26; N, 19.71. Found: C, 42.39; H, 4.31; N, 19.41.

EXAMPLE 109

Sulfamic acid 2-[3-(4-methyl-1H-imidazol-1-yl)phenoxy]ethyl ester monohydrochloride By the same procedure used for Example 89, 2-[3-(4-methyl-1H-imidazol-1-yl)phenoxy]ethanol hydrochloride was first converted to its free base and then to the title compound in 51% overall yield, mp 169°–170° C.

Analysis: Calculated for $C_{12}H_{15}N_3O_4S\cdot HCl$: C, 43.18; H, 4.83; N, 12.59. Found: C, 42.74; H, 4.87; N, 12.38.

EXAMPLE 110

Sulfamic acid 3-(2-methyl-1H-imidazol-1-yl)-phenyl ester monohydrochloride

A slurry of 8.7 g (0.05 mole) of 3-(2-methyl-1H-imidazol-1-yl)phenol in 150 ml of acetonitrile was treated with a solution of 0.05 mole of sulfamoyl chloride in 20 ml of acetonitrile. The mixture dissolved and slowly deposited off-white crystals over the period of 24 hr. The precipitate was collected and triturated with hot absolute ethanol. The slurry was cooled and the precipitate was collected and dried to give 4.0 g (32%) of an off-white powder, mp 197°–200° C.

Analysis: Calculated for $C_{10}H_{11}N_3O_3S \cdot HCl$: C, 41.46; H, 4.18; N, 14.50. Found: C, 41.28; H, 4.22; N, 14.57.

EXAMPLE 111

Sulfamic acid 2-fluorophenyl ester

This compound was prepared according to the procedure of Example 56. A mixture of 11.2 g (0.1 mole) of 2-fluorophenol and 9.1 ml (14.8 g, 0.105 mole) of chlorosulfonyl isocyanate in 50 ml of toluene gave 7.3 g (38%) of the title compound as a white solid, mp 63°–64° (benzene).

Analysis: Calculated for $C_6H_6FNO_3S$: C, 37.70; H, 3.16; N, 7.33. Found: C, 37.63; H, 3.08; N, 7.29.

EXAMPLE 112

Methylsulfamic acid 2-(2-methoxy)ethyl ester

To a stirred solution of 12.2 g (0.094 mole) of methylsulfamoyl chloride in 100 ml of acetonitrile was added a solution of 12.6 g (0.075 mole) 2-(2-methoxyphenoxy)ethanol and 9.7 g (0.096 mole) of triethylamine (temp. $\leq 15°$ C.; 15 min). The reaction mixture was stirred at ambient temperature for 2 hr, the solids were removed by filtration, and the filtrate was evaporated under reduced pressure to yield a viscous residue. The residue was partitioned between ethyl ether (500 ml) and water (300 ml). The organic layer was washed twice with 300 ml portions of water, dried (magnesium sulfate) and the solvent evaporated under reduced pressure to yield a viscous oil. The oil was purified by high pressure liquid chromatography (Waters Associate Prep LC/System 500A; PrepPAK® 500 silica; ethyl acetate-hexanes, 1:2). Fractions containing the desired compound were combined and the solvents evaporated under reduced pressure to give 8.2 g (42%) of a colorless, viscous oil.

Analysis: Calculated for $C_{10}H_{15}NO_5S$: C, 45.97; H, 5.79; N, k5.36. Found: C, 45.57; H, 5.96; N, 5.42.

EXAMPLE 113

Sulfamic acid 3-(2-chloroethoxy)phenyl ester

This compound was isolated (12% yield; HPLC) as a solid by-product in the preparation of the compound of Example 105. The solid was recrystallized from benzene-petroleum ether (30°–60° C.) to yield a white solid, mp 94°–96° C.

Analysis: Calculated for $C_8H_{10}ClNO_4S$: C, 38.18; H, 4.01; N, 5.57. Found: C, 38.30; H, 4.04; N, 5.53.

EXAMPLE 114

Methylsulfamic acid 2-phenoxyethyl ester

This compound was prepared according to the procedure used in Example 112. Thus, a mixture of 14.8 g (0.1 mole) of 2-phenoxyethanol (Matheson, Coleman, and Bell), 15.6 g (0.12 mole) of methylsulfamoyl chloride and 12.3 g (0.12 mole) of triethylamine in 150 ml of acetonitrile gave a viscous oil that solidified upon standing. The solid was recrystallized from benzene-petroleum ether (30°–60° C.) to yield 15.4 g (67%) of shiny, white flakes, mp 66°–68° C.

Analysis: Calculated for $C_9H_{13}NO_4S$: C, 46.74; H, 5.67; N, 6.06. Found: C, 46.68; H, 5.75; N, 6.07.

EXAMPLE 115

Sulfamic acid 3-(2-ethoxyphenoxy)-1,2-propanediyl ester

To a cold (ice bath) solution of 14.8 ml (24.0 g, 0.17 mole) of chlorosulfonyl isocyanate in 75 ml of acetonitrile at 10° C. was added dropwise a solution of 7.3 g (0.17 mole) of 96% formic acid in 25 ml of acetonitrile at such a rate that the temperature did not exceed 15° C. After the addition was complete the mixture was stirred at ambient temperature for 6 hr until gas evolution ceased. The reaction mixture was cooled to 10° C. and treated dropwise with a solution of 15.9 g (0.075 mol) of 3-(2-ethoxyphenoxy)-1,2-propanediol and 26 ml (19.3 g, 0.15 mole) of diisopropylethylamine in 150 ml of acetonitrile while maintaining the temperature at 10°–15° C. The solution was stirred overnight at ambient temperature and then additional diisopropylethylamine was added dropwise until the pH of the solution remained basic for 15 min. The mixture was concentrated under reduced pressure and the residue was dissolved in 250 ml of methylene chloride. The organic layer was washed successively with 50 ml portions of water, 2N hydrochloric acid solution, water, dilute sodium bicarbonate solution, and brine, dried (sodium sulfate), and concentrated to give $\sim 30$ g of gum as residue. The gum was purified on 600 g of silica gel eluted with 0–15% acetone in methylene chloride. Appropriate fractions were combined and concentrated to yield 9.1 g (33%) of a white solid, mp 113°–115° (benzene-acetonitrile).

Analysis: Calculated for $C_{11}H_{18}N_2O_8S_2$: C, 35.67; H, 4.90; N, 7.56. Found: C, 35.66; H, 4.98; N, 7.53.

EXAMPLE 116

Sulfamic acid 2-[3-(phenylmethoxy)phenoxy]ethyl ester.

This compound was prepared according to the procedure used in Example 101. Thus, a mixture of 14.7 g (0.06 mole) of 2-(3-benzyloxyphenoxy)ethanol, 17 ml (0.066 mole) of sulfamoyl chloride (3.9 M solution in acetonitrile) and 7.0 g (0.069 mole) of triethylamine in 150 ml of acetonitrile gave a viscous, oily residue. The oil was triturated with benzene-petroleum ether (30°–60° C.) and the solid was collected by filtration. The solid was recrystallized from chloroform to yield 8.6 g (44%) of a white solid, mp 107°–109° C.

Analysis: Calculated for $C_{15}H_{17}NO_5S$: C, 55.72; H, 5.30; N, 4.33. Found: C, 55.39; H, 5.26; N, 4.27.

EXAMPLE 117

Methylsulfamic acid 3-[(2-phenylmethoxy)phenoxy]-1,2-propanediyl ester

To a solution of 21.4 g (0.165 mole) of methylsulfamoyl chloride in 100 ml of methylene chloride was added dropwise a solution of 20.6 g (0.075 mole) of 3-[2-(phenylmethoxy)phenoxy]-1,2-propanediol and 21.3 g (0.165 mole) of diisopropylethylamine in 250 ml of methylene chloride, and the solution was stirred at ambient temperature overnight. The solution was washed successively with 150 ml of water, twice with 150 ml of 2N hydrochloric acid solution, 150 ml of water, 150 ml of dilute sodium bicarbonate solution, and 150 ml of brine, dried (sodium sulfate), and concentrated to give a solid residue. The solid was recrystallized from 2-propanol (charcoal) to yield 19.2 g (56%) of a white solid, mp 95°–97.5° C.

Analysis: Calculated for $C_{18}H_{24}N_2O_8S_2$: C, 46.95; H, 5.25; N, 6.08. Found: C, 47.00; H, 5.40; N, 6.04.

EXAMPLE 118

Sulfamic acid 2-[3-(diethylamino)phenoxy]ethyl ester 2-(3-Nitrophenoxy)ethanol (13.7 g, 0.075 mole), acetaldehyde (30 ml, 0.52 mole), and 5% palladium on carbon (1.5 g) in 100 ml methanol and 20 ml ethanol was hydrogenated on Parr hydrogenator for 3.5 hr whereupon the pressure drop had ceased. The mixture was filtered, and the filtrate concentrated to an oil (18.4 g). This oil was chromatographed on 350 g silica gel eluted with 5% methanol/methylene chloride to give 8.45 g of almost colorless oil. $^1$H NMR supported the structure of 2-(m-diethylaminophenoxy) ethanol(I). Compound I (7.45 g, 0.036 M) was converted to the title compound by reacting with the sulfamoyl chloride generated by mixing chlorosulfonylisocyanate (0.09 M) and formic acid (0.09 M) in acetonitrile. The product free base was isolated by acid-base transfer extractions. The oily free base solidified upon cooling. The solid was recrystallized twice from toluene and dried overnight under vacuum at room temperature. mp 105°–106° C.

Analysis: Calculated for $C_{12}H_{20}N_2O_4S$: C, 49.98; H, 6.99; N, 9.71. Found: C, 49.86; H, 7.09; N, 9.71.

EXAMPLE 119

Sulfamic acid 1,3-phenylene ester

A solution of 11.0 g (0.1 mole) of resorcinol and 54.4 g (0.54 mole) of triethylamine in 100 ml of acetonitrile was added to a stirred, cooled (acetone-ice bath, $\leq 12°$ C.) solution of 150 ml (0.59 mole) of sulfamoyl chloride (3.9 M solution in acetonitrile) over a 25 min period, and the mixture was stirred at ambient temperature overnight. The reaction mixture was treated with water (200 ml) and ethyl acetate (400 ml). The organic layer was evaporated under reduced pressure and the residue was partitioned between ethyl acetate (400 ml) and water (300 ml). The organic layer was washed with five 300-ml portions of water (pH neutral to pH paper), dried (magnesium sulfate), and the solvent was evaporated under reduced pressure to give a viscous oil that solidified upon standing. The solid was recrystallized from ethyl acetate-petroleum ether (30°–60° C.) to yield 3.5 g (13%) of white solid, mp 104°–106° C.

Analysis: Calculated for $C_6H_8N_2O_6S_2$: C, 26.86; H, 3.01; N, 10.44. Found: C, 27.09; H, 3.05; N, 10.26.

EXAMPLE 120

Methylsulfamic acid 3-(2-ethoxyphenoxy)-1,2-propanediyl ester

To a solution of 21.4 g (0.165 mole) of methylsulfamoyl chloride in 100 ml of methylene chloride was added dropwise a solution of 15.9 g (0.075 mole) of 3-(2-ethoxyphenoxy)-1,2-propanediol and 21.3 g (0.165 mole) of diisopropylethylamine in 200 ml of methylene chloride, and the mixture was stirred at ambient temperature overnight. The solution was washed successively twice with 150 ml portions of 2N hydrochloric acid solution, once with a dilute sodium bicarbonate solution and once with brine, dried (sodium sulfate), and concentrated to give ~34 g of gum residue. The gum was purified by column chromatograpy in 600 g of silica gel eluted with 0–5% acetone in methylene chloride. The appropriate fractions were combined and concentrated to give a gum which gradually crystallized over several days. The solid was triturated with petroleum ether, collected by filtration, and dried to yield 25.0 g (84%) of a white solid, mp 55°–58° C.

Analysis: Calculated for $C_{13}H_{22}N_2O_8S_2$: C, 39.19; H, 5.57; N, 7.03. Found: C, 38.79; H, 5.68; N, 7.19.

EXAMPLE 121

Sulfamic acid 4-(2-methyl-1H-imidazol-1-yl)phenyl ester monohydrochloride

To a chilled solution of acetonitrile (50 ml) and chlorosulfonyl isocyanate (12.16 g, 0.086 mole) was added benzyl alcohol (9.29 g, 0.086 mole) while maintaining the temperature between 10°–15° C. The reaction stirred at room temperature 1.5 hr and 4-(2-methyl-1H-imidazol-1-yl)phenol (10.0 g, 0.057 mole) added in small portions) while maintaining the temperature below 20° C. The reaction was stirred overnight and its progress checked by thin layer chromatography (8:1:1 ethyl acetate/methanol/ammonium hydroxide). Once the reaction had gone to completion, isopropyl alcohol (3.42 g, 0.057 mole) was added and reaction stirred an additional hour. The solution was concentrated and the residue dissolved in methanol (150 ml) and the solution subjected to catalytic hydrogenation using 5% palladium on carbon catalyst. The solution was filtered and the filtrate concentrated, replacing the methanol with isopropyl alcohol. White crystals precipitated and were collected and dried (9.8 g, 59.5%, mp 197°–200° C.).

Analysis: Calculated for $C_{10}H_{11}N_3O_3S \cdot HCl$: C, 41.46; H, 4.18; N, 14.50. Found: C, 41.19; H, 4.23; N, 14.29.

EXAMPLE 122

Methylsulfamic acid 3-(2-hydroxyphenoxy)-1,2-propanediyl ester

A solution of 9.2 g (0.02 mole) of methylsulfamic acid 2-[[(methylamino)sulfonyl]oxy]-3-[2-(phenylmethoxy)-phenoxy]propyl ester in 250 ml of ethyl acetate was hydrogenated in a Parr apparatus over 0.25 teaspoon of 5% palladium on carbon at 50° C. overnight. No hydrogen was consumed so the catalyst was removed by filtration, fresh catalyst added, and the mixture hydrogenated at 60° C. overnight. Again, no hydrogen was consumed so the catalyst was removed, and 0.25 teaspoon of 10% palladium on carbon was added and the mixture hydrogenated at 60° C. Hydrogen uptake ceased after 1 hr. The mixture was cooled, filtered, and the filtrate concentrated to give a gum. This gum was purified by column chromatography on 150 g of silica gel, eluting with 0–10% acetone in methylene chloride. The appropriate fractions were combined and concentrated to give a gum which eventually crystallized. The solid was triturated with petroleum ether (30°–60° C.), collected by filtration, and dried to yield 6.8 g (92%) of a white solid, mp 87°–90° C.

Analysis: Calculated for $C_{11}H_{18}N_2O_8S_2$: C, 35.67; H, 4.90; N, 7.56. Found: C, 35.64; H, 4.96; N, 7.61.

EXAMPLE 123

(S)-(−)-Methylsulfamic acid
3-(2-methoxyphenoxy)-1,2-propanediyl ester

A slurry of 6.6 g (0.033 mole) of R-(−)glyceryl guaiacolate in 40 ml of methylene chloride was treated with simultaneous addition of solutions of methylsulfamoyl chloride (0.3 g, 0.072 mole) in 13 ml of methylene chloride and diisopropylethylamine (9.3 g, 0.072 mole) in 9 ml of methylene chloride over a period of 0.5 hr. The solution was stirred for an additional 2 hr then chromatographed on silica gel, eluting with 3% tetrahydrofuran in methylene chloride. Concentration of the desired fractions gave an oil which crystallized on standing. The solid mass of crystals was recrystallized from a combination of n-propanol and isopropyl ether to give 10.2 g (80%) of a white powder, mp 50.0°–51.5° C., $[\alpha]^{22}D = -5.3°$ (c=1, MeOH).

Analysis: Calculated for $C_{12}H_{20}N_2O_8S_2$: C, 37.49; H, 5.24; N, 7.29. Found: C, 37.55; H, 5.34; N, 7.28.

EXAMPLE 124

(R)-(+)-Methylsulfamic acid
3-(2-methoxyphenoxy)-1,2-propanediyl ester

This compound was prepared by the procedure of Example 123. A mixture of 3.96 g (0.02 mole) of S-(+) glyceryl guaiacolate, 5.7 g (0.044 mol) of methylsulfamoyl chloride, and 5.7 g (0.044 mole) of diisopropylethylamine gave, after chromatography and recrystallization, 5.0 g (65%) of the title compound as a white powder, mp 50.5°–52.0° C., $[\alpha]^{22}D = +5.3°$ (c=1, MeOH).

Analysis: Calculated for $C_{12}H_{20}N_2O_8S_2$: C, 37.49; H, 5.24; N, 7.29. Found: C, 37.46; H, 5.32; N, 7.27.

EXAMPLE 125

Sulfamic acid
2-[4-[2-[(aminosulfonyl)oxy]ethoxy]phenoxy]ethyl ester

A mixture of 19.8 g (0.1 mole) of hydroquinone bis (2-hydroxyethyl)ether (98%, Aldrich) and 41.4 g (0.41 mole) of triethylamine in 350 ml of acetonitrile was added to a cooled (acetone-ice bath, temp≦15° C.) solution of 130 ml of sulfamoyl chloride solution (3.14 M solution in acetonitrile) and 100 ml of acetonitrile. The mixture was mechanically stirred at ambient temperature overnight. The solvent was evaporated under reduced pressure and the residue was partitioned between 400 ml of water and 800 ml of ethyl acetate. The aqueous layer was extracted with two 400 ml portions of ethyl acetate and the combined ethyl acetate extracts (1.6l) were washed with two 400 ml portions of water, dried (magnesium sulfate) and the solvent evaporated under reduced pressure to give a viscous residue which was triturated with 100 ml of methylene chloride and let stand at ambient temperature for two days. The resulting solid was collected by filtration and then washed with water until the filtrate was neutral to pH paper and dried (air). The solid was recrystallized from acetonitrile to yield 9.9 g (29%) of a white solid containing a small amount of acetonitrile, mp 162°–164° C.

Analysis: Calculated for $C_{10}H_{16}N_2O_8S_2$: C, 33.70; H, 4.53; N, 7.86. Found: C, 34.30; H, 4.62, N, 8.03.

Analysis: Calc. for $C_{10}H_{16}N_2O_8S_2 \cdot 0.07CH_3CN$: C, 33.90; H, 4.55; N, 8.07.

EXAMPLE 126

Sulfamic acid 2-[4-(phenylmethoxy)phenoxy]ethyl ester

To a stirred suspension of 30.0 g (0.12 mole) of 4-(benzyloxy)phenoxyethanol in 150 ml of acetonitrile was added simultaneously 59 ml (0.18 mole) of sulfamoyl chloride solution (3.14 M solution in acetonitrile) and 19.5 g (0.19 mole) of triethylamine. The resulting clear solution was stirred at ambient temperature for 5 hr and then poured into 2 L of water. The resulting solid was collected by filtration and the filter cake was washed with 1.5 L of water and dried (air). The solid was recrystallized from chloroform to yield 31.1 g (78%) of a white solid, mp 125°–128° C.

Analysis: Calculated for $C_{15}H_{17}NO_5S$: C, 55.72; H, 5.30; N, 4.33. Found: C, 55.45; H, 5.27; N, 4.35.

EXAMPLE 127

Dimethylsulfamic acid 3-chlorophenyl ester

A solution of 25.7 g (0.2 mole) of 3-chlorophenol and 34.9 g (0.24 mole) of dimethylsulfamoyl chloride (Aldrich) in 150 ml of toluene was stirred and heated at reflux for 16 h, cooled and treated with 300 ml of 15% sodium hydroxide solution. The layers were separated and the organic layer was washed with two 200 ml portions of 15% sodium hydroxide solution, 300 ml of water and dried (magnesium sulfate). The solvent was evaporated under reduced pressure and the brown viscous oil was purified by chromatography (4.5×90 in glass column, 530 g of silica gel, ethyl acetate-hexanes, 1:6). Fractions containing the desired product were combined and the solvents were evaporated under reduced pressure to yield 10.5 g (47%) of the title compound as a light yellow liquid.

Analysis: Calculated for $C_8H_{10}ClNO_3S$: C, 40.77; H, 4.28; N, 5.94. Found: C, 40.01; H, 4.29; N, 5.91.

EXAMPLE 128

Dimethylsulfamic acid 2-methoxyphenyl ester

A solution of 24.8 g (0.2 mole) of guaiacol (Aldrich) and 34.9 g (0.27 mole) of diisopropylethylamine (Hunig's base, Aldrich) in 200 ml of toluene was added to a solution of 29 ml (0.27 mole) of dimethylsulfamoyl chloride (Aldrich) in 75 ml of toluene and the stirred reaction mixture was heated at reflux for 12 hr. The reaction mixture was successively washed with four 300 ml portions of 6N hydrochloric acid solution, 400 ml of water, three 200 ml portions of 20% sodium hydroxide solution, 400 ml of water and dried (magnesium sulfate). The solvent was evaporated under reduced pressure to give a brown, viscous oil that solidified upon standing. The solid was recrystallized from ethyl ether-petroleum ether and was collected by filtration. The filtrate was evaporated under reduced pressure and the viscous, brown oil was purified by chromatography (4.5×90 cm glass column, 5.30 g of silica gel, ethyl acetate-hexanes, 1:8). Fractions containing the desired compound were combined and the solvents evaporated under reduced pressure to yield 2.5 g (5%) of the title compound as a light yellow liquid.

Analysis: Calculated for $C_9H_{13}NO_4S$: C, 46.74; H, 5.67; N, 6.06. Found: C, 46.76; H, 5.73; N, 6.04.

EXAMPLE 129

Sulfamic acid 2-(4-chlorophenoxy)-1,3-propanediyl ester

To a cooled (ice bath)solution of 7.8 ml (12.7 g, 0.09 mole) of chlorosulfonyl isocyanate in 50 ml of acetonitrile was added portionwise a solution of 3.9 g (0.09 mole) of 96% formic acid in 20 ml of acetonitrile at such a rate that the reaction mixture temperature did not exceed 12° C. After the addition was complete, the solution was stirred at ambient temperature for 3 hr (until gas evolution had ceased). The reaction mixture was cooled to 10° C. and treated dropwise with a solution of 8.1 g (0.04 mole) of 2-(4-chlorophenoxy)-1,3-propanediol and 13.9 ml (10.3 g, 0.08 mole) of diisopropyl ethylamine in 75 ml of acetonitrile at such a rate that the temperature did not exceed 15° C. The solution was stirred at ambient temperature overnight and then concentrated. The residue was dissolved in 200 ml of methylene chloride and 50 ml of ethyl acetate and washed successively with 50 ml portions of water, 2N hydrochloric acid solution (twice), water and dilute sodium bicarbonate solution, dried (sodium sulfate) and concentrated to give 16.4 g of gum. The gum was purified by column chromatography on 320 g of silica gel eluted with a gradient of 0–35% acetone in benzene. The appropriate fractions were combined and concentrated to give a solid. This solid was recrystallized from benzene-acetonitrile to yield 6.7 g (47%) of a white solid, mp 133°–134° C.

Analysis: Calculated for $C_9H_{13}ClN_2O_7S_2$: C, 29.96; H, 3.63; N, 7.76. Found: C, 30.00; H, 3.67; N, 7.76.

EXAMPLE 130

Sulfamic acid 2-[3-[2-[(aminosulfonyl)oxy]ethoxy]phenoxy]ethyl ester

To a suspension of 25.0 g (0.13 mole) of resorcinol-bis($\beta$-hydroxyethyl)ether (Lancaster Synthesis, Windham, NH 03087) in 150 ml of acetonitrile was added simultaneously 170 ml (0.53 mole) of sulfamoyl chloride solution (3.14M solution in acetonitrile) and 54.1 g (0.54 mole) of triethylamine (temperature $\leq 15$° C.) and the reaction mixture was stirred at ambient temperature overnight. The reaction mixture was treated with 200 ml of water and 300 ml of ethyl acetate, the layers were separated, and the organic layer was washed with two 200 ml portions of water. The organic solvents were evaporated under reduced pressure and the solid residue was treated with 500 ml of ethyl acetate and 200 ml of water. The mixture was filtered[1] and the filtrate layers were separated. The organic layer was washed with five 200 ml portions of water (filtrate pH neutral to pH paper) and dried (magnesium sulfate). The solvent was evaporated under reduced pressure and the solid residue was dissolved in 300 ml of ethyl acetate and filtered through celite. The filtrate was evaporated under reduced pressure and the solid residue was recrystallized from ethyl acetate to yield 19.6 g (44%) of an off-white solid, mp 147°–149° C.

[1] The filter cake (14.0 g, 31%) was shown by $^1$H NMR to be mainly the desired product. Total yield 33.6 g (75%).

Analysis: Calculated for $C_{10}H_{16}N_2O_8S_2$: C, 33.70; H, 4.53; N, 7.86. Found: C, 34.06; H, 4.65; N, 7.83.

EXAMPLE 131

Sulfamic acid 2-(4-hydroxyphenoxy)ethyl ester

To a solution of 25.8 g (0.08 mole) of sulfamic acid 2-[4-(phenylmethoxy)phenoxy]ethyl ester in 150 ml of tetrahydrofuran was added 0.5 teaspoon of 10% palladium on carbon catalyst and the mixture was hydrogenated in a Parr bottle at 40° C. overnight. The catalyst was removed and a fresh 0.5 teaspoon of 10% palladium on carbon catalyst was added and the mixture was hydrogenated at 40° C. for 3 hr whereby hydrogen uptake ceased. The catalyst was removed by filtration through Celite ® and the filtrate was evaporated under reduced pressure to give a viscous oil that solidified upon standing. The solid was recrystallized from ethyl acetate-chloroform to yield 18.0 g (97%) of a shiny, white solid, mp 92°–93° C.

Analysis: Calculated for $C_8H_{11}NO_5S$: C, 41.20; H, 4.75; N, 6.01. Found: C, 41.17; H, 4.81; N, 6.03.

EXAMPLE 132

Sulfamic acid 2-(3-hydroxyphenoxy)ethyl ester

To a solution of 17.1 g (.053 mole) of sulfamic acid 2-[3-(phenylmethoxy)phenoxy]ethyl ester in 250 ml of tetrahydrofuran was added 0.5 teaspoon of 5% palladium on carbon catalyst and the mixture was hydrogenated in a Parr bottle at 40° C. for 2 hr. The catalyst was removed and a fresh 0.5 teaspoon of 5% palladium on carbon catalyst was added and the mixture was hydrogenated at 40° C. for 19 hr, whereby hydrogen uptake ceased. The catalyst was removed by filtration through Celite ® and the solvent was evaporated under reduced pressure to yield 12.3 g of a brown, viscous oil that solidified after standing for five weeks at ambient temperature. The solid was triturated with ethyl ether-petroleum ether into a paste. The solvents were decanted and the paste was dried to yield 8.9 g (72%) a white solid, mp 56°–60° C.

Analysis: Calcuated for $C_8H_{11}NO_5S$: C, 41.20; H, 4.75; N, 6.01. Found: C, 41.25; H, 4.80; N, 5.92.

TABLE 1

| Example | A | $R^1, R^2$ | z | p | Salt |
|---|---|---|---|---|---|
| 1 | 2-OCH$_3$C$_6$H$_4$OCH$_2$CHCH$_2$ (|  |) | H, H | 2 | 0 | — |
| 2 | 2-OCH$_3$C$_6$H$_4$OCH$_2$CHCH$_2$ (|  |) | H, CH$_3$ | 2 | 0 | — |
| 3 | C$_6$H$_5$OCH$_2$CH—CH$_2$ (|  |) | H, H | 2 | 0 | — |
| 4 | C$_6$H$_5$OCH$_2$CH$_2$— | H, H | 1 | 0 | — |
| 5 | 2-C(O)OHC$_6$H$_4$— | H, H | 1 | 0 | — |
| 6 | C$_6$H$_5$O(CH$_2$)$_3$— | H, H | 1 | 0 | — |

TABLE 1-continued

| Example | A | $R^1$, $R^2$ | z | P | Salt |
|---|---|---|---|---|---|
| 7 | $C_6H_5O-CHCH_2-$<br>          $\|$<br>          $CH_2-$ | H, H | 2 | 0 | — |
| 8 | $2\text{-}OCH_3C_6H_4OCH_2CHOHCH_2-$ | $CH_3$, $CH_3$ | 1 | 1 | — |
| 9 | $2\text{-}OCH_3C_6H_4OCH_2CHCH_2O\overset{O}{\overset{\|}{C}}NH_2$ | H, H | 1 | 1 | — |
| 10 | $[C_6H_5OCH_2]_2CH-$ | H, H | 1 | 0 | — |
| 11 | $4\text{-}ClC_6H_4OCH_2CHCH_2$ | H, H | 1 | 0 | — |
| 12 | $2\text{-}ClC_6H_4O(CH_2)_2-$ | H, H | 1 | 0 | — |
| 13 | $4\text{-}ClC_6H_4O(CH)_2-$ | H, H | 1 | 0 | — |
| 14 | $3\text{-}CH_3C_6H_4O(CH_2)_2-$ | H, H | 1 | 0 | — |
| 15 | $3\text{-}OCH_3C_6H_4O(CH_2)_2-$ | H, H | 1 | 0 | — |
| 16 | $4\text{-}CH_3C_6H_4O(CH_2)_2-$ | H, H | 1 | 0 | — |
| 17 | $2\text{-}CH_3C_6H_4O(CH_2)_2-$ | H, H | 1 | 0 | — |
| 18 | $C_6H_5O(CH_2)_4-$ | H, H | 1 | 1 | — |
| 19 | $4\text{-}OCH_3C_6H_4O(CH_2)_2-$ | H, H | 1 | 0 | — |
| 20 | $C_6H_5CH_2O(CH_2)_2-$ | H, H | 1 | 0 | — |
| 21 | $C_6H_5-$ | H, H | 1 | 0 | — |
| 22 | $2\text{-}OCH_3C_6H_4O(CH_2)_2-$ | H, H | 1 | 0 | — |
| 23 | $C_6H_5OCHCH_3CH_2-$ | H, H | 1 | 0 | — |
| 24 | $4\text{-}ClC_6H_4OC(CH_3)_2CH_2-$ | H, H | 1 | 0 | — |
| 25 | $3\text{-}ClC_6H_4O(CH_2)_2-$ | H, H | 1 | 0 | — |
| 26 | $4\text{-}BrC_6H_4O(CH_2)_2-$ | H, H | 1 | 0 | — |
| 27 | $2,4\text{-}diClC_6H_3O(CH_2)_2-$ | H, H | 1 | 1 | — |
| 28 | $3,4\text{-}diClC_6H_3O(CH_2)_2-$ | H, H | 1 | 0 | — |
| 29 | $4\text{-}ClC_6H_4O(CH_2)_2-$ | H, $CH_3$ | 1 | 0 | — |
| 30 | $C_6H_5OCHCH_3(CH_2)_2-$ | H, H | 1 | 0 | — |
| 31 | $4\text{-}ClC_6H_4O(CH_2)_2-$ | $CH_3$, $CH_3$ | 1 | 0 | — |
| 32 | $C_6H_5OC(CH_3)_2CH_2-$ | H, H | 1 | 0 | — |
| 33 | $2\text{-}OCH_3C_6H_4OCH_2CHCH_2$ | $CH_3$, $CH_3$ | 2 | 0 | — |
| 34 | $4\text{-}ClC_6H_4-$ | H, H | 1 | 0 | — |
| 35 | $3\text{-}ClC_6H_4-$ | H, H | 1 | 0 | — |
| 36 | $3\text{-}OCH_3C_6H_4OCH_2CHCH_2$<br>                         2  1 | 1.H, H<br>2.H, $CH_3$ | 2 | 0 | — |
| 37 | $C_6H_5-$ | H, $CH_3$ | 1 | 0 | — |
| 38 | $4\text{-}CH_3C(O)NHC_6H_4-$ | H, H | 1 | 0 | — |
| 39 | $2\text{-}OCH_3C_6H_4OCH_2CH-CH_2$<br>                        $\|$<br>                        OH | H, $CH_3$ | 1 | 1 | — |
| 40 | $2\text{-}OCH_3C_6H_4OCH_2CH-CH_2$<br>                        $\|$<br>                        OH | H, H | 1 | 1 | — |
| 41 | $2\text{-}OCH_3C_6H_4OCH_2CH-CH_2$<br>                        2  1 | 1.H, $CH_3$<br>2.H, H | 2 | 0 | — |
| 42 | 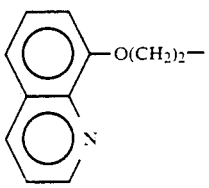 | H, H | 1 | 0 | HCl |
| 43 | $4\text{-}ClC_6H_4-$ | H, $CH_3$ | 1 | 0 | — |
| 44 | $2\text{-}OCH_3C_6H_4OCH_2CH-CH_2$ | H, $C_2H_5$ | 2 | 0 | — |

TABLE 1-continued

| Example | A | R¹, R² | z | P | Salt |
|---|---|---|---|---|---|
| 45 | C₆H₅OCH₂CH—CH₂ (with substituents) | H, C₂H₅ | 2 | 0 | — |
| 46 | 3-pyridyl-O(CH₂)₂— | H, H | 1 | 0 | HCl |
| 47 | 4-(imidazol-1-yl)C₆H₄—O(CH₂)₂— | H, H | 1 | 0 | — |
| 48 | C₆H₅OCH₂CH—CH₂ | H, CH(CH₃)₂ | 2 | 0 | — |
| 49 | C₆H₅OCH₂CH—CH₂ | H, C(CH₃)₃ | 2 | 0 | — |
| 50 | 4-CH₃OC(O)C₆H₄— | H, H | 1 | 0 | — |
| 51 | 3-CH₃OC(O)C₆H₄— | H, H | 1 | 0 | — |
| 52 | 3-CH₃C(O)NHC₆H₄— | H, H | 1 | 0 | — |
| 53 | 4-HOC(O)C₆H₄— | H, H | 1 | 0 | — |
| 54 | 4-(imidazol-1-yl)C₆H₄— | H, H | 1 | 0 | HCl |
| 55 | C₆H₅— | H, CH(CH₃)₂ | 1 | 0 | — |
| 56 | 3,4-diClC₆H₃— | H, H | 1 | 0 | — |
| 57 | 4-O₂NC₆H₄— | H, H | 1 | 0 | — |
| 58 | C₆H₅— | H, C₂H₅ | 1 | 0 | — |
| 59 | C₆H₅-(1,2,5-thiadiazol-3-yl) | H, H | 1 | 0 | — |
| 60 | 3-O₂NC₆H₄— | H, H | 1 | 0 | — |
| 61 | 3-CF₃C₆H₄— | H, H | 1 | 0 | — |
| 62 | 4-C₆H₅C₆H₄— | H, H | 1 | 0 | — |
| 63 | 4-NO₂,3-CF₃C₆H₃— | H, H | 1 | 0 | — |
| 64 | 4-methyl-7-methylcoumarin-yl | H, H | 1 | 0 | — |
| 65 | 2-ClC₆H₄— | H, H | 1 | 0 | — |
| 66 | 4-(imidazol-1-yl)C₆H₄— | H, CH₃ | 1 | 0 | HCl |
| 67 | 2-naphthyl | H, H | 1 | 0 | — |
| 68 | C₆H₅OCH₂CHCH₂ | H, CH₃ | 2 | 0 | — |
| 69 | 4-(1,2,4-triazol-1-yl)C₆H₄— | H, H | 1 | 0 | 0.5 HCl |

TABLE 1-continued

| Example | A | R¹, R² | z | P | Salt |
|---|---|---|---|---|---|
| 70 | 4-C₆H₅C(O)C₆H₄— | H, H | 1 | 0 | — |
| 71 | 3-BrC₆H₄— | H, H | 1 | 0 | — |
| 72 | 4-CF₃C₆H₄— | H, H | 1 | 0 | HCl |
| 73 | 3-C₆H₅C(O)C₆H₄— | H, H | 1 | 0 | — |
| 74 | 3-(CH₃)₂NC₆H₄— | H, H | 1 | 0 | HCl |
| 75 |  | H, CH₃ | 1 | 0 | HCl.0.5 H₂O |
| 76 | 4-H₂NSO₂C₆H₄— | H, H | 1 | 0 | — |
| 77 | 3-CNC₆H₄— | H, H | 1 | 0 | — |
| 78 | 3-Ph—C₆H₄— | H, H | 1 | 0 | — |
| 79 | C₆H₅OCH—CH₂—<br>         \|<br>         CH₂— | H, CH₃ | 2 | 0 | — |
| 80 | 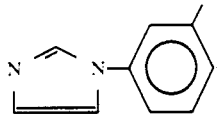 | H, H | 1 | 0 | HCl |
| 81 | 3-IC₆H₄— | H, H | 1 | 0 | — |
| 82 | C₆H₅— | CH₃, CH₃ | 1 | 0 | — |
| 83 | 4-CH₃C₆H₄— | H, H | 1 | 0 | — |
| 84 | 3-(CH₃)₃CC₆H₄— | H, H | 1 | 0 | — |
| 85 | 3,5-diClC₆H₃— | H, H | 1 | 0 | — |
| 86 | 2,3-diClC₆H₃— | H, H | 1 | 0 | — |
| 87 | 4-CNC₆H₄— | H, H | 1 | 0 | — |
| 88 | 4-OCH₃C₆H₄— | H, H | 1 | 0 | — |
| 89 | 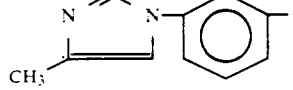 | H, H | 1 | 0 | HCl |
| 90 | 2-OCH₃C₆H₄— | H, H | 1 | 0 | — |
| 91 | 2-OCH₃C₆H₄OCH₂CH—CH₂(S)-(−)<br>                            \|     \| | H, H | 2 | 0 | — |
| 92 | 2-OCH₃C₆H₄OCH₂CH—CH₂(R)-(+)<br>                            \|     \| | H, H | 2 | 0 | — |
| 93 | 2,6-diClC₆H₃— | H, H | 1 | 0 | — |
| 94 | 3-CH₃C₆H₄— | H, H | 1 | 0 | — |
| 95 | 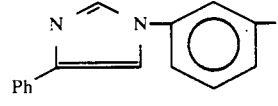 | H, H | 1 | 0 | — |
| 96 | 3-FC₆H₄— | H, H | 1 | 0 | — |
| 97 | 3,5-diCF₃C₆H₃ | H, H | 1 | 0 | — |
| 98 | 3,5-diFC₆H₃— | H, H | 2 | 0 | — |
| 99 | 4-FC₆H₄— | H, H | 2 | 0 | — |
| 100 |  | H, H | 1 | 0 | — |
| 101 | 2-OCH₃C₆H₄O(CH₂)₃— | H, H | 1 | 0 | — |
| 102 | 2-OCH₃C₆H₄— | H, CH₃ | 1 | 0 | — |
| 103 | 4-IC₆H₄— | H, H | 1 | 0 | — |

TABLE 1-continued

| Example | A | $R^1, R^2$ | z | P | Salt |
|---|---|---|---|---|---|
| 104 | [imidazole-N-C6H4-O(CH2)3-] | H, H | 1 | 0 | — |
| 105 | [C6H4-O(CH2)2-] with CH3 | H, H | 2 | 0 | — |
| 106 | 3-OCH3C6H4— | H, H | 2 | 0 | — |
| 107 | [2-methylimidazole-N-C6H4-O(CH2)2-] | H, H | 1 | 0 | — |
| 108 | [1,2,4-triazole-N-C6H4-O(CH2)2-] | H, H | 1 | 0 | — |
| 109 | [4-methylimidazole-N-C6H4-O(CH2)2-] | H, H | 1 | 0 | — |
| 110 | [2-methylimidazole-N-C6H4-] | H, H | 1 | 0 | — |
| 111 | 2-FC6H4— | H, H | 1 | 0 | — |
| 112 | 2-OCH3C6H4O(CH2)2— | H, CH3 | 2 | 0 | — |
| 113 | 3-(ClCH2CH2O)—C6H4— | H, H | 2 | 0 | — |
| 114 | C6H5O(CH2)2— | H, CH3 | 1 | 0 | — |
| 115 | 2-OC2H5C6H4OCH2CH—CH2 | H, H | 2 | 0 | — |
| 116 | 3-PhCH2OC6H4O(CH2)2— | H, H | 1 | 0 | — |
| 117 | 2-PhCH2OC6H4OCH2CH—CH2 | H, CH3 | 2 | 0 | — |
| 118 | 3-(C2H5)2NC6H4O(CH2)2— | H, H | 1 | 0 | — |
| 119 | [C6H4-] with CH3 | H, H | 2 | 0 | — |
| 120 | 2-OC2H5C6H4OCH2CH—CH2 | H, CH3 | 2 | 0 | — |
| 121 | [2-methylimidazole-N-C6H4-] | H, H | 1 | 0 | HCl |
| 122 | 2-OHC6H4OCH2CH—CH2 | H, CH3 | 2 | 1 | — |

TABLE 1-continued

| Example | A | $R^1, R^2$ | z | P | Salt |
|---|---|---|---|---|---|
| 123 | 2-OCH$_3$C$_6$H$_4$OCH$_2$CH—CH$_2$,(S)-(−) with CH$_2$ branch | H, CH$_3$ | 2 | 0 | — |
| 124 | 2-OCH$_3$C$_6$H$_4$OCH$_2$CH—CH$_2$,(R)-(+) with CH$_2$ branch | H, CH$_3$ | 2 | 0 | — |
| 125 | —(CH$_2$)$_2$O—C$_6$H$_4$—O(CH$_2$)$_2$— | H, H | 2 | 0 | — |
| 126 | 4-PhCH$_2$OC$_6$H$_4$O(CH$_2$)$_2$— | H, H | 1 | 0 | — |
| 127 | 3-ClC$_6$H$_4$— | CH$_3$, CH$_3$ | 1 | 0 | — |
| 128 | 2-OCH$_3$C$_6$H$_4$— | CH$_3$, CH$_3$ | 1 | 0 | — |
| 129 | 4-ClC$_6$H$_4$OCH—CH$_2$— with CH$_2$— branch | H, H | 2 | 0 | — |
| 130 | —(CH$_2$)$_2$—O—C$_6$H$_4$—O—(CH$_2$)$_2$— | H, H | 2 | 0 | — |
| 131 | 4-HOC$_6$H$_4$O(CH$_2$)$_2$— | H, H | 1 | 1 | — |
| 132 | 3-OHC$_6$H$_4$O(CH$_2$)$_2$— | H, H | 1 | 1 | — |

ANTICONVULSANT TESTING PROCEDURE

Test compounds were prepared as suspensions or solutions in 0.5% aqueous methyl cellulose, with sonification if necesary. The initial screening dose was 100 mg/kg in a volume of 10 ml/kg given intraperitoneally. Groups of eight adult female mice were treated with the test compound or vehicle and sixty minutes later each animal was challenged with corneal maximal electroshock (60 Hz, 34 mA, 8 msec pulse width) for 200 msec. The absence of tonic seizure upon cessation of the stimulation was considered an anticonvulsant effect in that animal. For ED$_{50}$ determinations, a minimum of 3 logarithmically spaced doses were used. The number of animals protected from tonic seizures at a given dose of test drug was determined. The ED$_{50}$, 95% confidence limit and potency are obtained using a computerized probit analysis based on the method of J. T. Litchfield and F. Wilcoxon, J. Pharm. Exp. Ther. 96, 99–113 (1949).

Compounds of Examples 7, 37, 43 and 80 are exemplary of compounds of this invention having an ED$_{50}$ of ≦25 mg/kg in this test procedure.

PHARMACEUTICAL COMPOSITIONS

The invention further provides pharmaceutical compositions for administration to a living animal body comprising, as active ingredients, at least one of the compounds according to the invention in association with a pharmaceutical carrier or excipient. The compounds are thus presented in a therapeutic composition suitable for oral, rectal or parenteral administration. Thus, for example, compositions for oral administration are preferably solids and can take the form of capsules, tablets or coated tablets containing carriers conveniently used in the pharmaceutical art. Suitable tableting carriers or excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water, or a parenterally acceptable oil; e.g., arachis oil, contained in ampoules.

In compositions for rectal administration the carrier can comprise a suppository base, e.g., cocoa butter, or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be obtained consistent with the dosage form employed. The exact individual dosages, as well as daily dosages, will, of course, be determined according to standard medical principles under the direction of a physician or veterinarian. Generally the oral effective dose to either prevent or treat convulsions, would consist of unit dosages containing an amount of compound equivalent to about 1 to about 100 mg/kg of body weight and thus are contemplated. Based on all of the above considerations, a choice in a range of unit oral dosages for humans of about 10 to about 1000 mg is contemplated, preferably about 10 to 600 mg. Daily dosages of about 30 to 3000 mg are contemplated for humans and obviously several unit dosage forms may be administered at about the same time. However, the scope of the invention is not to be limited by these contemplations due to the uncertainty in transpositions discussed above.

Examples of unit dosage compositions are as follows:

| Ingredients | Capsules Per Cap. |
|---|---|
| 1. Active ingredient | 10.0 mg |

| Capsules | |
|---|---|
| Ingredients | Per Cap. |
| 2. Lactose | 146.0 mg |
| 3. Magnesium Stearate | 4.0 mg |
| | 160.0 mg |

PROCEDURE

Step 1. Blend ingredients 1, 2 and 3.
Step 2. Pass blend from Step 1 through a No. 30 mesh screen (0.59 mm) and blend again.
Step 3. Fill powder blend from Step 2 into No. 1 hard gelatin capsules.

| Ingredients | Mg./Tab. |
|---|---|
| Tablets (10 mg) | |
| 1. Active Ingredient | 10.0 mg |
| 2. Corn starch | 20.0 mg |
| 3. Alginic acid | 20.0 mg |
| 4. Sodium alginate | 20.0 mg |
| 5. Magnesium stearate | 1.3 mg |
| | 71.3 mg |
| Tablets (50 mg) | |
| 1. Active Ingredient | 50.0 mg |
| 2. Milo starch | 20.0 mg |
| 3. Corn starch | 38.0 mg |
| 4. Lactose | 90.0 mg |
| 5. Magnesium stearate | 2.0 mg |
| | 200.0 mg |

PROCEDURE

Step 1. Blend ingredients 1, 2 and 3 and 4.
Step 2. Add sufficient water portion wise to the blend from Step 1 with careful stirring after each addition. Such additions of water and stirring continue until the mass is of a consistency to permit its conversion to wet granules.
Step 3. The wet mass prepared in Step 2 is converted to granules by passing it through an oscillating granulator, using a #8-mesh (2.36 mm) screen.
Step 4. The wet granules prepared in Step 3 are dried in an oven at 140° F.
Step 5. Dried granules from Step 4 are passed through an oscillating granulator, using a No. 10-mesh (2.00 mm) screen.
Step 6. Lubricate the dry granules from Step 5 by blending with ingredient No. 5.
Step 7. The lubricated granules from Step 6 are compressed on a suitable tablet press.

| Intravenous Injection | |
|---|---|
| Ingredients | Per ml. |
| 1. Active Ingredient | 10.0 mg |
| 2. Isotonic pH 4.0 buffer solution q.s. to | 1.0 ml |

PROCEDURE

Step 1. Dissolve the active ingredient in the buffer solution.
Step 2. Aseptically filter the solution from Step 1.
Step 3. The sterile solution is now aseptically filled into sterile ampuls.
Step 4. The ampuls are sealed under aseptic conditions.

| Intramuscular Injection | |
|---|---|
| Ingredients | Per ml. |
| 1. Active Ingredients | 50.0 mg |
| 2. Isotonic pH 4.0 buffer solution q.s. to | 5.0 ml |

PROCEDURE

Step 1. Dissolve the active ingredient in the buffer solution.
Step 2. Aseptically filter the solution from Step 1.
Step 3. The sterile solution is now aseptically filled into sterile ampuls.
Step 4. The ampuls are sealed under aseptic conditions.

| Suppositories | |
|---|---|
| Ingredients | Per Supp. |
| 1. Active ingredient | 500.0 mg |
| 2. Polyethylene Glycol 1000 | 1350.0 mg |
| 3. Polyethylene Glycol 4000 | 450.0 mg |
| | 2300.0 mg |

PROCEDURE

Step 1. Melt ingredients 2 and 3 together and stir until uniform.
Step 2. Dissolve 1 in the molten mass from Step 1 and stir until uniform.
Step 3. Pour the molten mass from Step 2 into suppository molds and allow to cool.
Step 4. Remove the suppositories from molds and wrap.

Various modifications and equivalents will be apparent to one skilled in the art and may be made in the compounds, method, and compositions of the present invention without departing from the spirit or scope thereof, and it is therefore to be understood that the invention is to be limited only the scope of the appended claims.

What is claimed is:

1. A method of treating convulsions in a mammal, comprising administering to said mammal an effective anticonvulsant amount of a compound having the formula:

$$(HO)_p\text{—}A\text{—}[OS(O)_2NR^1R^2]_z$$

wherein A is substituted on one or more carbon atoms by an aminosulfonyloxy radical, said A being selected from aryl, arylalkyl, or aryloxyalkyl with a proviso that when A is arylalkyl, and the aryl moiety is phenyl, z is always two; Aryl or aryl moieties are selected from:

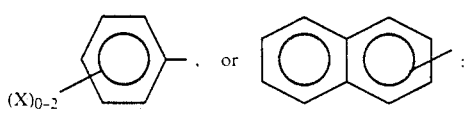

X is selected from hydrogen, halo, phenyl, phenoxy, benzoyl, loweralkyl, loweralkoxy, carboxy, amino, loweralkyl amino, diloweralkyl amino, acetamido, cyano, nitro, loweralkoxycarbonyl, 1H-imidazol-1-yl, aminosulfonyl, 4-phenyl-1H-imidazol-1-yl, 4-methyl-1H-imidazol-1-yl, 1-triazolyl, 2-methyl- 1H-imidazol-1-yl, phenylloweralkoxy, or hydroxy; z is 1 or 2 and is the number of $-OS(O)_2NR^1R^2$ groups, p is 0 or 1 and is the number of untreated hydroxyl groups, $R^1$ and $R^2$, same or different, are hydrogen or loweralkyl; the optical isomers thereof, when they can be formed; and the pharmaceutically acceptable addition salts thereof, when they can be formed.

2. The method of claim 1 wherein the compound used is 3-phenoxy-1,2-propanediol bisulfamate ester.

3. The method of claim 1 wherein the compound used is 2-phenoxyethanol sulfamate ester.

4. The method of claim 1 wherein the compound used is 2-phenoxy-1,3-propanediol disulfamate ester.

5. The method of claim 1 wherein the compound used is sulfamic acid phenyl ester.

6. The method of claim 1 wherein the compound used is 2-(4-chlorophenoxy)-2-methylpropanol sulfamate ester.

7. The method of claim 1 wherein the compound used is methylsulfamic acid phenyl ester.

8. The method of claim 1 wherein the compound used is methylsulfamic acid 4-chlorophenyl ester.

9. The method of claim 1 wherein the compound used is sulfamic acid 2-[4-[(1H-imidazol-1-yl)phenoxy]ethyl ester hydrochloride.

10. The method of claim 1 wherein the compound used is sulfamic acid 3-(1H-imidazo-1-yl)phenyl ester monohydrochloride.

11. The method of claim 1 wherein the compound used is dimethylsulfamic acid phenyl ester.

12. The method of claim 1 wherein the compound used is sulfamic acid 4-(2-methyl-1H-imidazol-1-yl)phenyl ester hydrochloride.

13. The method of claim 1 wherein the compound used is sulfamic acid 3-[(aminosulfonyl)oxy]-2-(4-chlorophenoxy)propyl ester.

14. The method of claim 1 wherein the compound used is sulfamic acid 2-(3-hydroxyphenoxy)ethyl ester.

* * * * *